US009764028B2

United States Patent
Li et al.

(10) Patent No.: US 9,764,028 B2
(45) Date of Patent: Sep. 19, 2017

(54) FUSION PROTEIN COMPRISING DIPHTHERIA TOXIN NON-TOXIC MUTANT CRM197 OR FRAGMENT THEREOF

(71) Applicants: XIAMEN UNIVERSITY, Xiamen (CN); XIAMEN INNOVAX BIOTECH CO., LTD., XIAMEN (CN)

(72) Inventors: Shaowei Li, Xiamen (CN); Cuiling Song, Xiamen (CN); Chunyan Yang, Xiamen (CN); Ying Gu, Xiamen (CN); Wenxin Luo, Xiamen (CN); Ningshao Xia, Xiamen (CN)

(73) Assignees: XIAMEN UNIVERSITY, Xiamen (CN); XIAMEN INNOVAX BIOTECH CO., LTD., Xiamen (CN)

( * ) Notice: Subject to any disclaimer, the term of this patent is extended or adjusted under 35 U.S.C. 154(b) by 0 days.

(21) Appl. No.: 15/248,850

(22) Filed: Aug. 26, 2016

(65) Prior Publication Data

US 2017/0015713 A1    Jan. 19, 2017

Related U.S. Application Data

(62) Division of application No. 14/123,305, filed as application No. PCT/CN2012/076378 on Jun. 1, 2012, now Pat. No. 9,512,185.

(30) Foreign Application Priority Data

Jun. 1, 2011   (CN) .......................... 2011 1 0145419

(51) Int. Cl.
  *C07K 14/34*    (2006.01)
  *C07K 14/005*   (2006.01)
  (Continued)

(52) U.S. Cl.
  CPC .............. *A61K 39/39* (2013.01); *A61K 39/05* (2013.01); *A61K 39/12* (2013.01); *A61K 39/29* (2013.01);
  (Continued)

(58) Field of Classification Search
  None
  See application file for complete search history.

(56) References Cited

U.S. PATENT DOCUMENTS 7,960,514 B2   6/2011  Lauder et al.
8,227,403 B2*  7/2012  Arumugham ...... A61K 39/0007
                                                      514/1.1

(Continued)

FOREIGN PATENT DOCUMENTS

CN    101050236 A    10/2007
CN    101050238 A    10/2007
(Continued)

OTHER PUBLICATIONS

Fiers et al. (Vaccine, 2009, p. 6280-6283).*
(Continued)

*Primary Examiner* — Agnieszka Boesen
(74) *Attorney, Agent, or Firm* — Banner & Witcoff, Ltd.

(57) ABSTRACT

Provided in the present invention are a diphtheria toxin non-toxic mutant CRM197 or a fragment thereof as an adjuvant in a fusion protein and the use thereof to enhance the immunogenicity of a target protein fused therewith, for example, an HEV capsid protein, or an influenza virus M2 protein or an immunogenic fragment thereof. Also provided is a method for enhancing the immunogenicity of a target protein, comprising the fusion expression of the CRM197 or the fragment thereof with the target protein to form a fusion protein. Further provided is a fusion protein comprising the CRM197 or the fragment thereof and a target protein, the
(Continued)

CRM197 or the fragment thereof enhancing the immunogenicity of the target protein. The present invention also provides an isolated nucleic acid encoding the fusion protein, a construct and a vector comprising said nucleic acid, and a host cell comprising the nucleic acid.

17 Claims, 28 Drawing Sheets

(51) Int. Cl.
  *A61K 39/29* (2006.01)
  *C12N 15/62* (2006.01)
  *A61K 39/39* (2006.01)
  *C12N 9/10* (2006.01)
  *A61K 39/12* (2006.01)
  *A61K 39/05* (2006.01)
  *C12N 7/00* (2006.01)
  *A61K 38/00* (2006.01)
  *A61K 39/00* (2006.01)

(52) U.S. Cl.
  CPC ............ *C07K 14/005* (2013.01); *C07K 14/34* (2013.01); *C12N 7/00* (2013.01); *C12N 9/1048* (2013.01); *C12N 15/62* (2013.01); *A61K 38/00* (2013.01); *A61K 2039/55505* (2013.01); *A61K 2039/55516* (2013.01); *A61K 2039/55544* (2013.01); *A61K 2039/6037* (2013.01); *C07K 2319/03* (2013.01); *C07K 2319/55* (2013.01); *C07K 2319/74* (2013.01); *C12N 2760/16122* (2013.01); *C12N 2760/16134* (2013.01); *C12N 2770/28122* (2013.01); *C12N 2770/28134* (2013.01)

(56) References Cited

U.S. PATENT DOCUMENTS

| | | | |
|---|---|---|---|
| 8,252,897 B2* | 8/2012 | Davis | A61K 38/16 424/190.1 |
| 9,512,185 B2 | 12/2016 | Li et al. | |
| 2005/0013815 A1 | 1/2005 | Schenk | |
| 2006/0233822 A1 | 10/2006 | Xia et al. | |
| 2008/0260773 A1 | 10/2008 | Del Giudice et al. | |
| 2009/0010966 A1 | 1/2009 | Davis et al. | |
| 2010/0215662 A1 | 8/2010 | Bradbury | |

FOREIGN PATENT DOCUMENTS

| | | |
|---|---|---|
| EP | 0616034 A2 | 9/1994 |
| JP | 06292593 A2 | 10/1994 |
| WO | 9713855 A0 | 4/1997 |
| WO | 0141800 A2 | 6/2001 |
| WO | 02096467 A2 | 12/2002 |
| WO | 2004069163 A2 | 8/2004 |
| WO | 2004083251 A2 | 9/2004 |
| WO | 2005105140 A2 | 11/2005 |
| WO | 2006037658 A1 | 4/2006 |
| WO | 2006075170 A1 | 7/2006 |
| WO | 2009000826 A1 | 12/2008 |
| WO | 2010151544 A1 | 12/2010 |
| WO | 2011015590 A1 | 2/2011 |
| WO | 2011036560 A2 | 3/2011 |

OTHER PUBLICATIONS

Bennett et al., "Refined structure of dimeric diphtheria toxin at 2.0 Å resolution," Protein Science, 1994, vol. 3, pp. 1444-1463.

DeLange et al., "Amino-acid sequence of Fragment A, an enzymically active fragment from diphtheria toxin," PNAS, Biochemistry, Jan. 1976, vol. 73, pp. 69-72.

Extended European Search Report for EP Application No. 12793630.0 dated Jan. 12, 2015.

International Preliminary Report on Patentability and Written Opinion for PCT/CN2012/076378, dated Dec. 2, 2013.

Japanese Patent Application No. 2014-513045, Notice of Reasons for Rejection dated Dec. 1, 2015.

Johnson, "Diphtheria Toxin Mutations: Their Role in Structure—Function Studies," Toxins and Signal Transduction, 1997, Chapter 12, 10 pages.

Korean Office Action for Serial No. 10-2014-7000012 dated Dec. 9, 2015, 13 pages.

Lee et al., "Expression and Immunogenicity of a Recombinant Diphtheria Toxin Fragment A in *Streptococcus gordonii*," Applied and Environmental Microbiology, Aug. 2004, vol. 70, No. 8, pp. 4569-4574.

Li et al., "A bacterially expressed particulate hepatitis E vaccine: antigenicity, immunogenicity and protectivity on primates," Vaccines 23, 2005, pp. 2893-2901.

Li et al., "Mutational Analysis of Essential Interactions Involved in the Assembly of Hepatitis E Virus Capsid," The Journal of Biological Chemistry, 2005, Issue of Feb. 4, vol. 280, No. 5, pp. 3400-3406.

Phalipon and Kaczorek, "Genetically engineered diphtheria toxin fusion proteins carrying the hepatitis B surface antigen," Gene, vol. 55, 1987, pp. 255-263.

Phalipon et al., "Expression of a poliovirus type 1 neutralization epitope on a diphtheria toxin fusion protein," Vaccine, vol. 7, Apr. 1989, pp. 132-136.

Li et al., U.S. Appl. No. 15/248,779, amended claims filed Jun. 27, 2017, 2 pages.

* cited by examiner

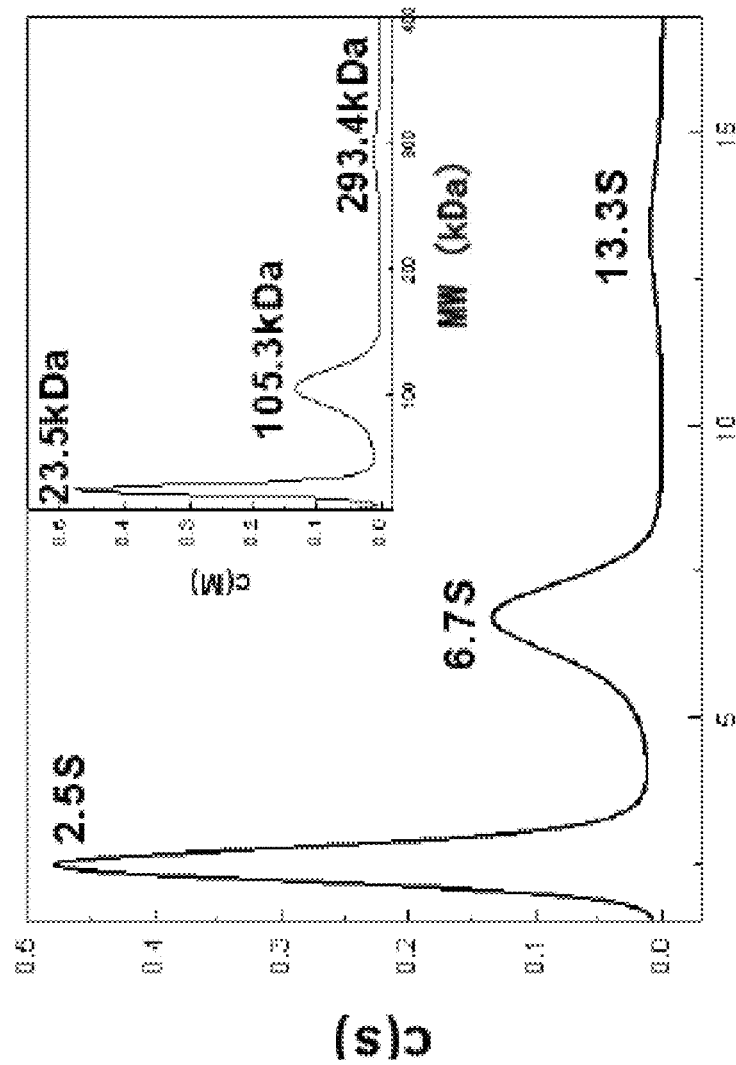

FUSION PROTEIN COMPRISING DIPHTHERIA TOXIN NON-TOXIC MUTANT CRM197 OR FRAGMENT THEREOF

This application incorporates by reference the contents of a 102 kb text file created on Sep. 27, 2016 and named "00768500045substitutesequencelisting.txt," which is the sequence listing for this application.

FIELD OF THE INVENTION

The invention relates to the field of molecular virology and immunology. In particular, the invention relates to a use of a diphtheria toxin non-toxic mutant CRM197 or a fragment thereof as intramolecular adjuvant in a fusion protein for enhancing immunogenicity of a target protein fused thereto (for example, an HEV capsid protein, an influenza virus M2 protein or an immunogenic fragment thereof). The invention also relates to a method for enhancing immunogenicity of a target protein (for example, an HEV capsid protein, an influenza virus M2 protein or an immunogenic fragment thereof), comprising the fusion expression of CRM197 or a fragment thereof with the target protein to form a fusion protein. The invention also relates to a fusion protein comprising CRM197 or a fragment thereof and a target protein (for example, an HEV capsid protein, an influenza virus M2 protein or an immunogenic fragment thereof), wherein said CRM197 or a fragment thereof enhances immunogenicity of the target protein. The invention also relates to an isolated nucleic acid encoding the fusion protein, a construct and a vector comprising the nucleic acid, and a host cell comprising the nucleic acid. The invention also relates to a use of the fusion protein in the manufacture of a pharmaceutical composition or a vaccine.

BACKGROUND OF THE INVENTION

Diphtheria toxin (DT) has been deeply studied. The studies on structure show that diphtheria toxin consists of three domains: N-terminal Catalytic Domain C (aa 1-190, C domain) (also called Fragment A), middle Transmembrane Domain T (aa 201-384, T domain), and C-terminal Receptor Binding domain R (aa 386-535, R domain) (Choe S, Bennett M, Fujii G, et al., Nature. 1992. 357:216-222). ONTAK (DAB389-IL-2), prepared by fusion of the former two domains of diphtheria toxin with interleukin 2 (IL-2), was approved by FDA on the market in 1999, for the treatment of adult cutaneous T-cell lymphoma. This demonstrates that the three domains of diphtheria toxin may be used separately and play their own roles, respectively.

CRM197 (Cross-Reacting Materials 197) is a diphtheria toxin non-toxic mutant (Uchida, T., A. M, Pappenheimer, Jr., R. Gregory, et al., J. Biol. Chem. 1973. 248:3838-3844), which differs from a wild-type gene encoding DT by a single nucleotide mutation, resulting in the amino acid residue at position 52 changed from Gly to Glu (G. Giannini, R. Rappuoli, G. Ratti et al., Nucleic Acids Research. 1984. 12: 4063-4070).

Studies show that although CRM197 has a structure similar to that of a wild-type DT (namely, having said three domains), its Fragment A loses the ability of binding to NAD, is unable to bind to EF2 and thereby loses the cytoxicity possessed by natural DT, indicating that the amino acid residue Gly at position 52 plays an important role in the binding of DT to NAD (K. Moyner, G. Christiansen, Acta path microbial immunolscand sect C. 1984, 92:17-23). Although CRM197 loses the cytotoxicity, it retains a strong immunogenicity comparable to that of a wild-type DT. Therefore, CRM197 is generally used as a protein carrier for crosslinking other haptens so as to prepare conjugate vaccines.

As early as 1985, Porter et al., crosslinked polysaccharides on Hib surface to CRM197 and DT protein carrier, respectively, and prepared them into vaccines, and studied the difference of them in immunogenicity. The experimental results showed that there was no significant difference between the two crosslinked vaccines in terms of immune effect, both of them could stimulate the generation of a strong immune response and immunologic memory in infants (Porter Anderson, Micheal E. Pichichero and Richard A. J. Clin. Invest. 1985: 52-59). After comparing pneumococcal conjugate vaccines crosslinked to various proteins, it is found that the vaccines wherein CRM197 is used as a protein carrier have a good immune effect in animal experiments and clinical trials, and CRM197 is safe without a side-effect of toxicity (Black, S., H. Shinefield, et al. Pediatr Infect Dis J, 2000, 19(3); 187-195). In current, pneumococcal conjugate vaccines, in which CRM197 is used as a protein carrier, mainly refer to PCV7, PCV9, PCV13, and the like. The results of clinical trials showed that these vaccines had good immunogenicity and safety in children less than two years old (Barricarte, A., J. Castilla, et al. Clin Infect Dis, 2007, 44(11): 1436-1441; Madhi, S., P. Adrian, et al. Vaccine, 2007, 25(13): 2451-2457; Duggan, S. T. Drugs, 2010, 70(15): 1973-1986). Epidemic meningitis conjugate vaccines can be prepared by crosslinking CRM197 to polysaccharides on surface of *N. menigitidis*. For example, vaccines such as Meningitec (Wyeth Pharmaceuticals), Menjugate (Novartis vaccines), and Menveo (Novartis vaccines), in which CRM197 is used as a protein carrier, have been commercially available.

Although CRM197 loses enzymatic activity and cytotoxity, it is still able to bind to a specific receptor of DT, i.e. heparin-binding EGF-like growth factor (HB-EGF). Since the expression of the receptor is generally up-regulated in cancerous tissues, like DT, CRM197 also has anti-tumor effect (Buzzi, S., D. Rubboli, et al. Immunotherapy, 2004, 53(11)). The studies also found that CRM197 could pass through Blood-Brain-Barrier (BBB), and therefore could be used as a carrier for delivery of drugs to brain (Gaillard, P. J., and A. G. de Boer. J Control Release, 2006, 116(2): 60-62).

Although it has been reported that CRM197 has multiple functions, in particular, has a strong immunogenicity and can be used as immunoadjuvant, it is not reported yet that CRM197 may be used as intramolecular adjuvant for enhancing immunogenicity of a target protein fused thereto in a fusion protein. The invention uses Hepatitis E capsid protein as an example, and demonstrates for the first time that CRM197 or a fragment thereof can enhance immunogenicity of a protein fused thereto in a fusion protein, and thereby can be used as intramolecular adjuvant.

DESCRIPTION OF THE INVENTION

In the invention, unless otherwise specified, the scientific and technical terms used herein have the meanings as generally understood by a person skilled in the art. Moreover, the laboratory operations of cell culture, molecular genetics, nucleic acid chemistry, biological chemistry, and immunology used herein are the routine operations widely used in the corresponding fields. Meanwhile, for the purpose of better understanding of the invention, the definitions and explanations of the relevant terms are provided as follows.

According to the invention, the term "CRM197" refers to a diphtheria toxin non-toxic mutant, which differs from a wild-type diphtheria toxin by an amino acid residue at position 52 changed from Gly to Glu (G. Giannini, R. Rappuoli, G. Ratti et al., Nucleic Acids Research. 1984. 12: 4063-4070). Diphtheria toxin is well known by a person skilled in the art (see, for example, Choe S, Bennett M, Fujii G, et al., Nature. 1992. 357:216-222), whose amino acid sequence may be found by reference to GenBank accession No. AAV70486.1.

In the invention, the exemplary amino acid sequence of CRM197 is set forth in SEQ ID NO: 2. Therefore, in the invention, when the sequence of CRM197 is involved, it is described as the sequence set forth in SEQ ID NO:2. For example, in the expression "amino acid residues from positions 1 to 190 of CRM197", amino acid residues from positions 1 to 190 refers to amino acid residues from positions 1 to 190 of SEQ ID NO: 2. However, a person skilled in the art understands that mutations or variations (including, but not limited to, substitution, deletion and/or addition) may naturally occur in or are introduced artificially into SEQ ID NO: 2 without affecting the biological properties of CRM197. Therefore, in the invention, the term "CRM197" intends to comprise all such polypeptides and variants, including the polypeptide set forth in SEQ ID NO: 2 and its natural or artificial variants, wherein the variants retain the biological properties of CRM197, i.e. have a strong immunogenicity and no cytotoxicity. In addition, when sequence fragments of CRM197 are described, they include not only the sequence fragments of a polypeptide set forth in SEQ ID NO: 2, but also the corresponding sequence fragments of the natural or artificial variants of the polypeptide. For example, the expression "amino acid residues from positions 1 to 190 of CRM197" intends to comprise amino acid residues from positions 1 to 190 of SEQ ID NO: 2 and the corresponding fragments of the variants (natural or artificial) of a polypeptide set forth in SEQ ID NO: 2.

According to the invention, an Hepatitis E virus (HEV) capsid protein refers to a protein encoded by HEV ORF2. The sequence of HEV ORF2 is well known in the art (see, for example, DDBJ accession No. D11092). In the invention, when the sequence of HEV ORF2 is involved, it is described as the sequence set forth in DDBJ accession No. D11092. For example, in the expression "amino acid residues from positions 368 to 606 of a polypeptide encoded by HEV ORF2", amino acid residues from positions 368 to 606 refers to amino acid residues from positions 368 to 606 of a polypeptide encoded by D11092. However, a person skilled in the art understands that mutations or variations (including, but not limited to, substitution, deletion and/or addition) may naturally occur in or are introduced artificially into HEV ORF2 or a polypeptide encoded thereby without affecting the biological properties thereof (such as antigenicity and immunogenicity). Therefore, in the invention, the term "HEV ORF2" intends to comprise all such polypeptides and variants, including the sequence set forth in D11092 and its natural or artificial variants. In addition, when sequence fragments of HEV ORF2 (or a polypeptide encoded thereby) are described, they include not only the sequence fragments of D11092 (or a polypeptide encoded thereby), but also the corresponding sequence fragments of the natural or artificial variants of D11092 (or a polypeptide encoded thereby). For example, the expression "amino acid residues from positions 368 to 606 of a polypeptide encoded by HEV ORF2" intends to comprise amino acid residues from positions 368 to 606 of a polypeptide encoded by D11092 and the corresponding fragments of the variants (natural or artificial) of a polypeptide encoded by D11092. The exemplary amino acid sequence of an HEV capsid protein (a polypeptide encoded by ORF2 of D11092) is described in SEQ ID NO: 31.

According to the invention, an influenza virus M2 protein refers to a protein encoded by the seventh segment of type A or type B influenza virus genome or a protein encoded by the sixth segment of type C influenza virus genome. The exemplary amino acid sequence of an influenza virus M2 protein is described in SEQ ID NO: 32.

According to the invention, the expression "corresponding sequence fragments" or "corresponding fragments" refers to fragments that are located in equal positions of sequences when the sequences are subjected to optimal alignment, namely, the sequences are aligned to obtain a highest percentage of identity.

According to the invention, when used in the background of proteins/polypeptides, the term "variant" refers to a protein, whose amino acid sequence is different from a reference protein/polypeptide (for example, CRM197 of the invention) by one or more (for example, 1-10, or 1-5 or 1-3) amino acids (such as conservative amino acid substitutions), or which has an identity of at least 60%, 80%, 85%, 90%, 95%, 96%, 97%, 98%, or 99% to a reference protein/polypeptide (for example, CRM197 of the invention), and which retains the essential characteristics of the reference protein/polypeptide. In the invention, the essential characteristics of CRM197 may refer to a strong immunogenicity and no cytotoxicity, and the essential characteristics of an HEV capsid protein and an influenza virus M2 protein may refer to antigenicity and/or immunogenicity thereof.

According to the invention, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used in the invention, the term "conservative substitution" refers to amino acid substitutions which would not negatively affect or change the essential characteristics of a protein/polypeptide comprising the amino acid sequence.

For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, with a residue similar to the corresponding amino acid residue physically or functionally (such as, having similar size, shape, charges, chemical properties including the capability of forming covalent bond or hydrogen bond, etc.). The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, an amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

According to the invention, the term "immunogenicity" refers to an ability of stimulating the formation of specific antibodies or sensitized lymphocytes in organisms. It not only refers to the property of an antigen to stimulate a specific immunocyte to activate, proliferate and differentiate the immunocyte so as to finally generate immunologic effector substance such as antibodies and sensitized lymphocytes, but also refers to the specific immune response wherein antibodies or sensitized T lymphocytes can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

According to the invention, the term "immunogenic fragment" refers to such a polypeptide fragment, which at least partially retains the immunogenicity of the protein from which it is derived. For example, immunogenic fragments of an HEV capsid protein refer to fragments of an HEV capsid protein which at least partially retain immunogenicity, for example, HEV-239, E2 or E2s as described in the invention (see, Li et al., J Biol Chem. 280(5): 3400-3406 (2005); Li et al., PLoS Pathogens. 5(8): e1000537 (2009)); immunogenic fragments of an influenza virus M2 protein refer to fragments of M2 protein which at least partially retain immunogenicity, for example, M2e as described in the invention (see, Fiers W et al., Vaccine. 27(45):6280-6283(2009)).

According to the invention, HEV-239 (or 239 in brief) refers to a polypeptide consisting of amino acid residues from positions 368 to 606 of a polypeptide encoded by HEV ORF2 (i.e. HEV capsid protein); E2 refers to a polypeptide consisting of amino acid residues from positions 394 to 606 of a polypeptide encoded by HEV ORF2; E2s refers to a polypeptide consisting of amino acid residues from positions 455 to 606 of a polypeptide encoded by HEV ORF2.

According to the invention, the term "M2e" refers to a polypeptide consisting of amino acid residues from positions 1 to 24 of an influenza virus M2 protein.

In the invention, the term "polypeptide" and "protein" have the same meanings and may be used interchangeably. Moreover, in the invention, amino acids are generally represented by one letter code and three-letter code well known in the art. For example, alanine may be represented by A or Ala.

According to the invention, the term "E. coli expression system" refers to an expression system consisting of E. coli (strain) and a vector, wherein the E. coli (strain) is available on the market, including but not limited to: GI698, ER2566, BL21 (DE3), B834 (DE3), BLR (DE3), etc.

According to the invention, the term "vector" refers to a nucleic acid vehicle which can have a polynucleotide inserted therein. When the vector allows for the expression of the protein encoded by the polynucleotide inserted therein, the vector is called an expression vector. The vector can be introduced into the host cell by transformation, transduction, or transfection, and have the carried genetic material elements expressed in a host cell. Vectors are well known by a person skilled in the art, including, but not limited to plasmids, phages, cosmids and the like.

According to the invention, the term "chromatography" includes, but is not limited to: ion exchange chromatography (e.g. cation-exchange chromatography), hydrophobic interaction chromatography, absorbent chromatography (e.g. hydroxyapatite chromatography), gel filtration chromatography (gel exclusion chromatography), and affinity chromatography.

According to the invention, the term "pharmaceutically acceptable carriers and/or excipients" refers to carriers and/or excipients that are pharmacologically and/or physiologically compatible with subjects and active ingredients, and are well known in the art (see, for example, Remington's Pharmaceutical Sciences. Edited by Gennaro A R, 19th ed. Pennsylvania: Mack Publishing Company, 1995), including, but not limited to pH adjusting agents, surfactants, adjuvants, and ionic strength enhancers. For example, pH adjusting agents include, but are not limited to, phosphate buffers; surfactants include, but are not limited to: anion surfactants, cation surfactants, or non-ionic surfactants (for example, Tween-80); and ionic strength enhancers include, but are not limited to sodium chloride.

According to the invention, the term "adjuvant" refers to a non-specific immuno-potentiator, which can enhance immune response to an antigen or change the type of immune response in an organism when it is delivered together with the antigen to the organism or is delivered to the organism in advance. There are a variety of adjuvants, including but limited to, aluminium adjuvants (for example, aluminum hydroxide), Freund's adjuvants (for example, Freund's complete adjuvant and Freund's incomplete adjuvant), *corynebacterium parvum*, lipopolysaccharide, cytokines, and the like. Freund's adjuvant is the most commonly used adjuvant in animal experiments currently. Aluminum hydroxide adjuvant is more commonly used in clinical trials.

According to the invention, the term "intramolecular adjuvant" refers to such an adjuvant, which forms a fusion protein with a target protein (i.e. an antigen), is present in the same molecule as the antigen (i.e. a fusion protein comprising it and the antigen), and acts as the adjuvant of the antigen to enhance immunogenicity of the antigen. Namely, an intramolecular adjuvant is an adjuvant capable of enhancing immunogenicity of a target protein (antigen) fused and expressed therewith, which generally refers to a polypeptide fragment. In the invention, an intramolecular adjuvant especially refers to a diphtheria toxin non-toxic mutant CRM197 or a fragment thereof.

The techniques for forming a fusion protein by fusion expression of two or more proteins are well known in the art (see, for example, Sambrook J et al., Molecular Cloning: A Laboratory Manual (Second Edition), Cold Spring Harbor Laboratory Press, 1989; and F. M. Ausubel et al., Short Protocols in Molecular Biology, 3rd Edition, John Wiley & Sons, Inc., 1995). Generally, DNA fragments encoding two or more proteins are linked together in frame by recombinant DNA techniques, and a fusion protein is obtained by protein expression. Optionally, a linker may be used or not in fusion expression of two or more proteins.

According to the invention, the term "linker" refers to a short peptide for linking two molecules (for example, proteins). Generally, a fusion protein, such as a target protein 1-linker-a target protein 2, is obtained by introduction (for example, by PCR amplification or ligase) of a polynucleotide encoding the short peptide between two DNA fragments encoding two target proteins to be linked, respectively, and protein expression thereof. As well known by a person skilled in the art, linkers include, but are not limited to flexible linking peptides, such as Gly-Gly-Gly-Gly (SEQ ID NO:57), Gly-Gly-Gly-Gly-Ser (SEQ ID NO:58), Gly-Gly-Ser-Ser (SEQ ID NO:59) and (Gly-Gly-Gly-Gly-Ser)$_3$ (SEQ ID NO:60).

According to the invention, the term "an effective amount" refers to an amount that is sufficient to achieve or at least partially achieve the expected effect. For example, an amount effective for preventing a disease (such as HEV or influenza virus infection) refers to an amount effective for preventing, suppressing, or delaying the occurrence of a disease (such as HEV or influenza virus infection). An effective amount for treating a disease refers to an amount effective for curing or at least partially blocking a disease and its complication in a patient with the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

The invention is at least partially based on the inventors' surprising discovery: after fusion expression of CRM197 or a fragment thereof with a target protein (for example, an HEV capsid protein, an influenza virus M2 protein or an immunogenic fragment thereof), CRM197 or a fragment thereof significantly enhances immunogenicity of the target protein. Namely, CRM197 or a fragment thereof may be used as intramolecular adjuvant for enhancing immunogenicity of a target protein by fusion expression with the target protein.

Therefore, in one aspect, the invention relates to a fusion protein comprising CRM197 or a fragment thereof and a target protein, wherein said CRM197 or a fragment thereof enhances immunogenicity of the target protein.

In a preferred embodiment, the fragment of CRM197 comprises, for example, Catalytic Domain C (aa 1-190, also called Fragment A in the present application), Transmembrane Domain T (aa 201-384), and/or Receptor Binding domain R (aa 386-535) of CRM197. For example, the fragment of CRM197 may comprise Fragment A, or Fragment A and Transmembrane Domain T.

In another preferred embodiment, the fragment of CRM197 comprises aa 1-190 of CRM197, for example, comprises aa 1-389 of CRM197. In another preferred embodiment, the fragment of CRM197 consists of aa 1-190 or aa 1-389 of CRM197. In the present application, the exemplary amino acid sequence of CRM197 is set forth in SEQ ID NO: 2, and the corresponding nucleotide sequence is set forth in SEQ ID NO:1.

In a preferred embodiment, the target protein may be an HEV capsid protein, an influenza virus M2 protein, or an immunogenic fragment thereof. In another preferred embodiment, the immunogenic fragment of an HEV capsid protein may comprise or be, for example, HEV-239 (aa 368-606 of the HEV capsid protein), E2 (aa 394-606 of the HEV capsid protein) or E2s (aa 455-606 of the HEV capsid protein), and the like. In another preferred embodiment, the immunogenic fragment of a M2 protein may comprise or be, for example, M2e (aa 1-24 of the M2 protein).

In a preferred embodiment, in the fusion protein of the invention, CRM197 or a fragment thereof may be linked to the N-terminus and/or C-terminus of the target protein, optionally via a linker. The linker for linking two peptide fragments are well known in the art, including but not limited to flexible linking peptides, such as Gly-Gly-Gly-Gly (SEQ ID NO:57), Gly-Gly-Gly-Gly-Ser (SEQ ID NO:58), Gly-Gly-Ser-Ser (SEQ ID NO:59) and (Gly-Gly-Gly-Gly-Ser)$_3$ (SEQ ID NO:60), etc. Such linkers are well known in the art, and the selection thereof is within the ability of a person skilled in the art.

In a preferred embodiment, the fusion protein of the invention may comprise CRM197 or a fragment thereof, and a HEV capsid protein or an immunogenic fragment thereof, which are linked together, optionally via a linker. For example, the fusion protein of the invention may be a protein having an amino acid sequence set forth in SEQ ID NO: 4, 6, 8, 10, 12, 14, 16 or 18.

In a preferred embodiment, the fusion protein of the invention may comprise CRM197 or a fragment thereof, and an influenza virus M2 protein or an immunogenic fragment thereof, which are linked together, optionally via a linker. For example, the fusion protein of the invention may be a protein having an amino acid sequence set forth in SEQ ID NO:34, 36, 38, 40, 42 or 44.

In the fusion protein of the invention, CRM197 or a fragment thereof surprisingly enhances immunogenicity of a target protein (such as HEV capsid protein, an influenza virus M2 protein or an immunogenic fragment thereof) fused thereto (optionally via a linker) significantly, and thus may be used as intramolecular adjuvant.

In another aspect, the invention provides a polynucleotide encoding the fusion protein as defined above, and also provides a construct comprising the polynucleotide.

In another aspect, the invention provides a vector comprising: a polynucleotide encoding the fusion protein as defined above or a construct comprising the polynucleotide. The vector of the invention may be a cloning vector, or an expression vector.

In a preferred embodiment, the vector of the invention may be, for example, plasmid, cosmid, phage, and the like.

In another aspect, the invention provides a host cell or organism comprising the polynucleotide, the construct, or the vector of the invention. Said host cell includes, but is not limited to, prokaryotic cell such as E. coli cell, and eukaryotic cell such as yeast cell, insect cell, plant cell and animal cell (such as mammalian cell, for example mice cell, human cell and the like). The cell of the invention may be a cell line, such as 293T cell. In an embodiment, the organism is plant or animal.

In another aspect, the invention also relates to a pharmaceutical composition or vaccine comprising the fusion protein of the invention, and optionally a pharmaceutically acceptable carrier and/or excipient. Depending on the target protein used in the fusion protein, the pharmaceutical composition or vaccine of the invention may be useful for the prevention and/or treatment of various diseases (i.e. diseases that can be prevented or treated by the target protein). For example, when the target protein used is an HEV capsid protein or an immunogenic fragment thereof, the pharmaceutical composition of the invention may be used to prevent and/or treat HEV infection and diseases associated with HEV infection such as Hepatitis E; when the target protein used is an influenza virus M2 protein or an immunogenic fragment thereof, the pharmaceutical composition of the invention may be used to prevent and/or treat influenza virus infection and diseases associated with influenza virus infection such as influenza.

In another aspect, the invention also relates to a use of the fusion protein of the invention in the manufacture of a pharmaceutical composition for the prevention and/or treatment of diseases that can be prevented or treated by the target protein. Depending on the target protein used in the fusion protein, the pharmaceutical composition of the invention may be used to prevent and/or treat various diseases. For example, when the target protein used is an HEV capsid protein or an immunogenic fragment thereof, the pharmaceutical composition of the invention may be used to prevent and/or treat HEV infection and diseases associated with HEV infection such as Hepatitis E; when the target protein used is an influenza virus M2 protein or an immunogenic fragment thereof, the pharmaceutical composition of the invention may be used to prevent and/or treat influenza virus infection and diseases associated with influenza virus infection such as influenza.

In another aspect, the invention also relates to a method for preventing and/or treating HEV infection and/or diseases associated with HEV infection such as Hepatitis E, comprising administering an effective amount of the fusion protein of the invention or the pharmaceutical composition comprising the fusion protein, wherein the fusion protein comprises CRM197 or a fragment thereof and an HEV capsid protein or an immunogenic fragment thereof, which are linked together, optionally via a linker.

In another aspect, the invention also relates to a method for preventing and/or treating influenza virus infection and diseases associated with influenza virus infection such as influenza, comprising administering an effective amount of the fusion protein of the invention or the pharmaceutical composition comprising the fusion protein, wherein the fusion protein comprises CRM197 or a fragment thereof and an influenza virus M2 protein or an immunogenic fragment thereof, which are linked together, optionally via a linker.

In another aspect, the invention provides a method for enhancing immunogenicity of a target protein, comprising obtaining a fusion protein comprising CRM197 or a fragment thereof as defined above and the target protein, so as to enhance immunogenicity of the target protein.

In a preferred embodiment, the fusion protein may be obtained by fusion expression of CRM197 or a fragment thereof with the target protein, optionally using a linker. In a preferred embodiment, the target protein is the HEV capsid protein, the influenza virus M2 protein or an immunogenic fragment thereof as described above.

Therefore, in an embodiment, the invention provides a method for enhancing immunogenicity of an HEV capsid protein or an immunogenic fragment thereof, comprising obtaining a fusion protein comprising CRM197 or a fragment thereof and an HEV capsid protein or an immunogenic fragment thereof, so as to enhance immunogenicity of the HEV capsid protein or an immunogenic fragment thereof. In a preferred embodiment, the fusion protein may be obtained by fusion expression of CRM197 or a fragment thereof with an HEV capsid protein or an immunogenic fragment thereof, optionally using a linker.

In another embodiment, the invention provides a method for enhancing immunogenicity of an influenza virus M2 protein or an immunogenic fragment thereof, comprising obtaining a fusion protein comprising CRM197 or a fragment thereof and an influenza virus M2 protein or an immunogenic fragment thereof, so as to enhance immunogenicity of the influenza virus M2 protein or an immunogenic fragment thereof. In a preferred embodiment, the fusion protein may be obtained by fusion expression of CRM197 or a fragment thereof with an influenza virus M2 protein or an immunogenic fragment thereof, optionally using a linker.

In another aspect, the invention relates to a use of CRM197 or a fragment thereof in the enhancement of immunogenicity of a target protein, characterized by obtaining a fusion protein comprising CRM197 or a fragment thereof and the target protein.

In a preferred embodiment, the fusion protein may be obtained by fusion expression of CRM197 or a fragment thereof with the target protein, optionally using a linker. In a preferred embodiment, the target protein is an HEV capsid protein, an influenza virus M2 protein, or an immunogenic fragment thereof.

Therefore, in an embodiment, the invention relates to a use of CRM197 or a fragment thereof in the enhancement of immunogenicity of an HEV capsid protein or an immunogenic fragment thereof, characterized by obtaining a fusion protein comprising CRM197 or a fragment thereof and the HEV capsid protein or an immunogenic fragment thereof. In a preferred embodiment, the fusion protein may be obtained by fusion expression of CRM197 or a fragment thereof with the HEV capsid protein or an immunogenic fragment thereof, optionally using a linker.

In another embodiment, the invention relates to a use of CRM197 or a fragment thereof in the enhancement of immunogenicity of an influenza virus M2 protein or an immunogenic fragment thereof, characterized by obtaining a fusion protein comprising CRM197 or a fragment thereof and the influenza virus M2 protein or an immunogenic fragment thereof. In a preferred embodiment, the fusion protein may be obtained by fusion expression of CRM197 or a fragment thereof with the influenza virus M2 protein or an immunogenic fragment thereof, optionally using a linker.

Beneficial Effect of the Invention

The invention demonstrates for the first time that CRM197 and fragments thereof may be used as intramolecular adjuvant for enhancing immunogenicity of a target protein. Therefore, the invention provides a novel use of CRM197 and fragments thereof, and provides a novel method for enhancing immunogenicity of a target protein.

In addition, since the fusion protein of the invention exhibits a stronger immunogenicity as compared to a target protein alone, the invention provides a new option for the manufacture of a medicament or vaccine and may achieve more effective treatment and prevention of the corresponding diseases.

For example, the fusion protein of the invention comprising CRM197 (or a fragment thereof) and an HEV capsid protein (or an immunogenic fragment thereof) exhibits a stronger immunogenicity as compared to a HEV capsid protein (or an immunogenic fragment thereof) alone, and therefore the fusion protein may be useful for the manufacture of a pharmaceutical composition and more effectively prevent and treat HEV infection and diseases associated with HEV infection such as Hepatitis E.

For example, the fusion protein of the invention comprising CRM197 (or a fragment thereof) and an influenza virus M2 protein (or an immunogenic fragment thereof) exhibits a stronger immunogenicity as compared to a influenza virus M2 protein (or an immunogenic fragment thereof) alone, and therefore the fusion protein may be useful for the manufacture of a pharmaceutical composition and more effectively prevent and treat influenza virus infection and diseases associated with influenza virus infection such as influenza. For example, when M2e protein is fused to the N-terminal of CRM197 (or a fragment thereof), the fusion protein thus formed may form a tetramer or other polymer configuration, and has a good reactivity with a protective monoclonal antibody 019 (see, Fu et al., Virology, 2009, 385:218-226) in vitro (see, FIG. 12B), and has a good immunogenicity in vivo (see, FIG. 14). Therefore, the fusion protein thus formed is useful for developing general influenza vaccines.

Description of Sequence Information

The information of the sequences as involved in the invention is provided in the following table.

| SEQ ID NO: | Depiction | SEQ ID NO: | Depiction |
|---|---|---|---|
| 1 | the nucleotide sequence of CRM197 | 2 | the amino acid sequence of CRM197 |
| 3 | the nucleotide sequence of CRM197-L-E2 | 4 | the amino acid sequence of CRM197-L-E2 |
| 5 | the nucleotide sequence of CRM197-L-E2s | 6 | the amino acid sequence of CRM197-L-E2s |
| 7 | the nucleotide sequence of 389-L-E2 | 8 | the amino acid sequence of 389-L-E2 |
| 9 | the nucleotide sequence of 389-L-E2s | 10 | the amino acid sequence of 389-L-E2s |
| 11 | the nucleotide sequence of A-L-E2 | 12 | the amino acid sequence of A-L-E2 |
| 13 | the nucleotide sequence of A-L-E2s | 14 | the amino acid sequence of A-L-E2s |
| 15 | the nucleotide sequence of 389-E2s | 16 | the amino acid sequence of 389-E2s |
| 17 | the nucleotide sequence of A-E2s | 18 | the amino acid sequence of A-E2s |
| 19 | primer CRM197F | 20 | primer CRM197R |
| 21 | primer CRM197-linker R | 22 | primer 389-linker R |
| 23 | primer A-linker R | 24 | primer E2F |
| 25 | primer E2sF | 26 | primer Drp59R |
| 27 | primer 389-E2s R | 28 | primer A-E2s R |
| 29 | primer 389-E2s F | 30 | primer A-E2s F |
| 31 | the amino acid sequence of HEV capsid protein | 32 | the amino acid sequence of M2 protein |
| 33 | the nucleotide sequence of CRM197-L-M2e | 34 | the amino acid sequence of CRM197-L-M2e |
| 35 | the nucleotide sequence of 389-L-M2e | 36 | the amino acid sequence of 389-L-M2e |
| 37 | the nucleotide sequence of A-L-M2e | 38 | the amino acid sequence of A-L-M2e |
| 39 | the nucleotide sequence of M2e-L-CRM197 | 40 | the amino acid sequence of M2e-L-CRM197 |
| 41 | the nucleotide sequence of M2e-L-389 | 42 | the amino acid sequence of M2e-L-389 |
| 43 | the nucleotide sequence of M2e-L-A | 44 | the amino acid sequence of M2e-L-A |
| 45 | primer CRM197F1 | 46 | primer CRM197-linker R1 |
| 47 | primer 389-linker R1 | 48 | primer A-linker R1 |
| 49 | primer M2eF1 | 50 | primer M2eR |
| 51 | primer M2eF2 | 52 | primer M2e-Linker R |
| 53 | primer CRM197F2 | 54 | primer CRM197 R2 |
| 55 | primer 389 R | 56 | primer A R |

The embodiments of the invention are further described in detail by reference to the drawings and examples. However, a person skilled in the art would understand that the following drawings and examples are intended for illustrating the invention only, rather than defining the scope of the invention. According to the detailed depiction of the following drawings and preferred embodiments, various purposes and advantages of the invention would be obvious for a person skilled in the art.

DESCRIPTION OF THE DRAWINGS

FIG. 5A shows the ELISA result of the fusion proteins comprising E2, and FIG. 5B shows the ELISA result of the fusion proteins comprising E2s. The results showed that the reactivity of E2s protein with HEV-specific monoclonal antibody was significantly enhanced, after fusion of E2s protein with CRM197 or a fragment thereof, wherein the reactivity of A-L-E2s and A-E2S was enhanced most significantly; the reactivity of E2 protein with HEV-specific monoclonal antibody was retained or enhanced, after fusion of E2 protein with CRM197 or a fragment thereof.

The results shown in FIGS. 10A-10F indicated that all the constructed fusion proteins could be expressed in inclusion bodies, and after purification and renaturation, the fusion proteins with a purity of about 80% could be obtained.

FIGS. 11A-11H show the results of Western blotting using the fusion proteins constructed in Example 6 and anti-M2e monoclonal antibody 5D1 and CRM197 monoclonal antibody 1E6. The samples represented by Lanes 1-6 in FIGS. 11A, 11B, 11C and 11D correspond to the samples represented by Lanes 1-6 in FIGS. 10C, 10D, 10E and 10F, respectively, wherein anti-M2e specific monoclonal antibody 5D1 was used. The samples represented by Lanes 1-6 in FIGS. 11E, 11F, 11G and 11H correspond to the samples represented by Lanes 1-6 in FIGS. 10C, 10D, 10E and 10F, respectively, wherein CRM197 specific monoclonal antibody 1E6 was used. The results showed that all the tested fusion proteins had significant reactivity with anti-M2e specific monoclonal antibody 5D1 and CRM197 specific monoclonal antibody 1E6.

Figure 12A:
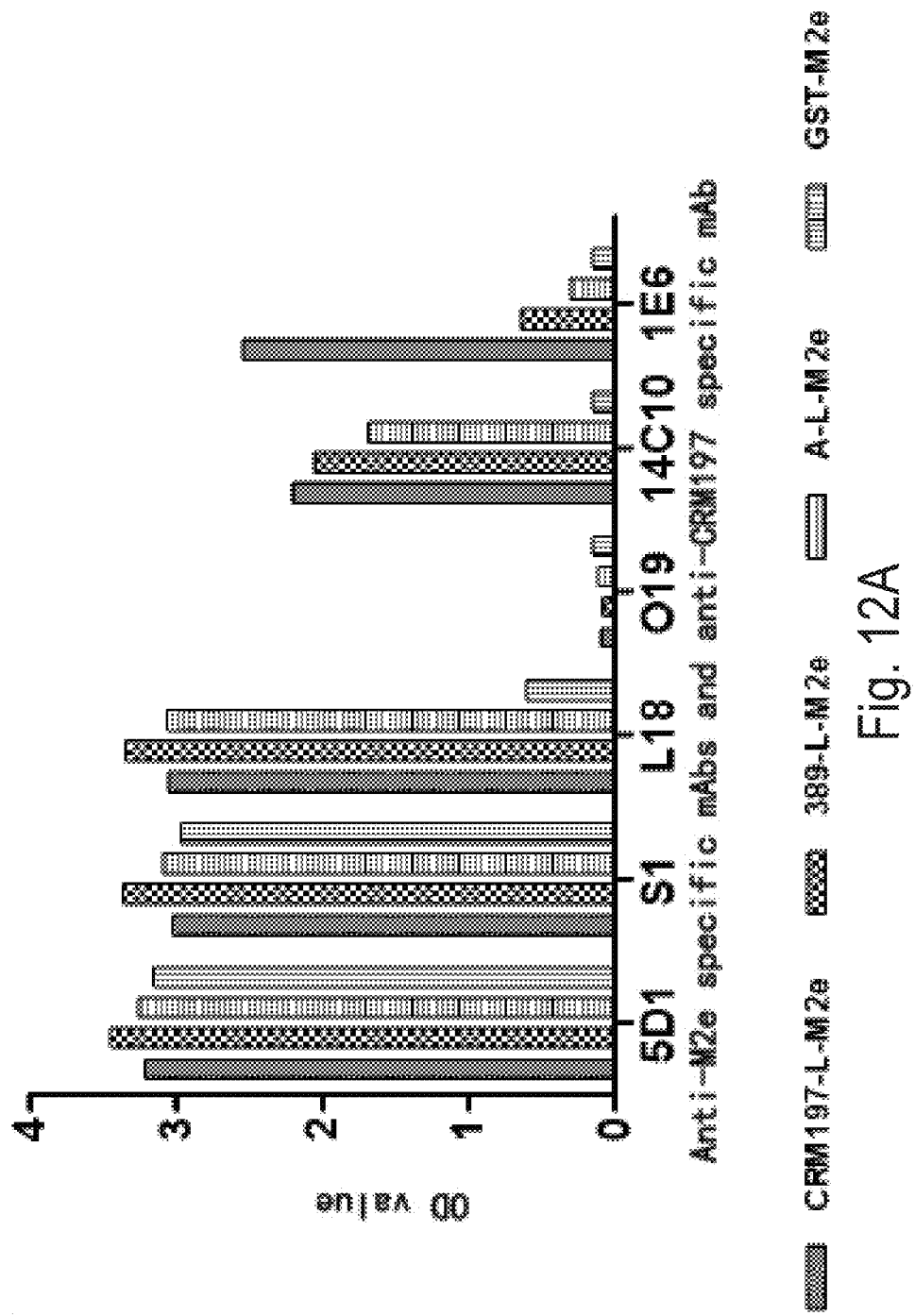
Figure 12B:
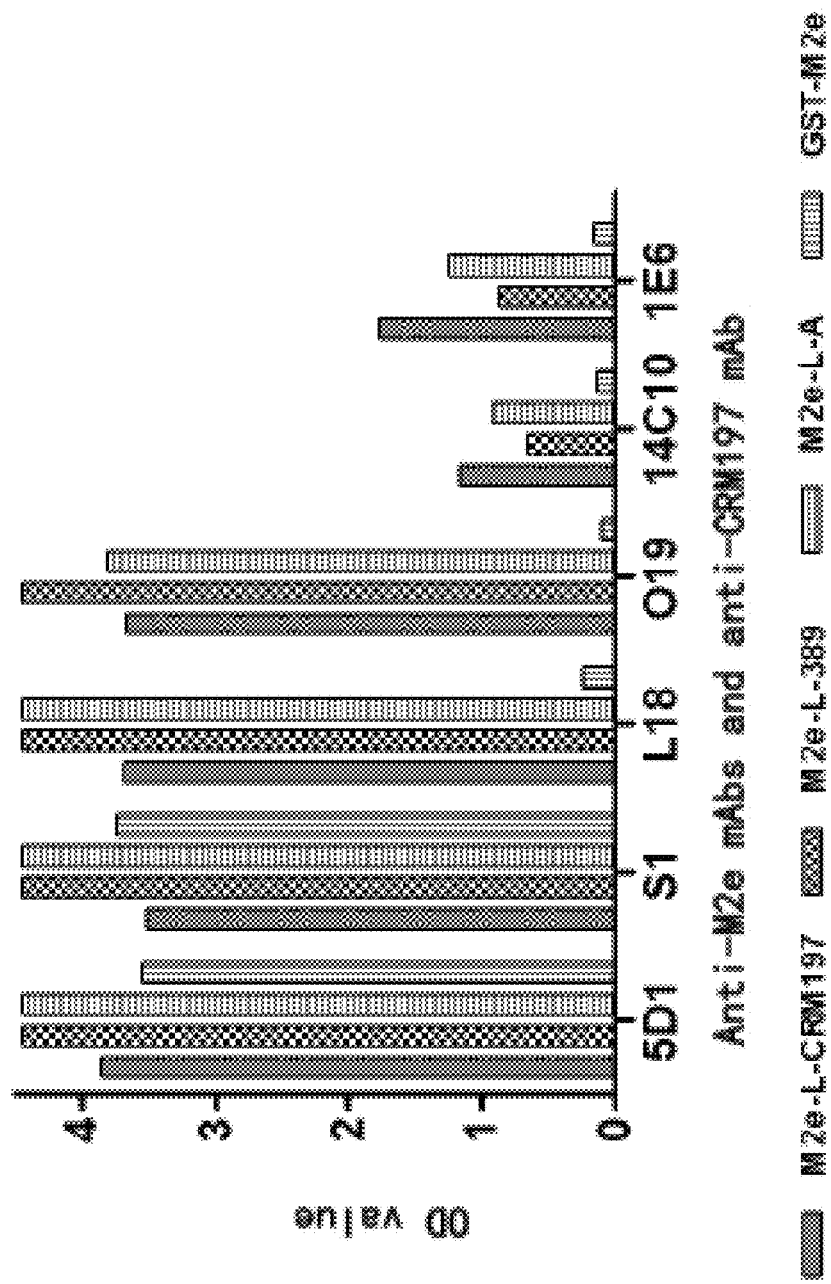

FIGS. 12A-12B show the results of indirect ELISA using the fusion proteins constructed in Example 6 and various anti-M2e specific monoclonal antibodies. The abscissa refers to anti-M2e specific monoclonal antibodies and anti-CRM197 specific monoclonal antibodies for ELISA, and the ordinate refers to OD value determined by ELISA at the same antibody dilution. FIG. 12A shows the ELISA result of the fusion protein in which M2e was fused to the C-terminus of CRM197 or a fragment thereof, and FIG. 12B shows the ELISA result of the fusion protein in which M2e was fused to the N-terminus of CRM197 or a fragment thereof. The results showed that the fusion protein comprising M2e protein and CRM197 or a fragment thereof retained or enhanced the reactivity with various anti-M2e specific monoclonal antibodies, as compared to M2e protein alone.

Figure 13A:
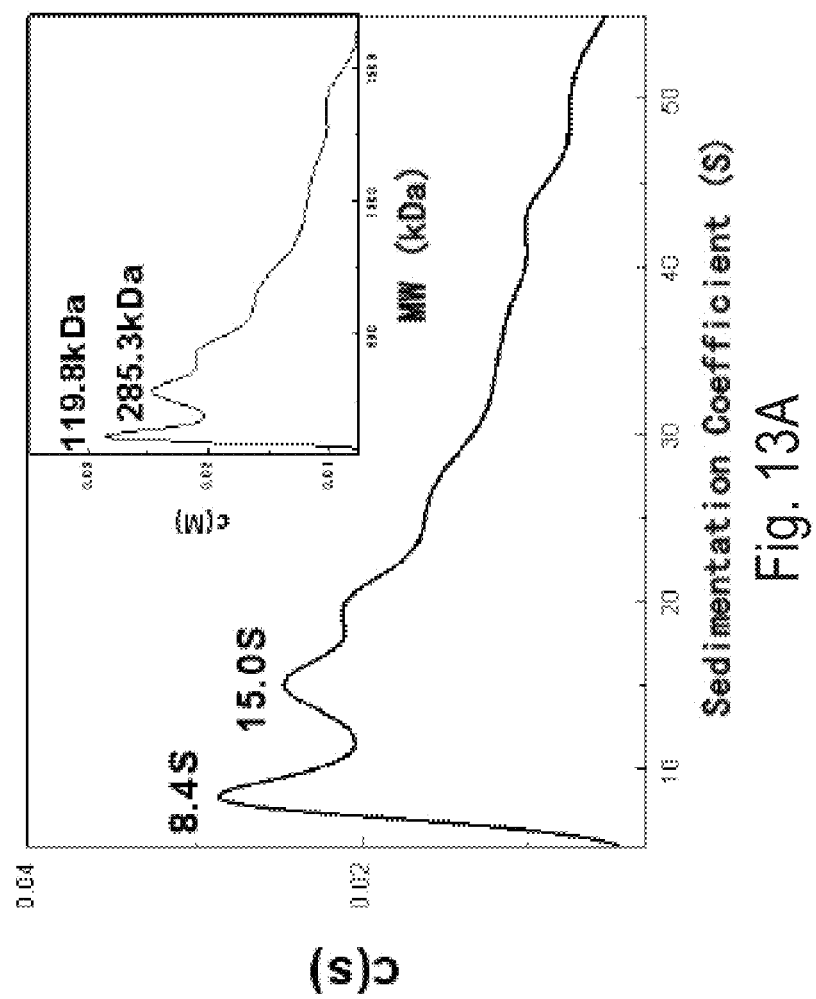
Figure 13B:
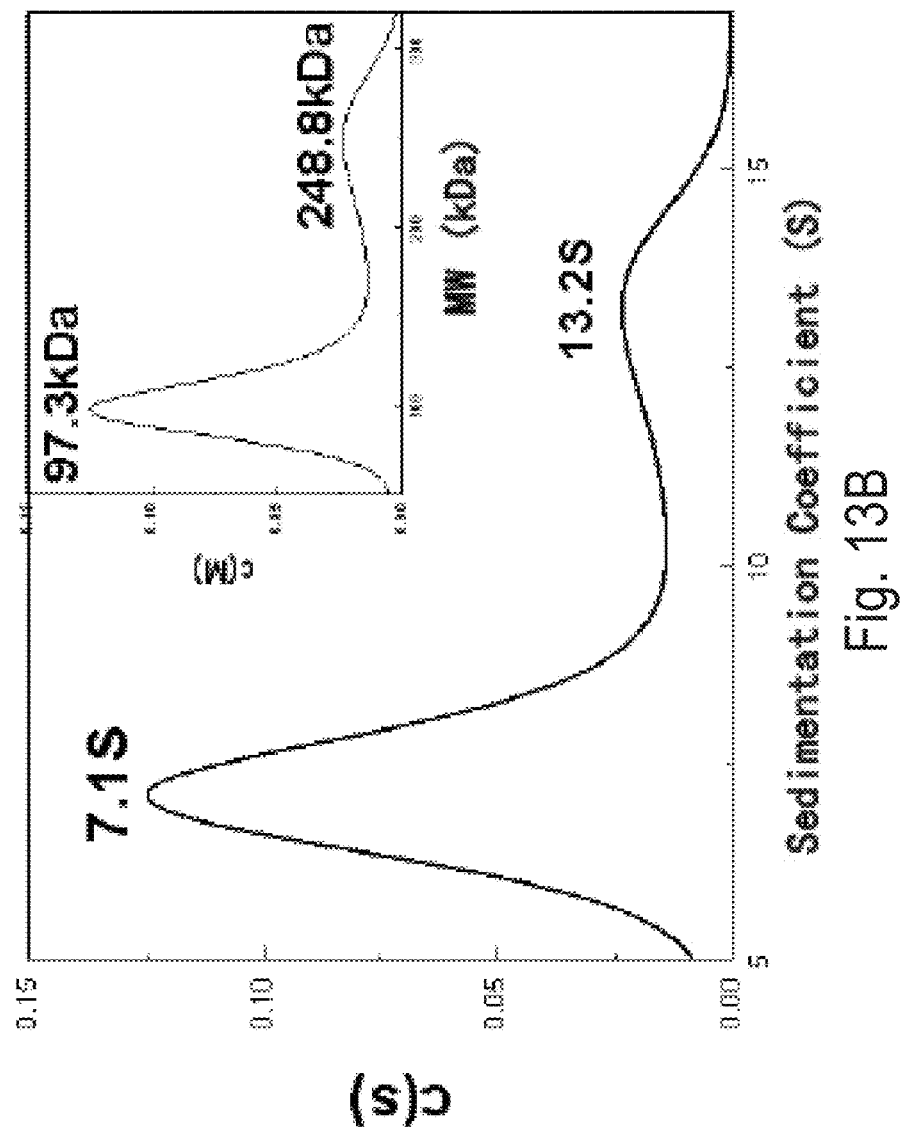
Figure 13D:
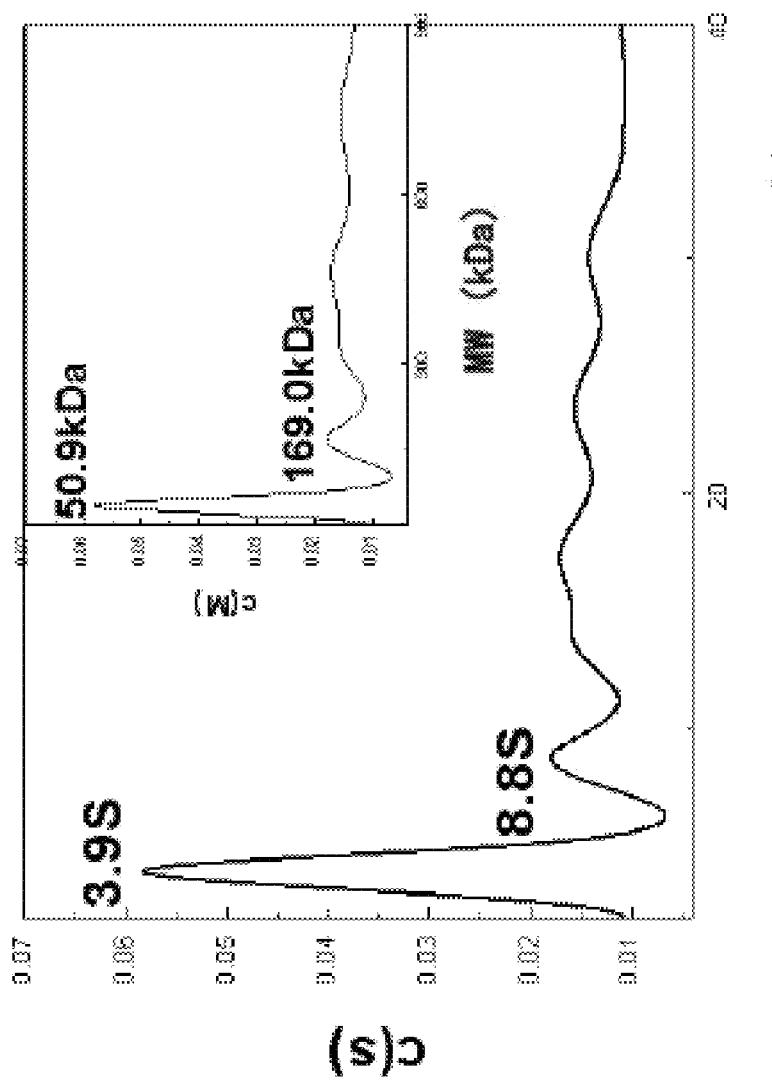
Figure 13E:
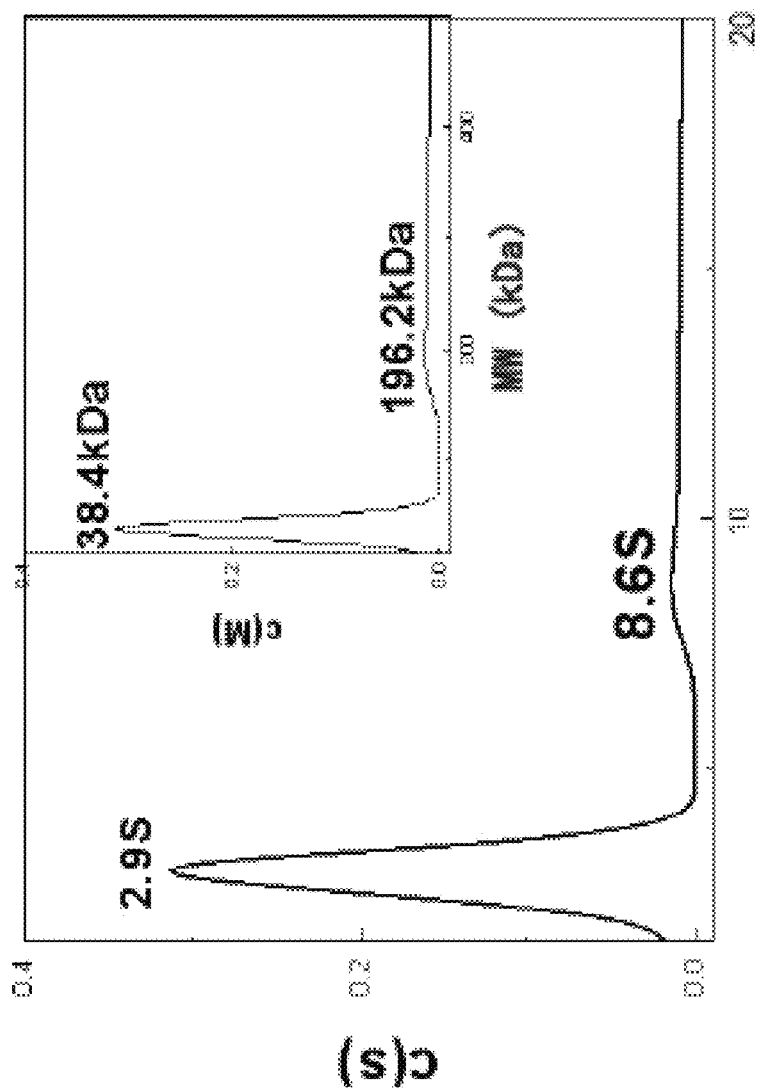
Figure 13F:
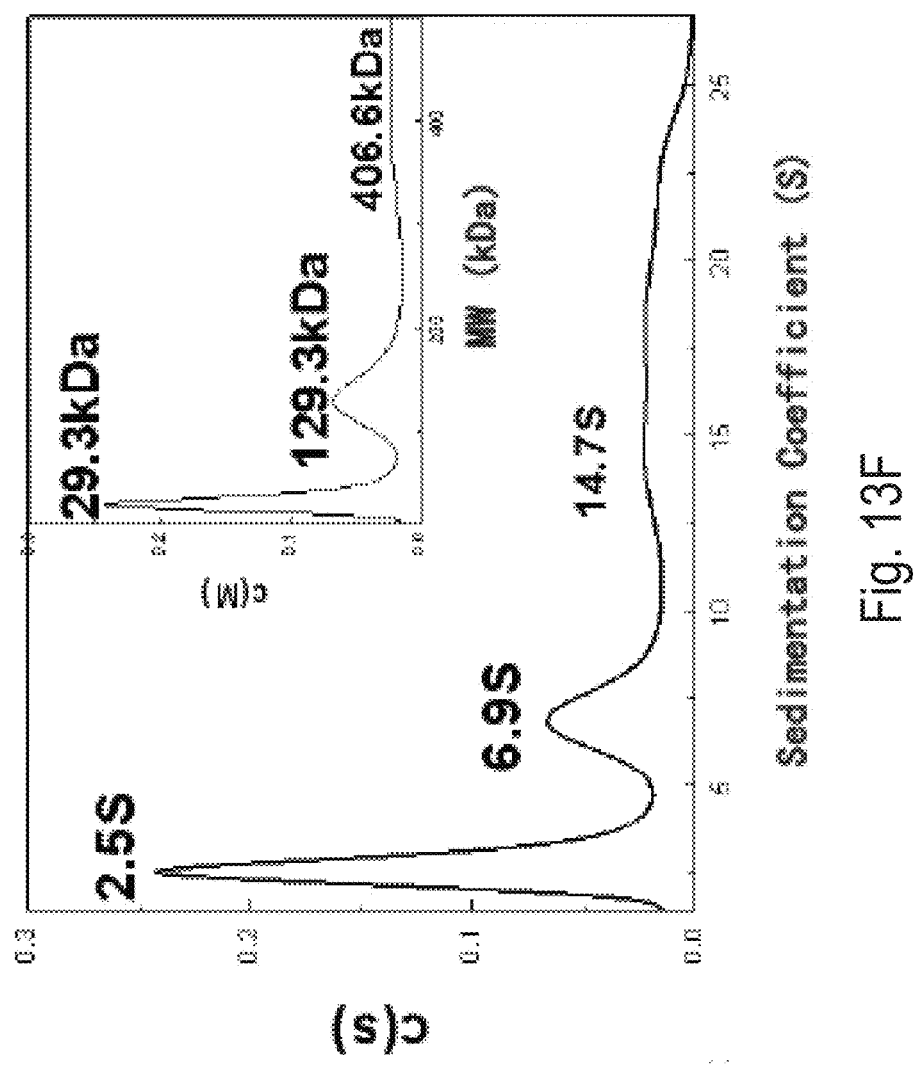

FIGS. 13A-13F show the analytic results of Sedimentation Velocity (SV) of the fusion proteins constructed in Example 6, wherein FIG. 13A: CRM197-L-M2e; FIG. 13B: 389-L-M2e; FIG. 13C: A-L-M2e; FIG. 13D: M2e-L-CRM197; FIG. 13E: M2e-L-389; FIG. 13F: M2e-L-A. The results showed that the fusion proteins A-L-M2e and M2e-L-A were mainly present in a form of monomer and tetramer; and 389-L-M2e was mainly present in a form of dimer and polymer; M2e-L-389 was mainly present in a form of monomer and polymer; CRM197-L-M2e was mainly present in a form of dimer and polymer; and M2e-L-CRM197 was mainly present in a form of monomer and polymer.

Figure 14A:
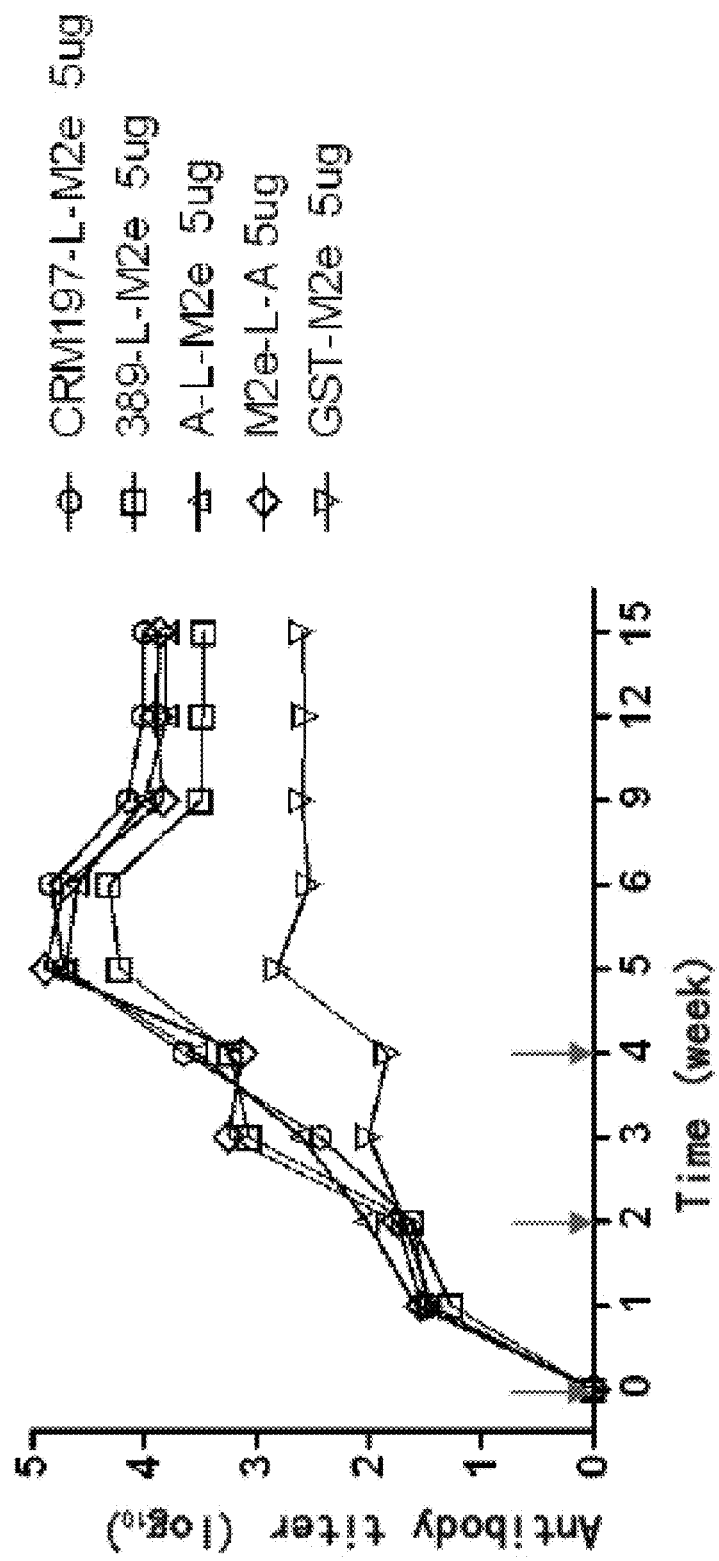
Figure 14B:
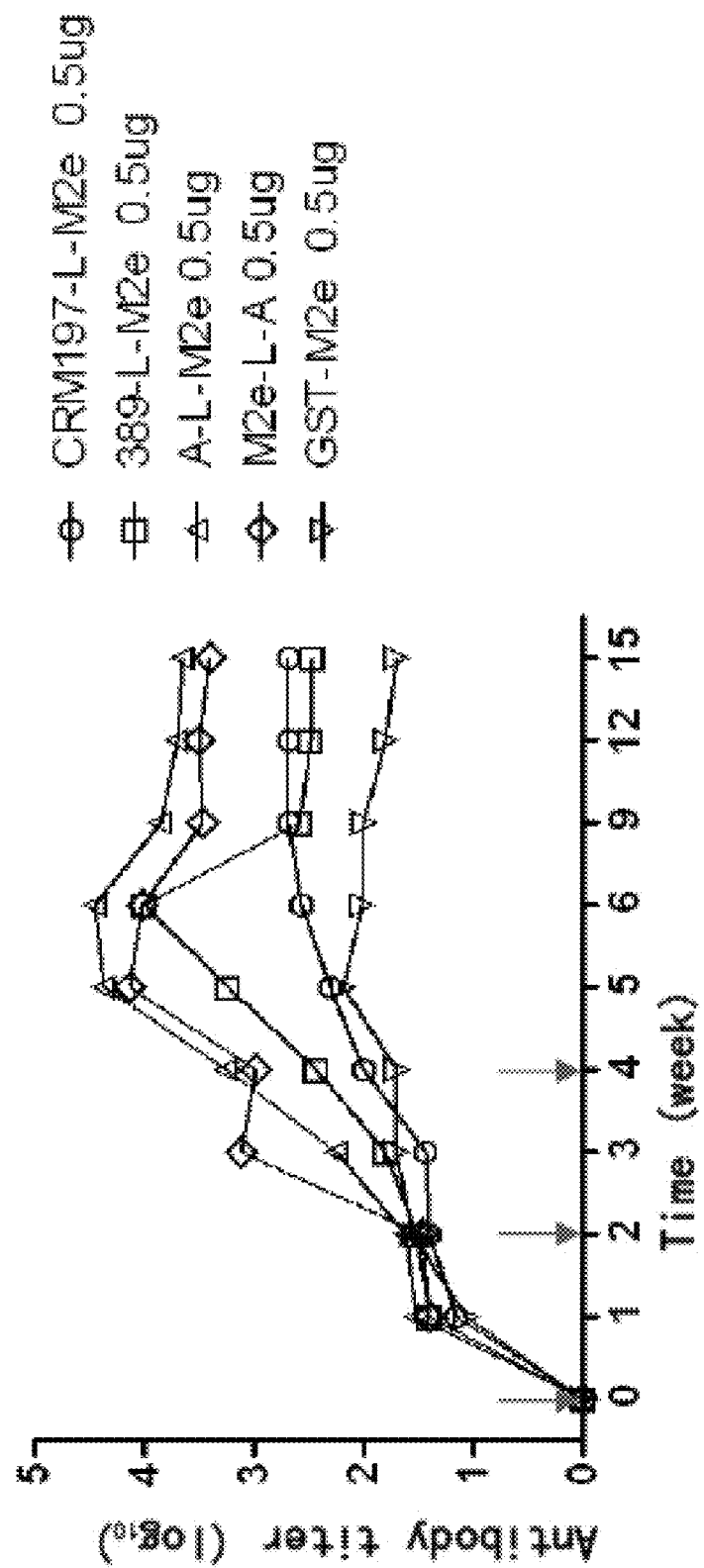

FIGS. 14A-14B show the comparison of immunogenicity between the fusion proteins constructed in Example 6 and GST-M2e. The primary immunization was performed at week 0, and booster immunization was performed at week 2 and 4, wherein the dose for both the primary immunization and the booster immunization was 5 μg or 0.5 μs. FIG. 14A shows the comparison result of the antibody titer of immune serum in 5 μg-dose groups, and FIG. 14B shows the comparison result of the antibody titer of immune serum in 0.5m-dose groups. The results showed that after the second booster immunization, the antibody titers induced by the fusion proteins were significantly higher than GST-M2e alone in 5 μg- and 0.5 μg-dose groups. As seen from the results above, the immunogenicity of the fusion proteins constructed in Example 6 were significantly higher than the antigen protein (GST-M2e) alone, indicating that the CRM197 of the invention or a fragment thereof (no matter located at N-terminus or C-terminus of the fusion protein) significantly enhanced immunogenicity of the antigen protein fused therewith, and could be used as intramolecular adjuvant.

SPECIFIC MODES FOR CARRYING OUT THE INVENTION

The present invention is illustrated by reference to the following examples (which are used only for the purpose of illustrating the present invention and are not intended to limit the protection scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction endonucleases are used under the conditions recommended by manufacturers of the products. The reagents used in the present invention, whose manufacturers are not clearly indicated, are conventional products in the art or commercially available. Those skilled in the art understand that the examples are used for illustrating the present invention, but not intended to limit the protection scope of the present invention.

Example 1. Clone of CRM197 Gene

Genomic DNA extracted from Diphtheria *bacillus* C7 ((3197) strain obtained from ATCC (NO 53281) was used as template for the PCR reaction, wherein the forward primer was CRM197F (SEQ ID NO: 19), and the reverse primer was CRM197R (SEQ ID NO: 20). The PCR reaction was performed in a PCR apparatus (Biometra T3) under the following conditions, to prepare the full-length gene encoding CRM197.

| | |
|---|---|
| 94° C. denaturation 10 min | 1 cycle |
| 94° C. denaturation 1.5 min | 20 cycles |
| 58° C. annealing 1.5 min | |
| 72° C. elongation 1.5 min | |
| 72° C. elongation 10 min | 1 cycle |

After PCR amplification, a product of about 1.6 kb in length, was obtained. After sequencing, the nucleotide sequence (SEQ ID NO: 1) of the amplification product (i.e. the full-length gene of CRM197) was obtained, and the amino acid sequence encoded thereby was set forth in SEQ ID NO: 2.

Figure 1:
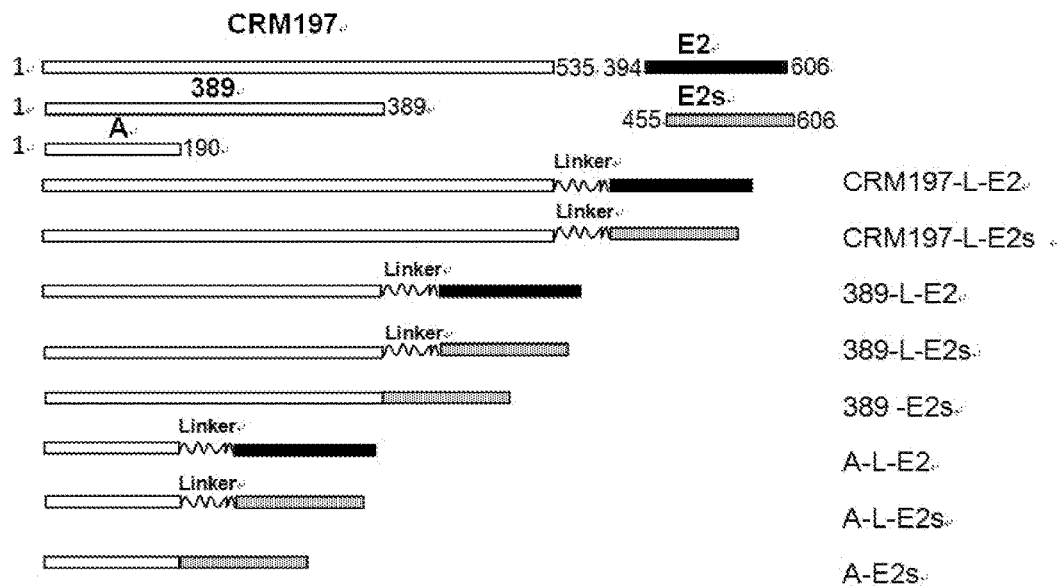
FIG. 1 shows the clone design of the fusion proteins constructed in Example 2, wherein the linker used (Linker, also referred to L for short in the present application) is a flexible fragment consisting of 15 amino acid residues, whose sequence is GGGGSGGGGSGGGGS (SEQ ID NO:60); the CRM197 used comprised 535 amino acids, whose sequence is set forth in SEQ ID NO: 2; 389 refers to a polypeptide comprising amino acid residues from positions 1 to 389 (aa 1-389) of CRM197; A refers to a polypeptide comprising amino acid residues from positions 1 to 190 (aa 1-190) of CRM197; E2 refers to a polypeptide comprising amino acid residues from positions 394 to 606 (aa 394-606) of an HEV capsid protein; E2s refers to a polypeptide comprising amino acid residues from positions 455 to 606 (aa 455-606) of an HEV capsid protein.
Figure 2A:
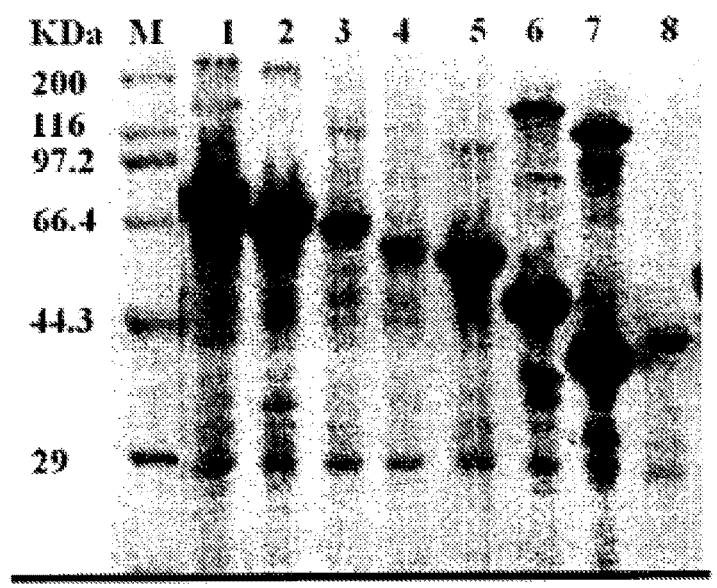
FIGS. 2A-2D show SDS-PAGE analytic results of expression, purification and renaturation of the fusion proteins constructed in Example 2, wherein the sample used in FIG. 2A is the precipitate (i.e. inclusion body) obtained by centrifuging the disrupted bacteria after ultrasonication, the sample used in FIG. 2B is a 4M urea dissolved supernatant, the sample used in FIG. 2C is a 8M urea dissolved supernatant, and the sample used in FIG. 2D is a protein renatured into PBS. Lane M: protein molecular weight marker; Lane 1: CRM197-L-E2; Lane 2: CRM197-L-E2s; Lane 3: 389-L-E2; Lane 4: 389-L-E2s; Lane 5: 389-E2s; Lane 6: A-L-E2; Lane 7: A-L-E2s; Lane 8: A-E2s. The results showed that all the constructed fusion proteins could be expressed in inclusion bodies, and A-L-E2 and A-L-E2s were dissolved in 4M and 8M urea, while other fusion proteins were only dissolved in 8M urea. In addition, the results also showed that after dialysis and renaturation, the fusion proteins of a purity of about 80% were obtained.
Figure 2B:
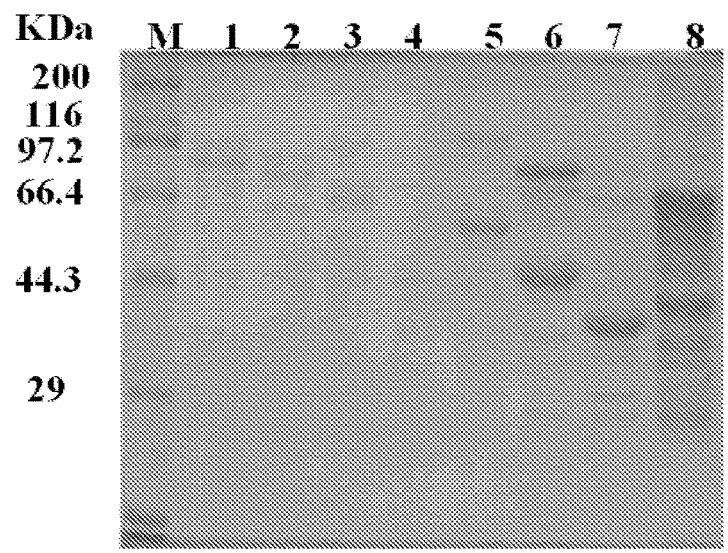
Figure 2C:
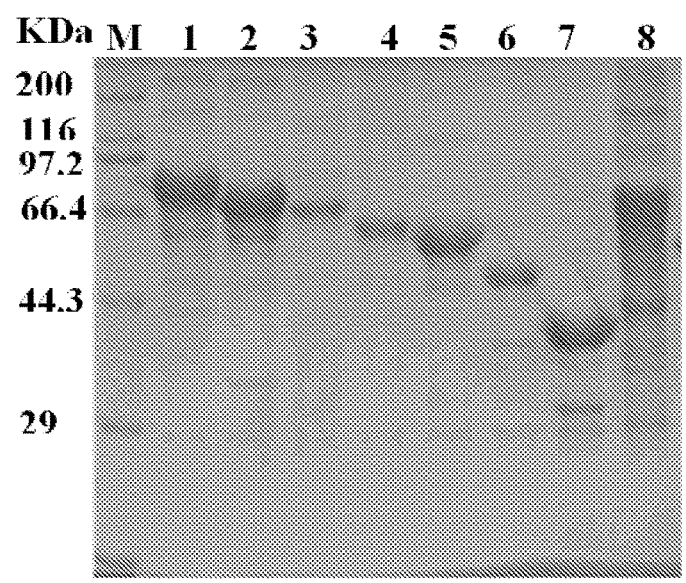
Figure 2D:
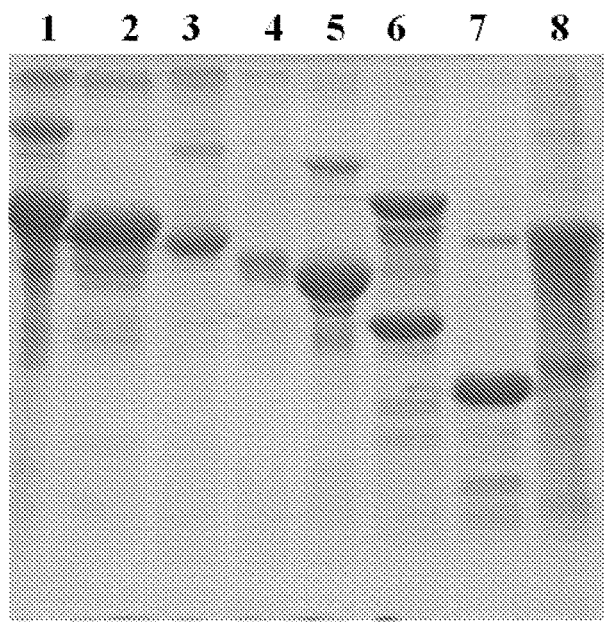

Example 2. Design and Clone of Fusion Proteins Comprising CRM197 or a Fragment Thereof and an HEV Capsid Protein Fragment In the Example, vectors expressing the fusion proteins were constructed exemplarily. The clone design of various exemplary fusion proteins constructed is shown in FIG. 1, wherein the fusion proteins each comprise CRM197 or a fragment thereof and an HEV capsid protein fragment, optionally using a linker.

Clone of Fusion Proteins Comprising a Linker

The amplification product (i.e. the full-length gene of CRM197) obtained in the Example 1 was used as template. The forward primer was CRM197F (SEQ ID NO: 19), at the 5' terminal of which the restriction endonuclease NdeI site CAT ATG was introduced, wherein ATG was the initiation codon in E. coli system. The reverse primers were CRM197-linker R (SEQ ID NO: 21), 389-linker R (SEQ ID NO: 22), and A-linker R (SEQ ID NO: 23), respectively, at the 5' terminal of which the restriction endonuclease BamHI site GGA TCC was introduced. The PCR reaction was performed in a PCR thermocycler (Biometra T3) under the following conditions. The sequences of the primers used were shown in Table 1.

| 94° C. denaturation 10 min | 1 cycle |
|---|---|
| 94° C. denaturation 1.5 min | 20 cycle |
| 58° C. annealing 1.5 min | |
| 72° C. elongation 1.5 min | |
| 72° C. elongation 10 min | 1 cycle |

The amplification products were DNA fragments of about 1600 bp, 1200 bp and 600 bp in length, respectively.

In addition, pTO-T7-E2 (Li, et al. JBC. 2005. 28(5): 3400-3406) was used as template. The forward primers were E2F (SEQ ID NO: 24) and E2sF (SEQ ID NO: 25), respectively, at the 5' terminal of which the restriction endonuclease BamHI site GGA TCC was introduced. The reverse primer was Drp59R (SEQ ID NO: 26), at the 5' terminal of which the restriction endonuclease EcoRI site GAA TTC was introduced. The PCR reaction was performed in a PCR thermocycler (Biometra T3) under the following conditions.

| 94° C. denaturation 10 min | 1 cycle |
|---|---|
| 94° C. denaturation 50 sec | 20 cycle |
| 58° C. annealing 50 sec | |
| 72° C. elongation 50 sec | |
| 72° C. elongation 10 min | 1 cycle |

The amplification products were DNA fragments of about 600 bp and 450 bp in length, respectively.

The amplification products as obtained above were linked into commercially available pMD 18-T vector (produced by TAKARA Co.), respectively, and designated as pMD 18-T-CRM197-L, pMD 18-T-389-L and pMD 18-T-A-L as well as pMD 18-T-E2 and pMD 18-T-E2s. As identified by NdeI/BamHI and BamHI/EcoRI enzyme cleavage, respectively, the positive clones pMD 18-T-CRM197-L, pMD 18-T-389-L, pMD 18-T-A-L, pMD 18-T-E2 and pMD 18-T-E2s were obtained.

As confirmed by M13(+) primer, correct nucleotide sequences of interest were inserted into the obtained pMD 18-T-CRM197-L, pMD 18-T-389-L, pMD 18-T-A-L, pMD 18-T-E2 and pMD 18-T-E2s, respectively.

The plasmids pMD 18-T-CRM197-L, pMD 18-T-389-L and pMD 18-T-A-L were digested by NdeI/BamHI enzyme. The fragments obtained by enzyme cleavage were linked into the prokaryotic expression vector pTO-T7 digested by NdeI/BamHI enzyme (Luo Wenxin et al., Chinese Journal of Biotechnology, 2000, 16:53-57), and were transformed into E. coli ER2566 (purchased from Invitrogen Co.); after extraction of plasmids, as identified by NdeI/BamHI enzyme cleavage, the positive plasmids pTO-T7-CRM197-L, pTO-T7-389-L and pTO-T7-A-L, into which CRM197-L, 389-L and A-L were inserted, respectively, were obtained.

pTO-T7-CRM197-L, pTO-T7-389-L, pTO-T7-A-L, pMD 18-T-E2 and pMD 18-T-E2s were digested by BamHI/EcoRI enzyme. Each of the obtained E2 and E2s fragments was linked into the vectors pTO-T7-CRM197-L, pTO-T7-389-L and pTO-T7-A-L digested by BamHI/EcoRI enzyme, respectively. As identified by NdeI/EcoRI enzyme cleavage, the positive expression vectors pTO-T7-CRM197-L-E2, pTO-T7-CRM197-L-E2s, pTO-T7-389-L-E2, pTO-T7-389-L-E2s, pTO-T7-A-L-E2 and pTO-T7-A-L-E2s, into which CRM197-L-E2 (SEQ ID NO:3, 4), CRM197-L-E2s (SEQ ID NO:5, 6), 389-L-E2 (SEQ ID NO:7, 8), 389-L-E2s (SEQ ID NO:9, 10), A-L-E2 (SEQ ID NO:11, 12) or A-L-E2s (SEQ ID NO:13, 14) was inserted, respectively, were obtained.

Clone of the Fusion Proteins 389-E2s and A-E2s without a Linker

The vectors expressing 389-E2s and A-E2s were constructed by three PCR reactions. For the first PCR reaction, the full-length gene of CRM197 was used as template. The forward primer was CRM197F, at the 5' terminal of which the restriction endonuclease NdeI site CAT ATG was introduced, wherein ATG was the initiation codon in E. coli system. The reverse primers were 389-E2s R (SEQ ID NO: 27) and A-E2s R (SEQ ID NO: 28), respectively. The amplification was performed to obtain the N-terminal fragments of the fusion proteins. For the second PCR reaction, the full-length gene of CRM197 was used as template. The forward primer were 389-E2s F (SEQ ID NO: 29) and A-E2s F (SEQ ID NO:30), respectively. The reverse primer was DrP59 R, at the 5' terminal of which the restriction endonuclease EcoRI site GAA TTC was introduced. The amplification was performed to obtain the C-terminal fragments of the fusion proteins. The first and second PCR reactions were performed in a PCR thermocycler (Biometra T3) under the following conditions.

| 94° C. denaturation 10 min | 1 cycle |
|---|---|
| 94° C. denaturation 50 sec | 20 cycle |
| 58° C. annealing 50 sec | |
| 72° C. elongation 50 sec | |
| 72° C. elongation 10 min | 1 cycle |

For the third PCR reaction, the amplification products of the first and second PCR reactions were used as templates (for example, the two fragments obtained by using 389-E2sF and 389-E2sR as primers were used as template for amplification of 389-E2s), and CRM197F and DrP59R were used as primers. The amplification was performed in a PCR thermocycler (Biometra T3) under the following conditions.

| 94° C. denaturation 10 min | 1 cycle |
|---|---|
| 94° C. denaturation 50 sec | 20 cycle |
| 58° C. annealing 50 sec | |
| 72° C. elongation 50 sec | |
| 72° C. elongation 10 min | 1 cycle |

The amplification products were DNA fragments of about 1600 bp and 1000 bp in length, respectively. The amplification products obtained above were linked into commercially available pMD 18-T vector (produced by TAKARA Co.), respectively. As identified by NdeI/EcoRI enzyme cleavage, the positive clones pMD 18-T-389-E2s and pMD 18-T-A-E2s were obtained.

As confirmed by M13(+) primer, correct nucleotide sequences of SEQ ID NO:15 and SEQ ID NO:17 (which encoded the amino acid sequences of SEQ ID NO:16 and SEQ ID NO:18, respectively) were inserted into the obtained pMD 18-T-389-E2s and pMD 18-T-A-E2s, respectively.

The plasmids pMD 18-T-389-E2s and pMD 18-T-A-E2s were digested by NdeI/EcoRI enzyme. The fragments obtained by enzyme cleavage were then linked into the prokaryotic expression vector pTO-T7 digested by NdeI/EcoRI enzyme (Luo Wenxin et al., Chinese Journal of Biotechnology, 2000, 16:53-57). As identified by NdeI/EcoRI enzyme cleavage, the positive plasmids pTO-T7-389-E2s and pTO-T7-A-E2s, into which 389-E2s and A-E2s were inserted, respectively, were obtained.

The sequences of the primers used in the Example were shown in Table 1.

bator at 180 rpm for 10 h at 37° C., and then 1 ml bacterial solutions was taken and stored at −70° C.

Example 3. The Expression and Purification of the Fusion Proteins Constructed in Example 2

Expression of Fusion Proteins and Purification of Inclusion Bodies

5 µL bacterial solution, taken from an ultra low temperature freezer at −70° C., was seeded to 5 mL liquid LB medium containing kanamycin, and then was cultured at 37° C., 180 rpm under shaking until OD600 reached about 0.5. The resultant solution was transferred to 500 ml LB medium containing kanamycin, and then was cultured at 37° C., 180 rpm under shaking for 4-5 h. When OD600 reached about 1.5, IPTG was added to a final concentration of 0.4 mM, and the bacteria were induced under shaking at 37° C. for 4 h.

After induction, centrifugation was performed at 8000 g for 5 min to collect the bacteria, and then the bacteria were re-suspended in a lysis solution at a ratio of 1 g bacteria to

TABLE 1

Primer sequences

| SEQ ID NO: | Primer Name | Primer sequence (5'-3') |
|---|---|---|
| 19 | CRM197F | CATATGGGCGCTGATGATGTTGTTGATTCTTCT |
| 20 | CRM197R | GAATTCCCCACTACCTTTCAGCTTTTG |
| 21 | CRM197-linker R | GGATCCACCGCCACCGCTGCCACCGCCACCGCTGCCACCGCCACCGCTTTTGAT |
| 22 | 389-linker R | GGATCCACCGCCACCGCTGCCACCGCCACCGCTGCCACCGCCACCAAATGGTTGC |
| 23 | A-linker R | GGATCCACCGCCACCGCTGCCACCGCCACCGCTGCCACCGCCACCACGATTTCCTGCAC |
| 24 | E2F | GGATCCCAGCTGTTCTACTCTCGTC |
| 25 | E2sF | GGATCCTCCCCAGCCCCATCGCGC |
| 26 | Drp59R | GAATTCCTAGCGCGGAGGGGGGCT |
| 27 | 389-E2s R | GATGGGGCTGGGGAAAATGGTTG |
| 28 | A-E2s R | GATGGGGCTGGGGAACGATTTCCTGCAC |
| 29 | 389-E2s F | CGCAACCATTTTCCCCAGCCC |
| 30 | A-E2s F | GAAATCGTTCCCCAGCCCCAT |

1 µL of plasmids pTO-T7-CRM197-L-E2, pTO-T7-CRM197-L-E2s, pTO-T7-389-L-E2, pTO-T7-389-L-E2s, pTO-T7-389-E2s, pTO-T7-A-L-E2, pTO-T7-A-L-E2s and pTO-T7-A-E2s (0.15 mg/ml) were separately used to transform 40 µL competent E. coli ER2566 (purchased from Invitrogen) prepared by the Calcium chloride method, and then the bacteria were plated on solid LB medium (the components of the LB medium: 10 g/L peptone, 5 g/L yeast powder, and 10 g/L NaCl, the same below) containing kanamycin (at a final concentration of 100 mg/ml, the same below). The plates were statically incubated at 37° C. for about 10-12 h until individual colonies could be observed clearly. Individual colonies from the plates were transferred to a tube containing 4 ml liquid LB medium containing kanamycin. The cultures were incubated in a shaking incu- 10 mL lysis solution (20 mM Tris buffer pH7.2, 300 mM NaCl), in ice-bath. The bacteria were treated with a sonicator (Sonics VCX750 Type Sonicator) (conditions: operating time 15 min, pulse 2s, intermission 4s, output power 55%). The bacterial lysate was centrifuged at 12000 rpm, 4° C. for 5 min (the same below), the supernatant was discarded and the precipitate (i.e. inclusion body) was kept; 2% Triton-100 of the same volume was used for washing, the result mixture was under vibration for 30 min, centrifuged, and the supernatant was discarded. The precipitate was re-suspended in Buffer 1 (20 mM Tris-HCl pH8.0, 100 mM NaCl, 5 mM EDTA), under vibration for 30 min, centrifuged, and the supernatant was discarded. The precipitate was then re-suspended in 2M urea, under vibration at 37° C. for 30 min, centrifuged, the supernatant and the precipitate were obtained. The supernatant was kept; and the precipitate was re-suspended in 4M urea in the same volume, under vibration at 37° C. for 30 min, and centrifuged at 12000 rpm, 4° C. for 15 min to obtain the supernatant and precipitate. The supernatant (i.e. the 4M urea-dissolved supernatant) was kept; and the precipitate was further in re-suspended in 8M urea in the same volume, under vibration at 37° C. for 30 min, and centrifuged, and the supernatant (i.e. the 8M urea-dissolved supernatant) was kept.

The SDS-PAGE analytic results of the obtained fractions (Coomassie brilliant blue staining was used for visualization, the same below, see the methods in The Molecular Cloning Experiment Guide, $2^{nd}$ edition) was showed in FIG. 2. The results showed that the fusion proteins were expressed in inclusion bodies (see FIG. 2A), and CRM197-L-E2, 389-L-E2, A-L-E2, and A-E2s were mainly dissolved in 4M urea (see FIG. 2B), CRM197-L-E2s, 389-L-E2s, A-L-E2s, and 389-E2s were mainly dissolved in 8M urea (see FIG. 2C). The 4M urea-dissolved supernatants or the 8M urea-dissolved supernatants containing the fusion protein, were dialyzed to PBS, respectively, to get the fusion proteins with a purity of about 80% (see FIG. 2D).

Purification of the Fusion Protein A-L-E2 by Anion Exchange Chromatography

Sample: a solution of A-L-E2 protein with a purity of about 80% as obtained above.

Equipment: AKTA Explorer 100 preparative liquid chromatography system produced by GE Healthcare (i.e. the original Amersham Pharmacia Co.)

Chromatographic media: Q SEPHAROSE® Fast Flow (GE Healthcare Co.)

Column Volume: 15 mm×20 cm
Buffer: 20 mM phosphate buffer pH 7.7+4M urea
20 mM phosphate buffer pH 7.7+4M urea+1M NaCl
Flow Rate: 6 mL/min
Detector Wavelength: 280 nm Elution protocol: eluting the protein of interest with 150 mM NaCl, eluting the undesired protein with 300 mM NaCl, and collecting the fraction eluted with 150 mM NaCl.

Purification of the Fusion Protein A-L-E2 by Hydrophobic Interaction Chromatography Equipment: AKTA Explorer 100 preparative liquid chromatography system produced by GE Healthcare (i.e. the original Amersham Pharmacia Co.)

Chromatographic media: Phenyl SEPHAROSE® Fast Flow (GE Healthcare Co.) Column Volume: 15 mm×20 cm Buffer: 20 mM phosphate buffer pH 7.7+4M urea+0.5 M $(NH_4)_2SO_4$
20 mM phosphate buffer pH 7.7+4M
Flow Rate: 5 mL/min
Detector Wavelength: 280 nm Sample: the fraction eluted with 150 mM NaCl as obtained in the previous step was dialyzed to a buffer (20 mM phosphate buffer pH 7.7+4M urea+0.5 M $(NH_4)_2SO_4$), and then was used as sample.

Elution protocol: eluting the undesired protein with 0.3M $(NH_4)_2SO_4$, eluting the protein of interest with 0.1M and 0M $(NH_4)_2SO_4$, and collecting the fraction eluted with 0.1M and 0M $(NH_4)_2SO_4$.

Figure 3:
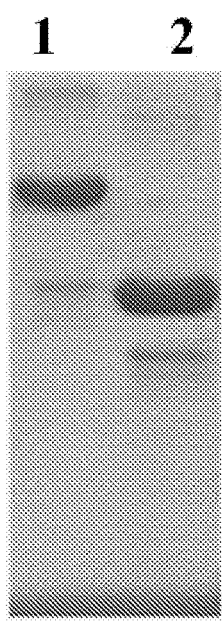
FIG. 3 shows the SDS-PAGE result of the fusion protein A-L-E2 purified by chromatography, wherein Lane 1 refers to A-L-E2 which is renatured to PBS after purification by chromatography, Lane 2 refers to a A-L-E2 sample of Lane 1 boiled in boiling water for 10 mins. The results showed that after two-step chromatography, A-L-E2 could reach a purity of above 90%.

The fraction eluted with 0.1M and 0M $(NH_4)_2SO_4$ was dialyzed and renatured into PBS, and then 10 μl was taken for SDS-PAGE analysis, and electrophoresis bands were visualized by Coomassie brilliant blue staining. The results showed that after the above purification steps, the fusion protein A-L-E2 had a purity of above 90% (See FIG. 3).

Figure 4:
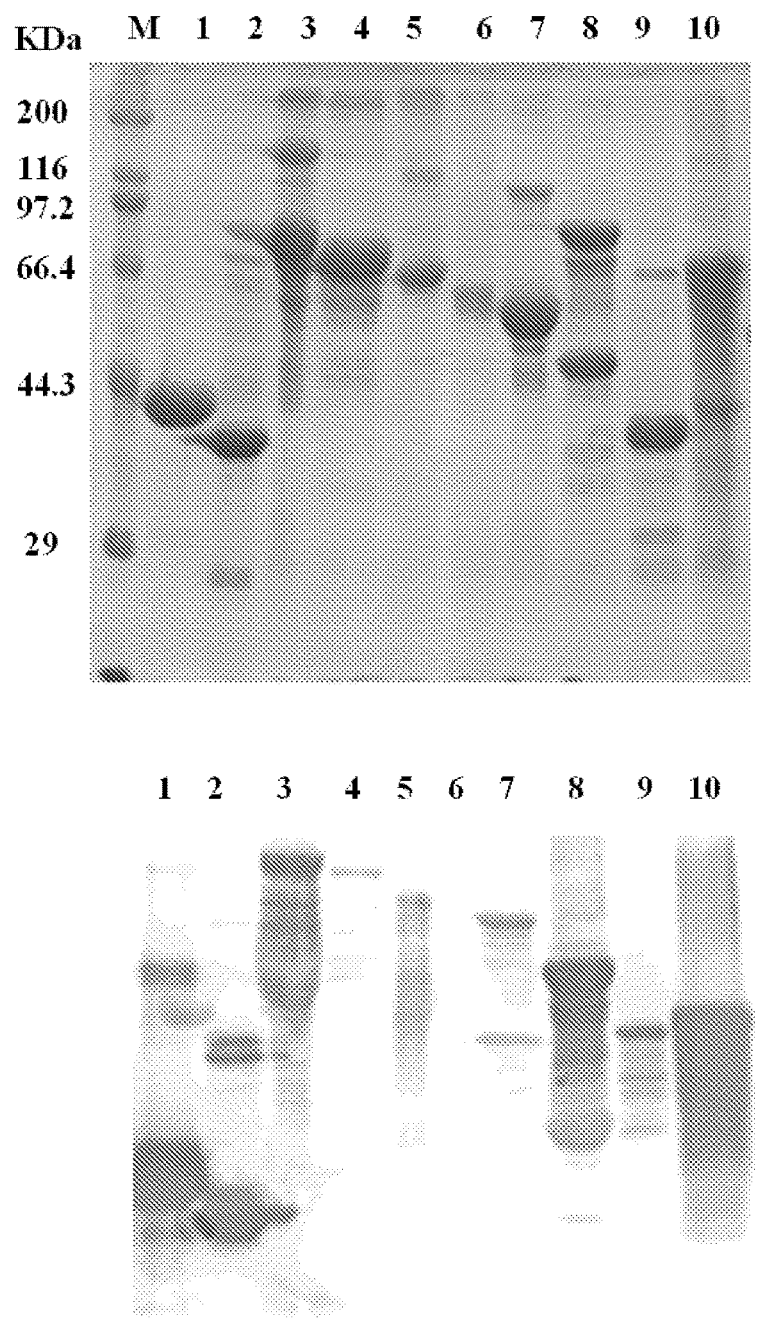
FIG. 4 shows the results of Western blotting using the fusion proteins constructed in Example 2 and HEV neutralizing monoclonal antibody 8C11. Lane M: protein molecular weight marker; Lane 1: Control protein HEV-239; Lane 2: Control protein E2, Lane 3: CRM197-L-E2; Lane 4: CRM197-L-E2s; Lane 5: 389-L-E2; Lane 6: 389-L-E2s; Lane 7: 389-E2s; Lane 8: A-L-E2; Lane 9: A-L-E2s; Lane 10: A-E2s. The results showed that all the fusion proteins tested had significant reactivity with the HEV-specific neutralizing monoclonal antibody 8C11.

Example 4. Analysis of Properties of the Fusion Proteins Constructed in Example 2 Determination of the Reactivity of the Fusion Proteins with Antibodies by Western Blotting The reactivity of the fusion proteins with HEV neutralizing monoclonal antibody 8C11 (see, Zhang et al., Vaccine. 23(22): 2881-2892 (2005)) and anti-CRM197 polyclonal antiserum (which was prepared by immunizing mice with CRM197 through methods well known in the art, and the reactivity of the serum was confirmed by commercially available CRM197) were determined by Western blotting. The dialyzed and renatured samples were transferred to nitrocellulose membrane for blotting after SDS-PAGE separation; 5% skimmed milk was used to block the membrane for 2 h, monoclonal antibody 8C11 diluted at a certain ratio was then added (monoclonal antibody was diluted at 1:500, and polyclonal antiserum was diluted at 1:1000), and the reaction was carried out for 1 h. The membrane was washed with TNT (50 mmol/L Tris.Cl (pH 7.5), 150 mmol/L NaCl, 0.05% Tween 20) for three times, 10 min for each time. Goat Anti-mouse alkaline phosphatase (KPL product) was then added, the reaction was carried out for 1 h, and the membrane was then washed with TNT for three times, 10 min for each time. NBT and BCIP (PROTOS product) were used for visualization. The results, as determined by Western blotting using the fusion proteins and HEV neutralizing monoclonal antibody 8C11, were shown in FIG. 4. The results showed that all the tested fusion proteins had significant reactivity with HEV neutralizing monoclonal antibody 8C11.

Figure 5A:
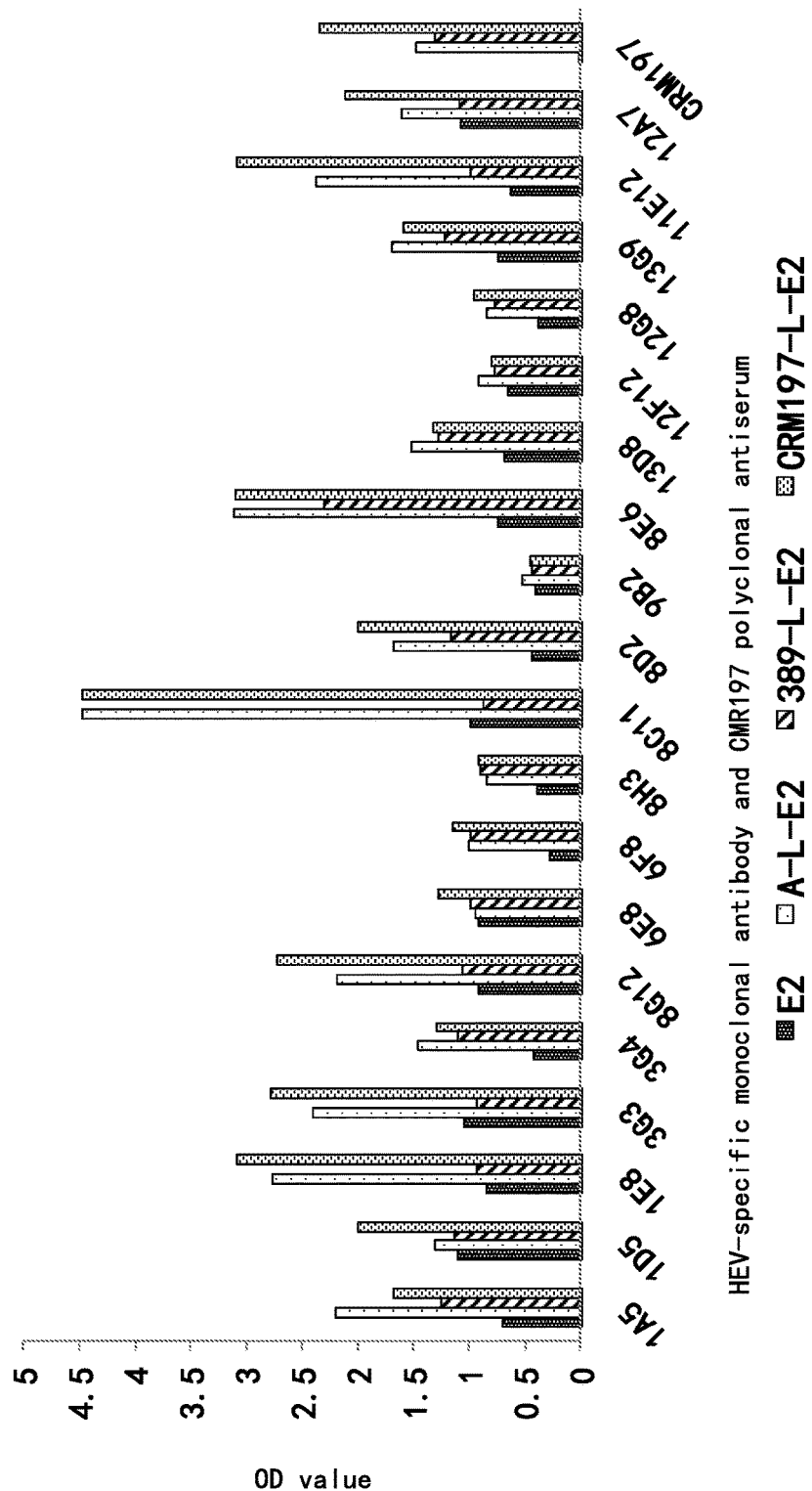
FIGS. 5A-5B show the results of indirect ELISA using the fusion proteins constructed in Example 2 and HEV-specific monoclonal antibody. The abscissa refers to HEV-specific monoclonal antibody or CRM197 polyclonal antiserum for ELISA, and the ordinate refers to OD value determined by ELISA at the same antibody dilution.
Figure 5B:
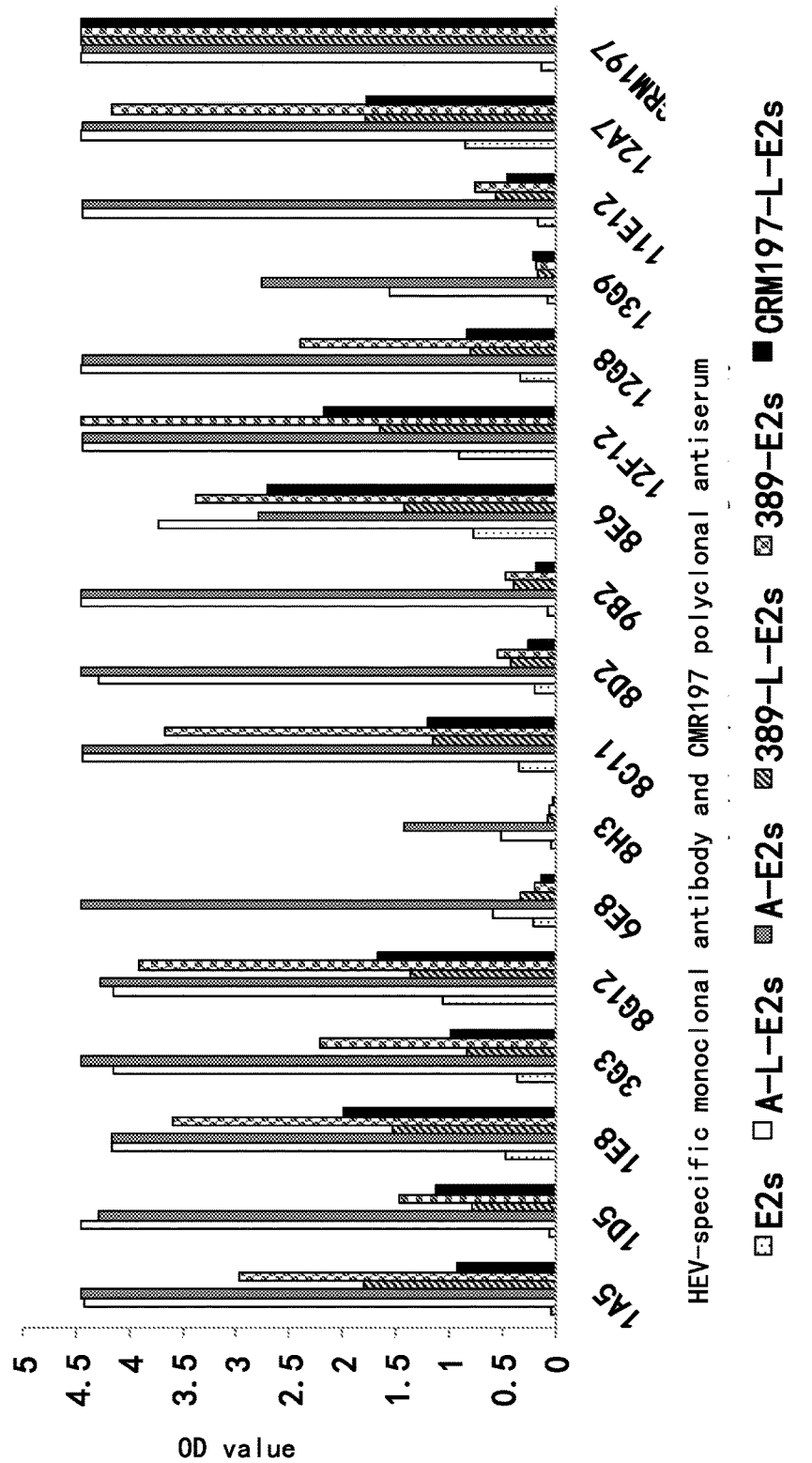

Determination of the Reactivity of the Fusion Proteins with Various HEV Specific Antibodies by ELISA The reactivity of the fusion proteins and the control proteins E2 and HEV-239 with various HEV specific antibodies (Gu Ying et al., Chinese Journal of Virology, 19(3): 217-223(2003)) was determined by indirect ELISA. The dialyzed and renatured samples were diluted in 1×PBS (1 μg/ml), and then were added to 96-well microplate (Beijing Wantai Co.) at 100 μl/well and incubated at 37° C. for 2 h. The coating solution was discarded, the plate was washed with PBST (PBS+0.05% Tween-20) once, and then the blocking solution (2% gelatin, 5% Casein, 1% PROCLIN® 300, in PBS) was added at 200 μl/well and incubated at 37° C. for 2 h. The blocking solution was discarded when the detection was performed, and the HEV monoclonal antibodies diluted at a certain ratio (when E2s and its fusion protein were detected, they were diluted at 1:10000; when E2 and its fusion protein were detected, they were diluted at 1:100000; when the reactivity of A-L-E2, 239 and E2 proteins was compared, the monoclonal antibodies were subjected to 10-fold serial dilution wherein 1 mg/ml was used as the initial concentration, and the polyclonal antibody at its initial concentration was subjected to dilution in the same manner) was added at 100 μl/well. The mixture was incubated at 37° C. for 1-2 h. The plate was then washed with PBST for five times, and HRP-labeled Goat anti Mouse (KPL product) (1:5000) was then added at 100 μl/well and was incubated at 37° C. for 30 min; the plate was then washed with PBST for five times, HRP substrate (Beijing Wantai Co.) was then added at 100 μl/well and was incubated at 37° C. for 15 min. 2M sulphuric acid was added at 50 μl/well to stop the reaction, and Microplate reader (Sunrise Type, product from Tecan Co.) was then used to read OD450/620 value. The results of the ELISA using the fusion proteins with the monoclonal antibodies were shown in FIG. 5. The results showed that the reactivity of E2s protein with the monoclonal antibody was significantly enhanced, after its fusion with CRM197 or a fragment thereof, wherein the reactivity of A-L-E2s and A-E2s was enhanced most significantly; the reactivity of E2 protein with HEV-specific monoclonal antibody was retained or enhanced, after its fusion with CRM197 or a fragment thereof.

Figure 6:
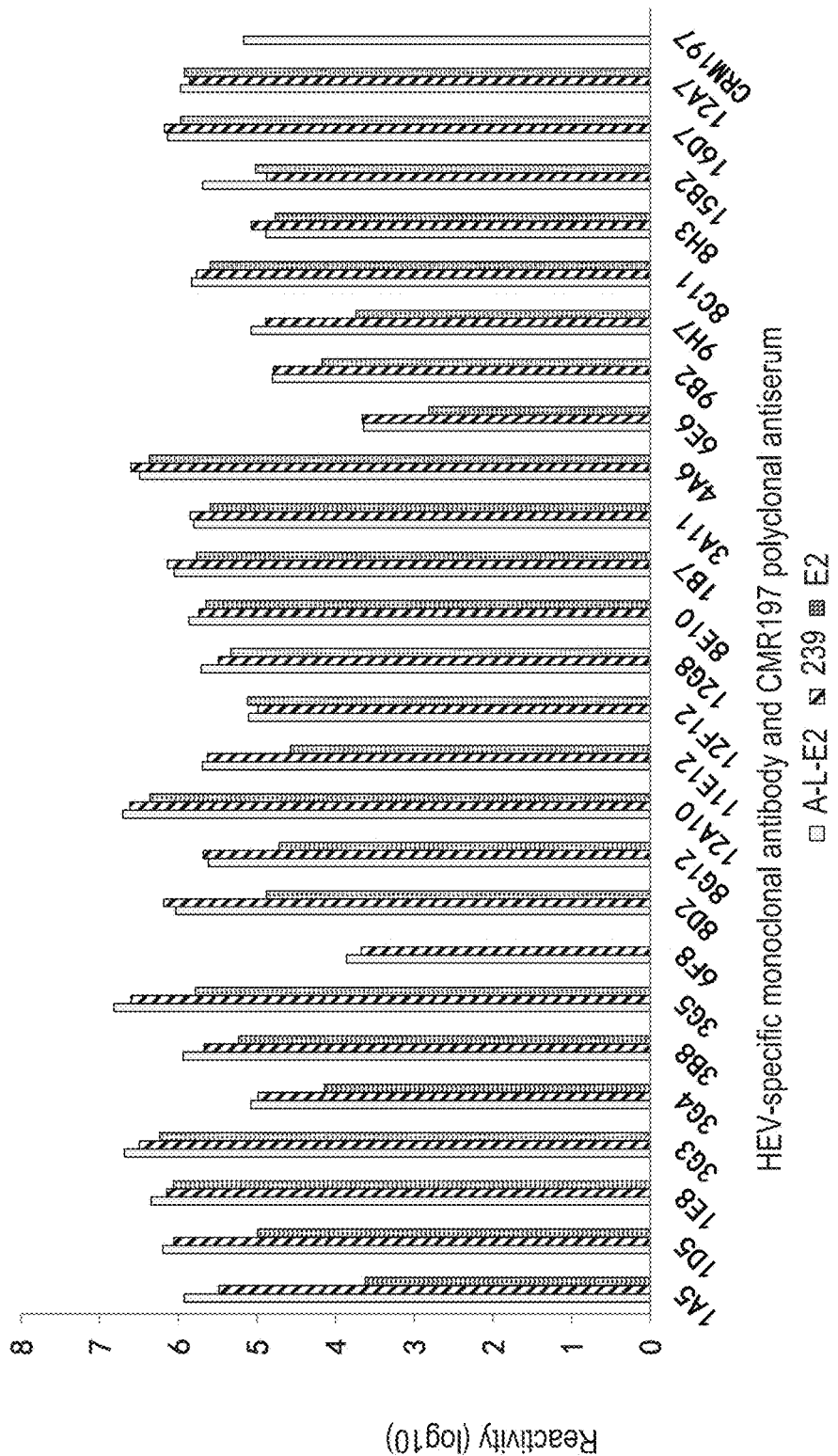
FIG. 6 shows the results of indirect ELISA using the proteins A-L-E2, HEV-239 or E2 and HEV-specific monoclonal antibody, wherein the cutoff value is defined as three times of the average negative value. The results showed that the reactivity of A-L-E2 with HEV-specific monoclonal antibody is comparable to that of HEV-239 and E2.

Analysis of the Reactivity of the Fusion Protein A-L-E2 Purified by Chromatography The reactivity of the fusion protein A-L-E2, purified by two-step chromatography, was analyzed by indirect ELISA (see the concrete process in the previous step). The ELISA result was shown in FIG. 6. The result showed that the reactivity of A-L-E2 with HEV specific monoclonal antibody was comparable to that of the control proteins HEV-239 and E2.

Analysis of Sedimentation Velocity (SV) of the Fusion Protein A-L-E2

Figure 7:
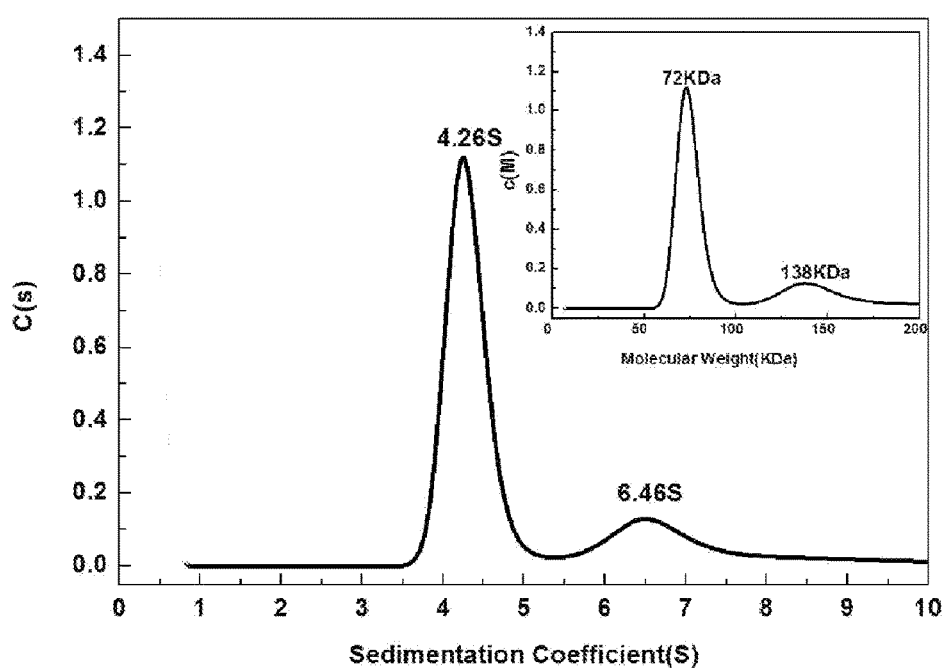
FIG. 7 shows the analytic result of Sedimentation Velocity (SV) of the fusion protein A-L-E2. The result showed that the fusion protein A-L-E2 was mainly present in a form of dimer, and tetramer is present in a small amount.

The apparatus used in the experiment was US Beckman XL-A analytic supercentrifuge, which was equipped with an optical detection system and An-50Ti and An-60Ti rotators. The Sedimentation Velocity (SV) method (c(s) algorithm, see P. Schuck et al., Biophys J 78: 1606-1619(2000)) was used to analyze the sedimentation coefficient of the fusion protein A-L-E2. The analytic result was shown in FIG. 7. The result showed that the fusion protein A-L-E2 was mainly present in a form of dimer, and some dimers might be further polymerized to form a tetramer.

Example 5. Analysis of Immunogenicity of the Fusion Proteins Constructed in Example 2

Antibody Titers Induced by the Fusion Proteins

The mice used in the experiment were female, 6-week old BALB/C mice. By using aluminum adjuvant, mice were immunized by intraperitoneal injection of the fusions proteins which were prepared by the methods in the Example 3 and renatured to PBS and the control proteins HEV-239, E2 and E2s, respectively. The injection volume was 1 ml, and two dose groups (a 5 µg-dose group or a 0.5m-dose group) were used. The primary immunization was performed at week 0, and booster immunization was performed at week 2 and 4.

Figure 8A:
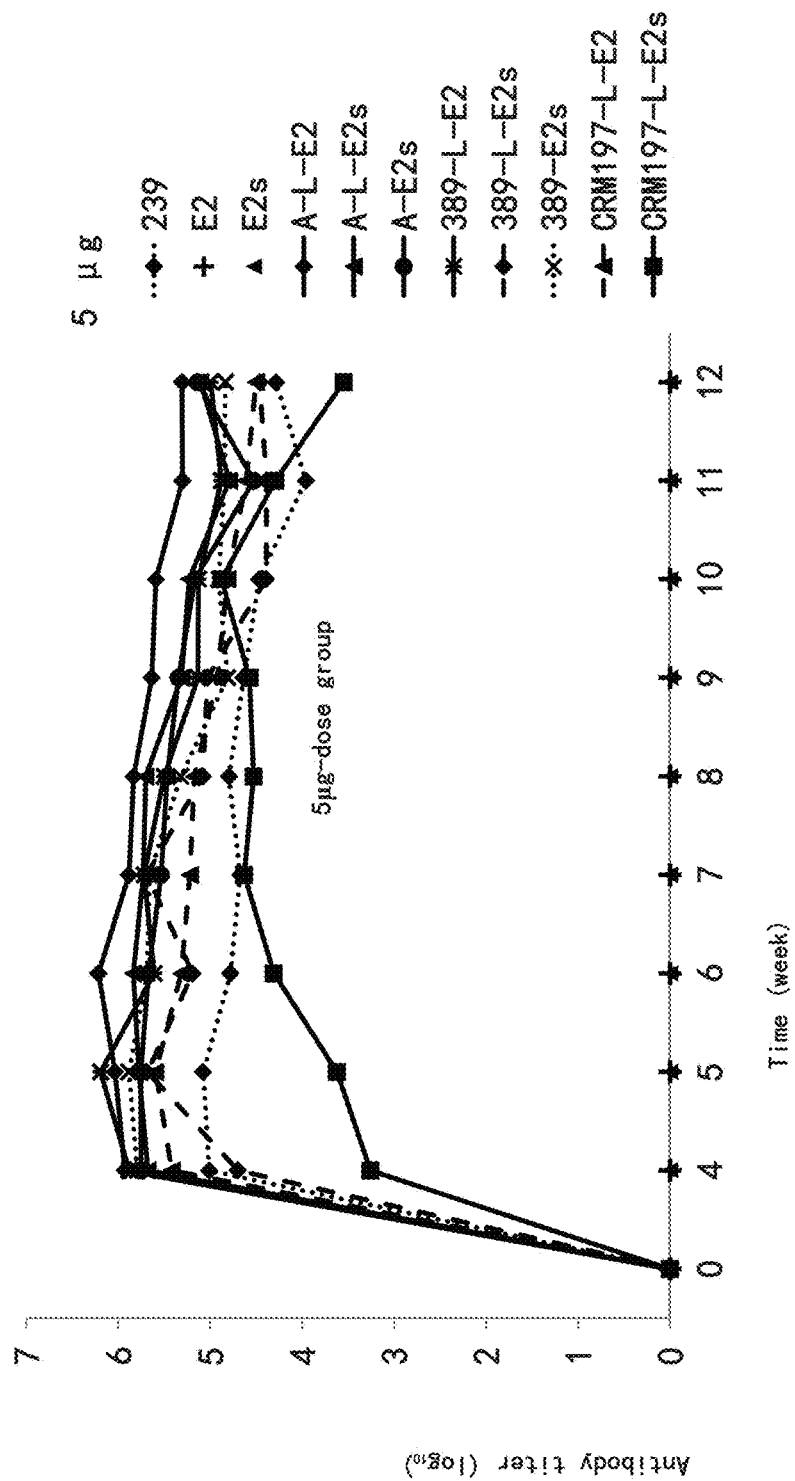
FIGS. 8A-8B show the comparison of immunogenicity between the fusion proteins constructed in Example 2 and HEV-239. The primary immunization was performed at week 0, and booster immunization was performed at week 2 and 4, wherein the dose for both the primary immunization and the booster immunization was 5 µg or 0.5 µg. FI Lane 1: M2e-L-A protein, not treated by boiling;
Lane 2: M2e-L-A protein, treated by boiling;
Lane 3: M2e-L-389 protein, not treated by boiling;
Lane 4: M2e-L-389 protein, treated by boiling;
Lane 5: M2e-L-CRM197 protein, not treated by boiling;
Lane 6: M2e-L-CRM197 protein, treated by boiling.
Figure 8B:
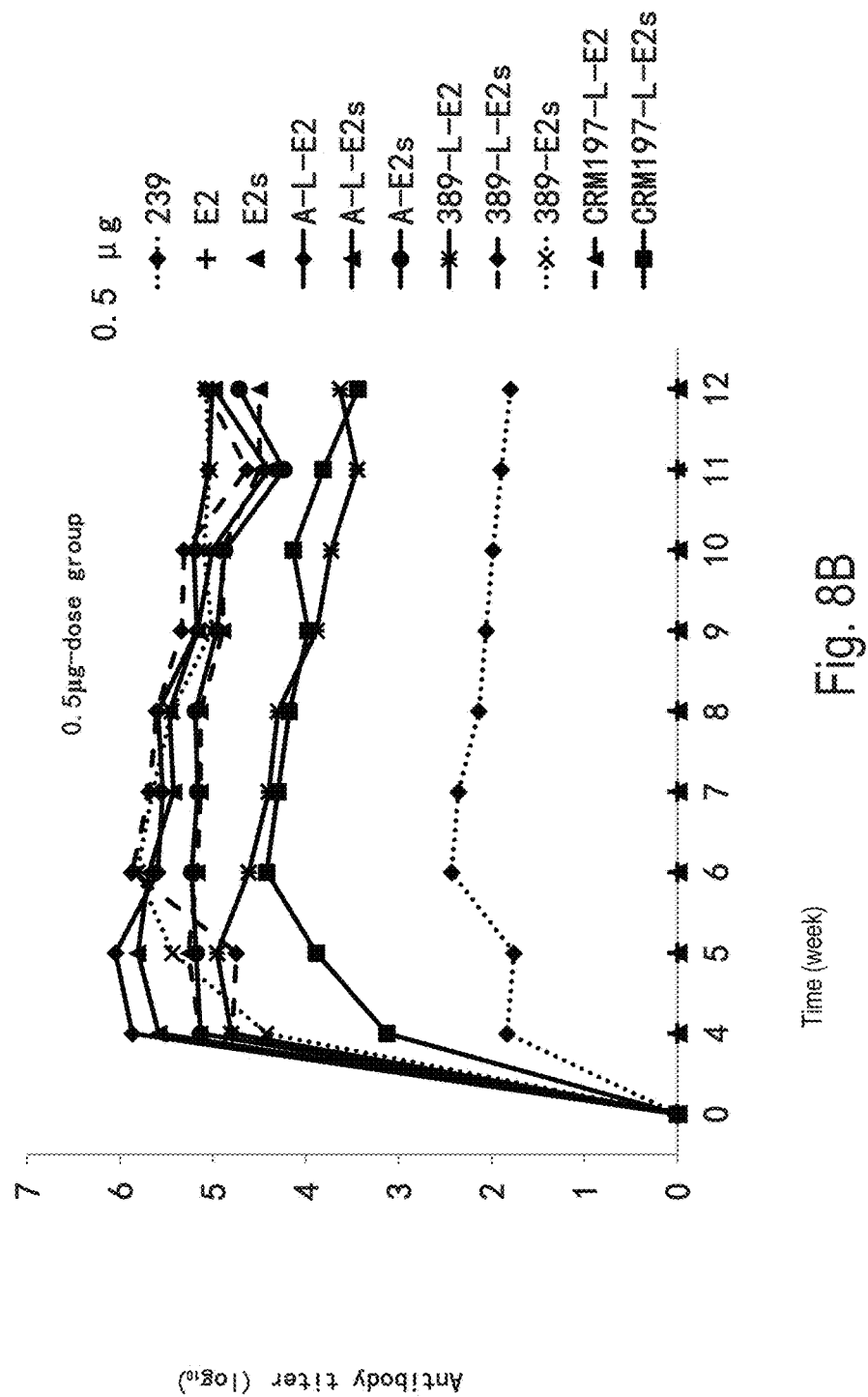

HEV-239 was used to coat a plate, and the antibody titers in serum as induced by the fusion proteins and the control proteins, were measured by similar indirect ELISA assay as described above. The detection results of the serum antibody titers within 3 months after immunization were shown in FIG. 8. The results showed that seroconversion occurred in mice serum at week 4 in both 5 µg- and 0.5 µg-dose groups, and the antibody titers reached the highest value at week 5 or 6. In particular, in 5 µg-dose group, the highest antibody titer was obtained when A-L-E2 was used, which reached $10^6$ at week 6; and the antibody titers induced by the fusion proteins were higher or comparable to that of HEV-239 protein. In 0.5 µg-dose groups, the antibody titers of the fusion proteins were significantly higher than that of HEV-239, and the antibody titer induced by A-L-E2 protein reached $10^6$ at week 5. In addition, seroconversion did not occur in immune serum when using E2 and E2s, in 5 µg- and 0.5 µg-dose groups. As seen from the above results, the immunogenicity of the constructed fusion proteins were significantly higher than the antigen protein (E2 and E2s) alone, indicating that the CRM197 of the invention or a fragment thereof significantly enhanced immunogenicity of the antigen protein fused therewith, and could be used as intramolecular adjuvant.

Investigation on Median Effective Dose (ED50) of the Fusion Protein A-L-E2

In the experiment, immunogenicity of fusion proteins was investigated by determining median effective dose (ED50). The experimental animals used were 3-4 week old female BALB/c mice. A-L-E2 was mixed with aluminum adjuvant, and the initial dose was 1 µg/mouse, and was subjected to serial dilution at 1:3, resulting in 8 dose groups in total. In addition, HEV-239 (HEV recombinant vaccine) was used as control, and the initial dose was 1.6 µg/mouse, and was subjected to serial dilution at 1:4, resulting in 4 dose groups in total. 6 mice were used in each group. The immunization was carried out by single intraperitoneal injection.

Peripheral venous blood was taken after 4 weeks following immunization, serum was separated, and serological conversion rate was determined by ELISA assay as described above. When the ELISA value of 100-fold diluted serum was higher than the cutoff value (i.e. three times of the average negative value), the serum was regarded as positive. The median effective dose (ED50) was calculated by Reed-Muench method. The serological conversion rate of the fusion protein A-L-E2 was shown in Table 2, and the serological conversion rate of HEV-239 vaccine was shown in Table 3.

TABLE 2

ED50 of A-L-E2 for inducing seroconversion of HEV antibody in mice

| Dose (µg) | Number of mice | Number of mice with seroconversion | Serological conversion rate | ED50 (µg) |
|---|---|---|---|---|
| 1.0000 | 6 | 6 | 100% | 0.0064 |
| 0.3333 | 6 | 6 | 100% | |
| 0.1111 | 6 | 6 | 100% | |
| 0.0370 | 6 | 6 | 100% | |
| 0.0123 | 6 | 6 | 100% | |
| 0.0041 | 6 | 1 | 16.7% | |
| 0.0013 | 6 | 0 | 0% | |
| 0.0005 | 6 | 0 | 0% | |

TABLE 3

ED50 of HEV-239 vaccine for inducing seroconversion of HEV antibody in mice

| Dose (µg) | Number of mice | Number of mice with seroconversion | Serological conversion rate | ED50(µg) |
|---|---|---|---|---|
| 1.6 | 6 | 6 | 100% | 0.071 |
| 0.4 | 6 | 5 | 83.3% | |
| 0.1 | 6 | 4 | 66.7% | |
| 0.025 | 6 | 0 | 0% | |

The results showed that ED50 of HEV-239 was 11 times of that of A-L-E2, indicating that CRM197 of the invention or a fragment thereof significantly enhanced immunogenicity of the antigen protein fused therewith, and could be used as intramolecular adjuvant. Meanwhile, since immunogenicity of the fusion protein A-L-E2 was significantly higher than that of HEV-239 vaccine in the form of virus like particle, the fusion protein might be used for the preparation of a new vaccine which is more effective for Hepatitis E.

Figure 9:
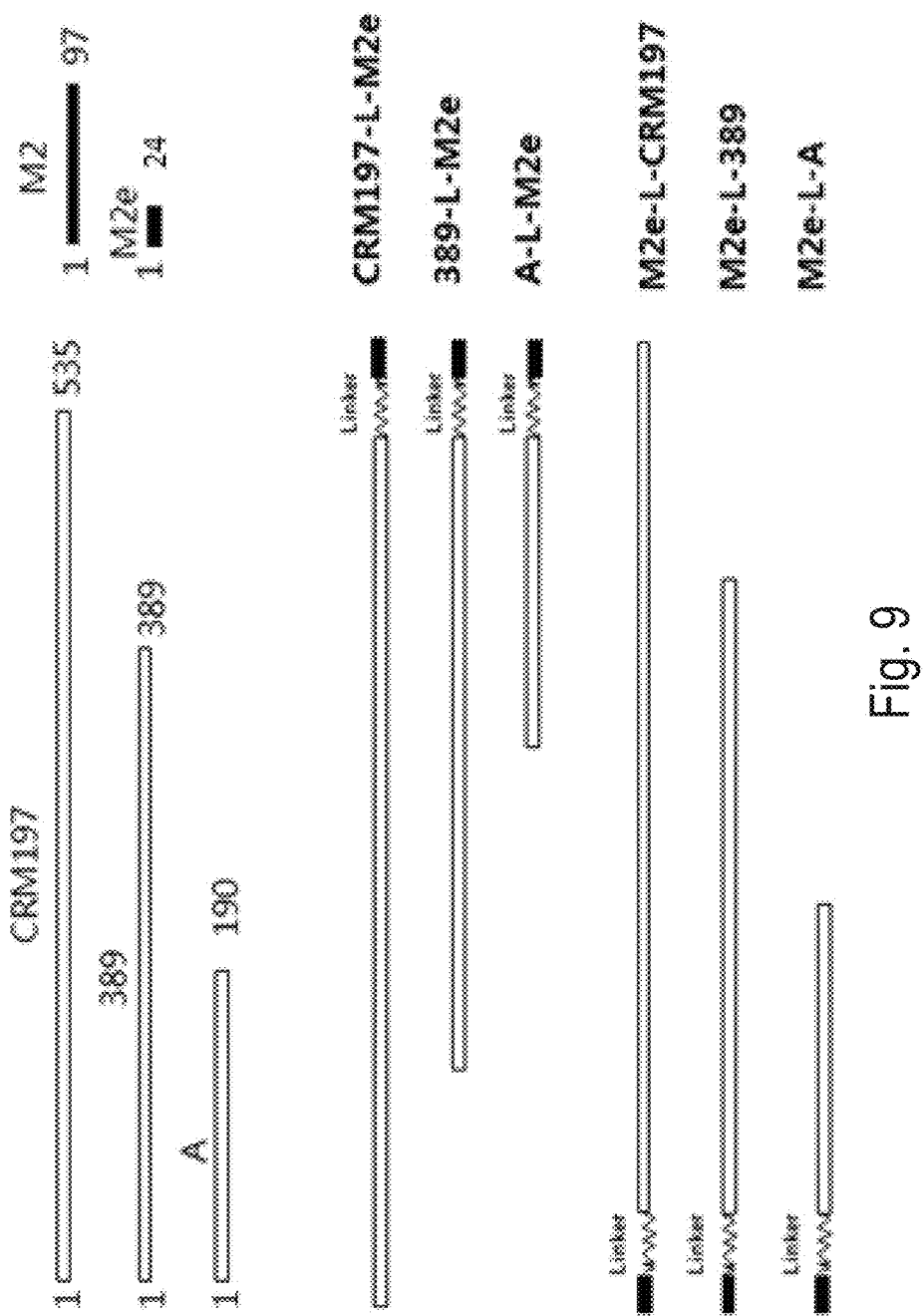
Figure 10A:
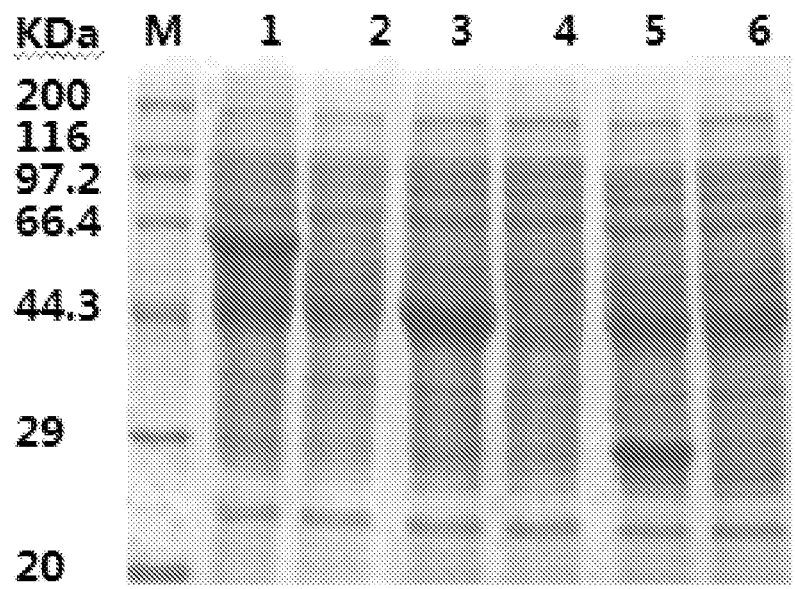
FIG. 10F used the samples that were the fusion proteins isolated and renatured into PBS, wherein β-mercaptoethanol was used during SDS-PAGE analysis, and the protein samples were treated by boiling (for 10 min) or not:
Lane 1: M2e-L-A protein, not treated by boiling;
Lane 2: M2e-L-A protein, treated by boiling;
Lane 3: M2e-L-389 protein, not treated by boiling;
Lane 4: M2e-L-389 protein, treated by boiling;
Lane 5: M2e-L-CRM197 protein, not treated by boiling;
Lane 6: M2e-L-CRM197 protein, treated by boiling.
Figure 10B:
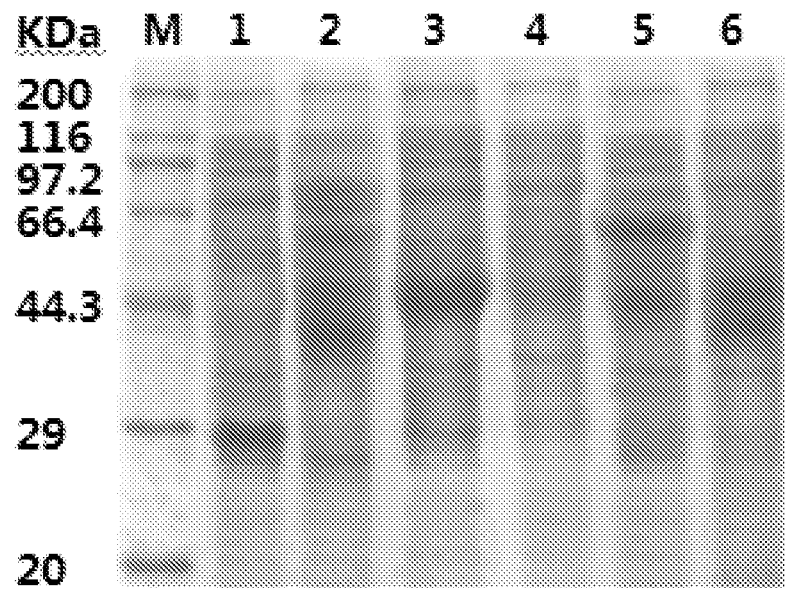
Figure 10C:
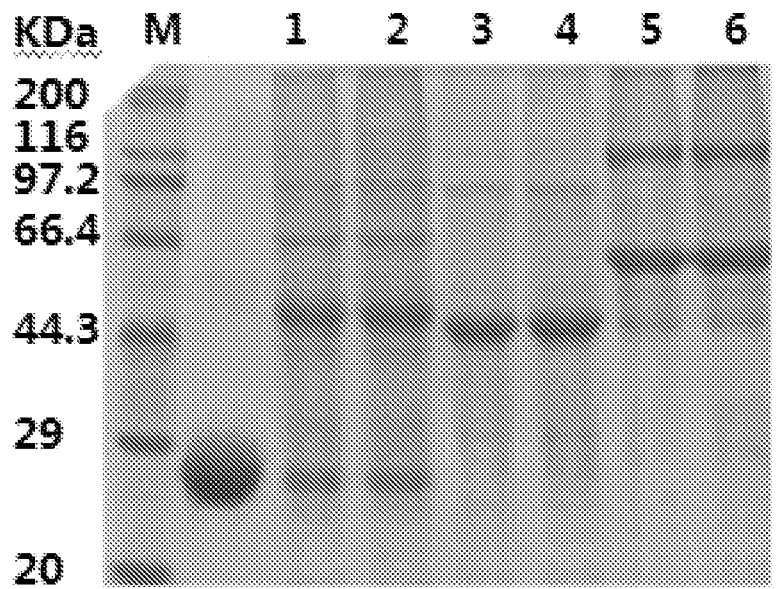
Figure 10D:
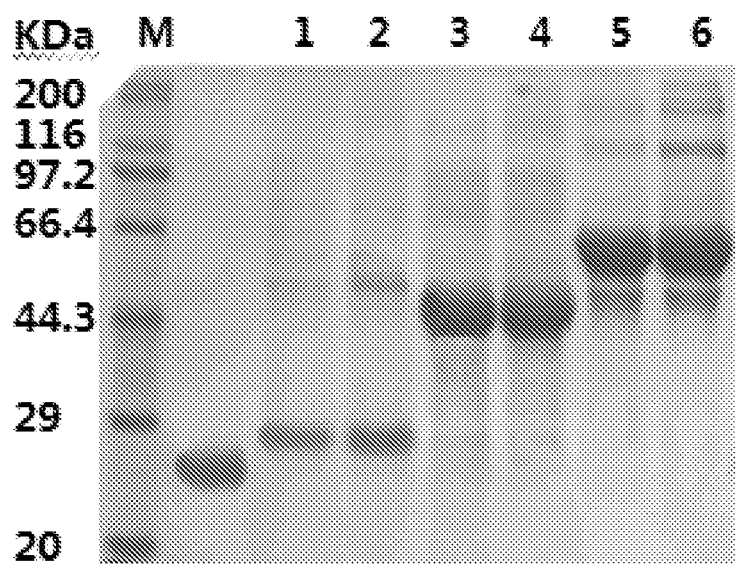
Figure 10E:
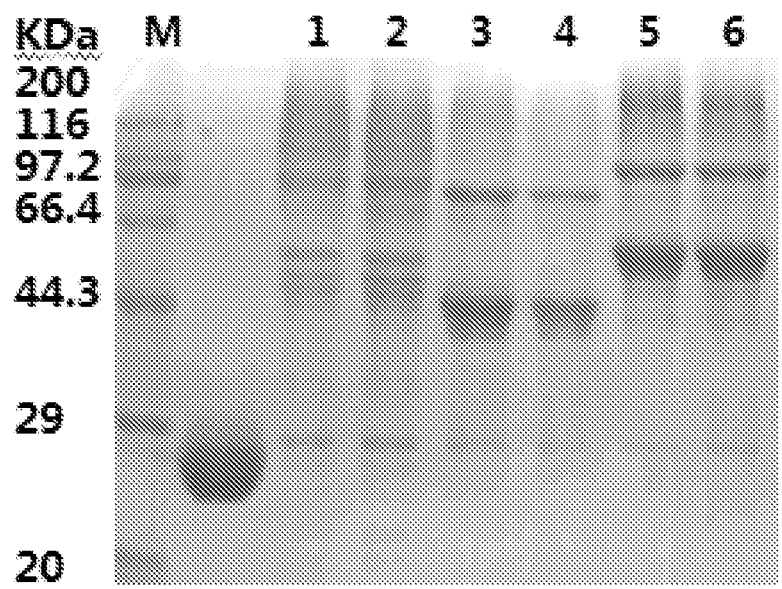
Figure 10F:
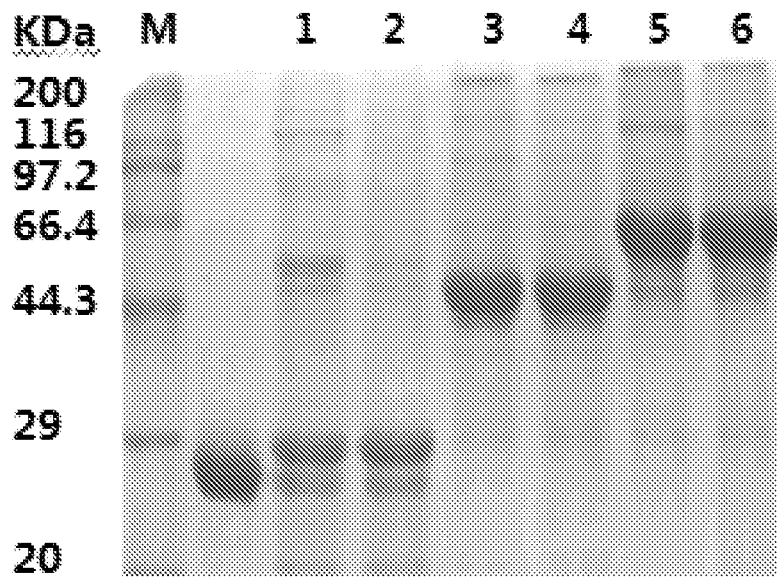
Figure 11A:
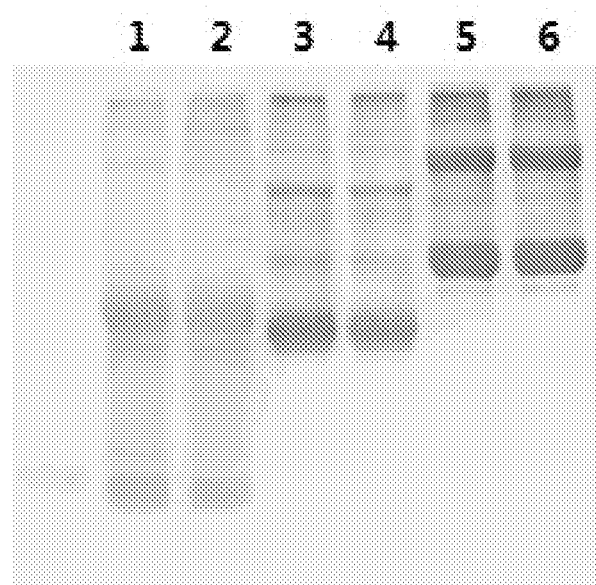
Figure 11B:
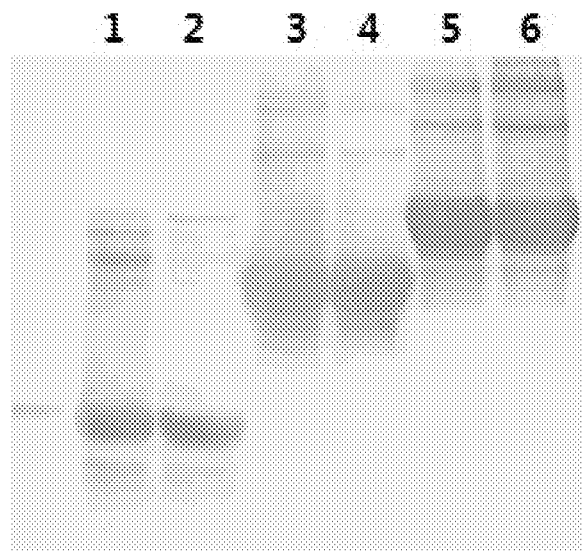
Figure 11C:
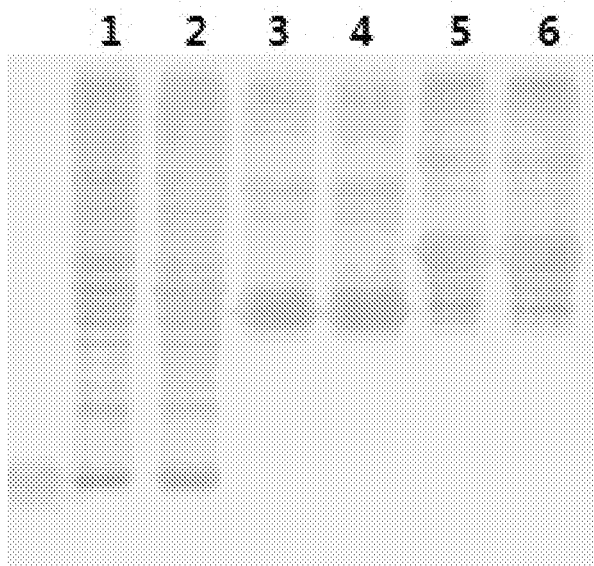
Figure 11D:
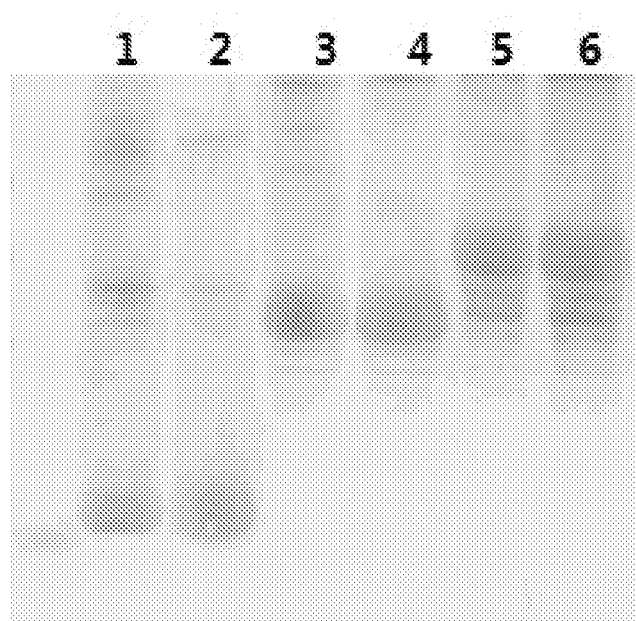
Figure 11E:
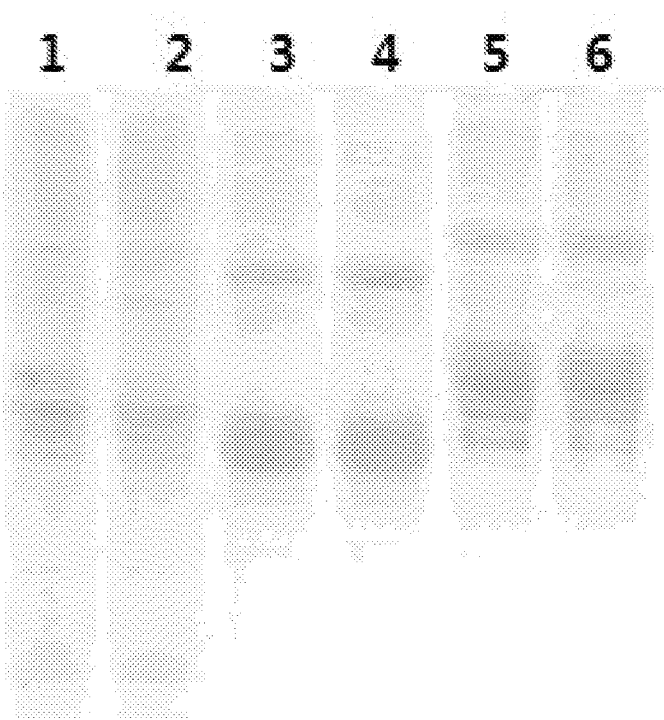
Figure 11F:
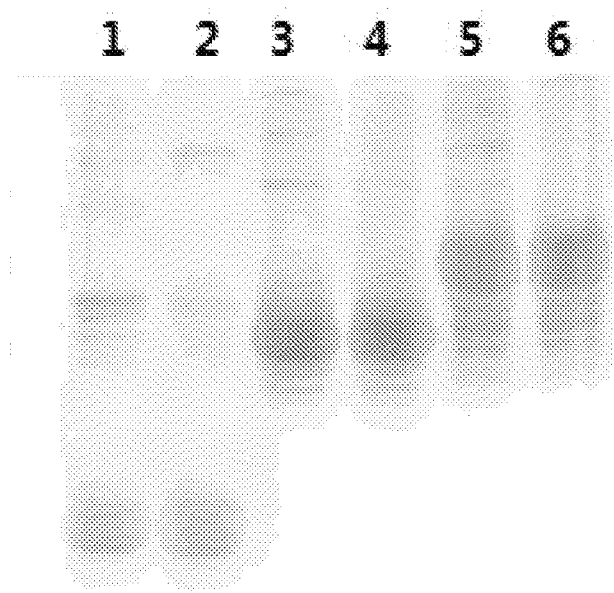
Figure 11G:
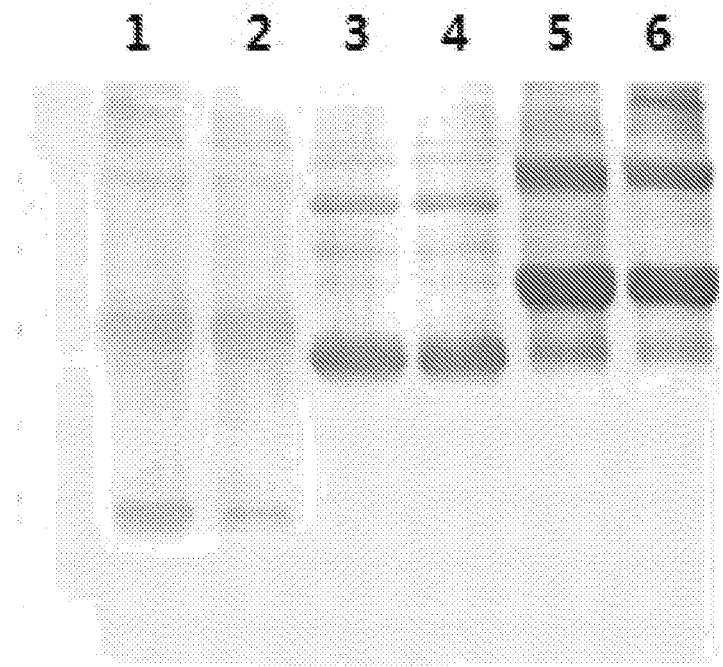
Figure 11H:
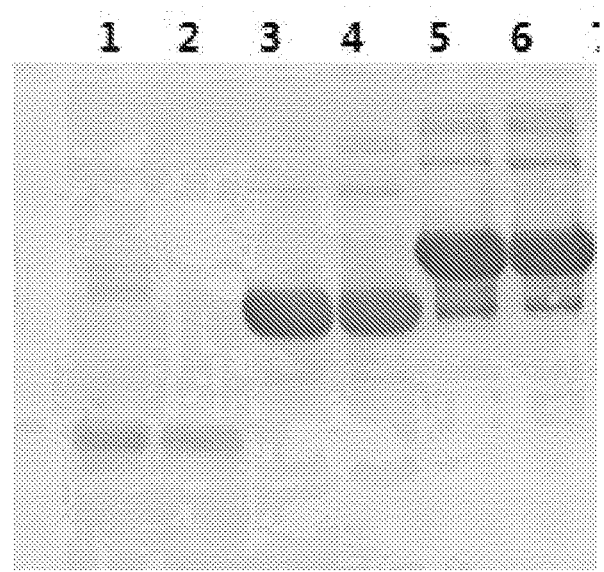

Example 6. Design and Clone of Fusion Proteins Comprising CRM197 or a Fragment Thereof and an Influenza Virus M2e Protein In the Example, vectors expressing the fusion proteins were constructed exemplarily. The clone design of the exemplary fusion proteins constructed is shown in FIG. 9, wherein the fusion proteins each comprise CRM197 or a fragment thereof and an influenza virus M2e protein, optionally using a linker.

Clone of Fusion Proteins

M2e Fused to the C-Terminus of CRM197 or a Fragment Thereof

The amplification product (i.e. the full-length gene of CRM197) obtained in the Example 1 was used as template. The forward primer was CRM197F1 (SEQ ID NO: 45), at the 5' terminal of which the restriction endonuclease NdeI site CAT ATG was introduced, wherein ATG was the initiation codon in E. coli system. The reverse primers were CRM197-linker R1 (SEQ ID NO: 46), 389-linker R1 (SEQ ID NO: 47) and A-linker R1 (SEQ ID NO: 48), respectively, at the 5' terminal of which the restriction endonuclease BamHI site GGA TCC was introduced. The PCR reaction was performed in a PCR thermocycler (Biometra T3) under the following conditions. The sequences of the primers used were shown in Table 4.

| 95° C. denaturation 10 min | 1 cycle |
|---|---|
| 95° C. denaturation 1.5 min | 20 cycle |
| 58° C. annealing 1.5 min | |
| 72° C. elongation 1.7 min | |
| 72° C. elongation 10 min | 1 cycle |

The amplification products were DNA fragments of about 1600 bp, 1200 bp and 600 bp in length, respectively.

In addition, the plasmid PHW2000 (stored in our lab, comprising the full-length gene of M2) was used as a template. The forward primer was M2eF1 (SEQ ID NO: 49), at the 5' terminal of which the restriction endonuclease BamHI GGA TCC was introduced. The reverse primer was M2eR (SEQ ID NO: 50), at the 5' terminal of which the restriction endonuclease EcoRI site GAA TTC was introduced. The PCR reaction was performed in a PCR thermocycler (Biometra T3) under the following conditions. The sequences of the primers used were shown in Table 4.

| 95° C. denaturation 10 min | 1 cycle |
|---|---|
| 95° C. denaturation 50 sec | 20 cycle |
| 58° C. annealing 50 sec | |
| 72° C. elongation 30 sec | |
| 72° C. elongation 10 min | 1 cycle |

The amplification products were DNA fragments of about 70 bp in length, respectively.

The amplification products as obtained above were linked into commercially available pMD 18-T vector (produced by TAKARA Co.), respectively, and designated as pMD 18-T-CRM197-L1, pMD 18-T-389-L1 and pMD 18-T-A-L1 as well as pMD 18-T-M2e. As identified by NdeI/BamHI and BamHI/EcoRI enzyme cleavage, respectively, the positive clones pMD 18-T-CRM197-L1, pMD 18-T-389-L1, pMD 18-T-A-L1 and pMD 18-T-M2e were obtained.

As confirmed by M13(+) primer, correct nucleotide sequences of interest were inserted into the obtained plasmids pMD 18-T-CRM197-L1, pMD 18-T-389-L1, pMD 18-T-A-L1 and pMD 18-T-M2e.

The plasmids pMD 18-T-CRM197-L1, pMD 18-T-389-L1 and pMD 18-T-A-L1 were digested by NdeI/BamHI enzyme. The fragments obtained by enzyme cleavage were linked into the prokaryotic expression vector pTO-T7 digested by NdeI/BamHI enzyme (Luo Wenxin et al., Chinese Journal of Biotechnology, 2000, 16:53-57), and were transformed into E. coli ER2566 (purchased from Invitrogen Co.); after extraction of plasmids, as identified by NdeI/BamHI enzyme cleavage, the positive plasmids pTO-T7-CRM197-L1, pTO-T7-389-L1 and pTO-T7-A-L1, into which the fragments CRM197-L1, 389-L1 and A-L1 were inserted, respectively, were obtained.

pTO-T7-CRM197-L1, pTO-T7-389-L1, pTO-T7-A-L1 and pMD 18-T-M2e were digested by BamHI/EcoRI enzyme. The obtained M2e fragment was linked into the vectors pTO-T7-CRM197-L1, pTO-T7-389-L1 and pTO-T7-A-L1 digested by BamHI/EcoRI enzyme, respectively. As identified by NdeI/EcoRI enzyme cleavage, the positive expression vectors pTO-T7-CRM197-L-M2e, pTO-T7-389-L-M2e, and pTO-T7-A-L-M2e, into which CRM197-L-M2e (SEQ ID NO:33, 34), 389-L-M2e (SEQ ID NO:35, 36), or A-L-M2e (SEQ ID NO:37, 38) was inserted respectively, were obtained.

M2e Fused to the N-Terminus of CRM197 or a Fragment Thereof.

The plasmid PHW2000 (stored in our lab, containing the full-length gene of M2) was used as template. The forward primer was M2eF2 (SEQ ID NO: 51), at the 5' terminal of which the restriction endonuclease NdeI CAT ATG was introduced, wherein ATG was the initiation codon in E. coli system. The reverse primer was M2e-Linker R (SEQ ID NO: 52), at the 5' terminal of which the restriction endonuclease BamHI GGA TCC was introduced. The PCR reaction was performed in a PCR thermocycler (Biometra T3) under the following conditions.

| 95° C. denaturation 10 min | 1 cycle |
|---|---|
| 95° C. denaturation 50 sec | 20 cycle |
| 58° C. annealing 50 sec | |
| 72° C. elongation 30 sec | |
| 72° C. elongation 10 min | 1 cycle |

The amplification products were DNA fragments of about 100 bp in length.

In addition, the amplification product (i.e. the full-length gene of CRM197) obtained in the Example 1 was used as template. The forward primer was CRM197F2 (SEQ ID NO: 53), at the 5' terminal of which the restriction endonuclease BamHI GGA TCC was introduced. The reverse primers were CRM197 R2 (SEQ ID NO: 54), 389 R (SEQ ID NO: 55), and A R (SEQ ID NO: 56), at the 5' terminal of which the restriction endonuclease EcoRI site GAA TTC was introduced. The PCR reaction was performed in a PCR thermocycler (Biometra T3) under the following conditions. The sequences of the primers used were shown in Table 4.

| 95° C. denaturation 10 min | 1 cycle |
|---|---|
| 95° C. denaturation 1.5 min | 20 cycle |
| 58° C. annealing 1.5 min | |
| 72° C. elongation 1.7 min | |
| 72° C. elongation 10 min | 1 cycle |

The amplification products were DNA fragments of about 1600 bp, 1200 bp and 600 bp in length, respectively.

The amplification products as obtained above were linked into commercially available pMD 18-T vector (produced by TAKARA Co.), respectively, and designated as pMD 18-T-M2e-L as well as pMD 18-T-CRM197, pMD 18-T-389 and pMD 18-T-A, respectively. As identified by NdeI/BamHI and BamHI/EcoRI enzyme cleavage, respectively, the positive clones pMD 18-T-CRM197, pMD 18-T-389, pMD 18-T-A, and pMD 18-T-M2e-L were obtained.

As confirmed by M13(+) primer, correct nucleotide sequences of interest were inserted into the obtained plasmids pMD 18-T-CRM197, pMD 18-T-389, pMD 18-T-A, and pMD 18-T-M2e-L, respectively.

The plasmid pMD 18-T-M2e-L was digested by NdeI/BamHI enzyme. The fragments obtained by enzyme cleavage were then linked into the prokaryotic expression vector pTO-T7 digested by NdeI/BamHI enzyme (Luo Wenxin et al., Chinese Journal of Biotechnology, 2000, 16:53-57), and was transformed into E. coli ER2566 (purchased from Invitrogen Co.); after extraction of plasmids, as identified by NdeI/BamHI enzyme cleavage, the positive plasmid pTO-T7-M2e-L, into which the fragment M2e-L was inserted, was obtained.

pTO-T7-M2e-L, pMD 18-T-CRM197, pMD 18-T-389 and pMD 18-T-A were digested by BamHI/EcoRI enzyme. The obtained fragments CRM197, 389 and A were linked into the vector pTO-T7-M2e-L digested by BamHI/EcoRI enzyme, respectively. As identified by NdeI/EcoRI enzyme cleavage, the positive expression vectors pTO-T7-M2e-L-CRM197, pTO-T7-M2e-L-389, and pTO-T7-M2e-L-A, into which M2e-L-CRM197 (SEQ ID NO:39, 40), M2e-L-389 (SEQ ID NO:41, 42), and M2e-L-A (SEQ ID NO:43, 44) were inserted respectively, were obtained.

The sequences of the primers used in the Example are listed in Table 4.

were separately used to transform 40 µl. L competent E. coli ER2566 (purchased from Invitrogen) prepared by the Calcium chloride method, and then the bacteria were plated on solid LB medium (the components of the LB medium: 10 g/L peptone, 5 g/L yeast powder, and 10 g/L NaCl, the same below) containing kanamycin (at a final concentration of 100 mg/ml, the same below). The plates were statically incubated at 37° C. for about 10-12 h until individual colonies could be observed clearly. Individual colonies from the plates were transferred to a tube containing 4 ml liquid LB medium containing kanamycin. The cultures were incubated in a shaking incubator at 180 rpm for 10 h at 37° C., and then 1 ml bacterial solution was taken and stored at −70° C.

Example 7. The Expression, Isolation and Renaturation of the Fusion Proteins Constructed in Example 6

5 µL bacterial solution, taken from an ultra low temperature freezer at −70° C., was seeded to 5 mL liquid LB medium containing kanamycin, and then was cultured at 37° C., 180 rpm under shaking until OD600 reached about 0.5. The resultant solution was transferred to 500 ml LB medium containing kanamycin, and then was cultured at 37° C., 180

TABLE 4

Primer sequences

| SEQ ID NO: | Primer names | Primer sequences (5'-3') |
| --- | --- | --- |
| 45 | CRM197 F1 | CATATGGGCGCTGATGATGTTGTTGATTCTTCTAAATCTTTTGTGATGGAA |
| 46 | CRM197-linker R1 | GGATCCGCTGCCACCGCCACCGCTGCCACCGCCACCGCTTTTGAT |
| 47 | 389-linker R1 | GGATCCGCTGCCACCGCCACCGCTGCCACCGCCACCAAATGGTTG |
| 48 | A-linker R1 | GGATCCGCTGCCACCGCCACCGCTGCCACCGCCACCACGATTTCC |
| 49 | M2e F1 | GGATCCATGAGTCTTCTAACCGAGGTCGAAACGCCT |
| 50 | M2e R | GAATTCTTAATCACTTGAACCGTTGCATCTGCACCCCCA |
| 51 | M2e F2 | CATATGATGAGTCTTCTAACCGAGGTCGAAACGCCT |
| 52 | M2e-Linker R | GGATCCGCTGCCACCGCCACCGCTGCCACCGCCACCATCACTTGA |
| 53 | CRM197 F2 | GGATCCGGCGCTGATGATGTTGTTGATTCTTCTAAATCTTTTGTGATGGAA |
| 54 | CRM197 R2 | GAATTCTAAGCTTTTGATTTCAAAAAATAGCGATAGCTTAGA |
| 55 | 389 R | GAATTCTAAAAATGGTTGCGTTTTATGCCCCGGAGAATACGC |
| 56 | A R | GAATTCTAAACGATTTCCTGCACAGGCTTGAGCCATATACTC |

1 µL of plasmids pTO-T7-CRM197-L-M2e, pTO-T7-389-L-M2e, pTO-T7-A-L-M2e, pTO-T7-M2e-L-CRM197, pTO-T7-M2e-L-389 and pTO-T7-M2e-L-A (0.15 mg/ml) rpm under shaking for 4-5 h. When OD600 reached about 1.5, IPTG was added to a final concentration of 0.4 mM, and the bacteria were induced under shaking at 37° C. for 4 h.

After induction, centrifugation was performed at 8000 g for 5 min to collect the bacteria, and then the bacteria was re-suspended in a lysis solution at a ratio of 1 g bacteria to 10 mL lysis solution (20 mM Tris buffer pH7.2, 300 mM NaCl), in ice-bath. The bacteria was treated with a sonicator (Sonics VCX750 Type Sonicator) (conditions: operating time 15 min, pulse 2s, intermission 4s, output power 55%). The bacterial lysate was centrifuged at 12000 rpm, 4° C. for 5 min (the same below), and the supernatant and the precipitate (i.e. inclusion body) after disrupting the bacteria by ultrasonication were collected, respectively. 2% Triton-100 of the same volume was used for washing the precipitate, the result mixture was under vibration for 30 min, centrifuged, and the supernatant was discarded. The precipitate was re-suspended in Buffer I (20 mM Tris-HCl pH8.0, 100 mM NaCl, 5 mM EDTA), under vibration for 30 min, centrifuged, and the supernatant was discarded. The precipitate was then re-suspended in 2M urea, under vibration at 37° C. for 30 min, centrifuged, and the supernatant and the precipitate were obtained. The supernatant was kept; and the precipitate was re-suspended in 4M urea in the same volume, under vibration at 37° C. for 30 min, and centrifuged at 12000 rpm, 4° C. for 15 min to obtain the supernatant and precipitate. The supernatant (i.e. the 4M urea-dissolved supernatant) was kept; and the precipitate was further in re-suspended in 8M urea in the same volume, under vibration at 37° C. for 30 min, and centrifuged, and the supernatant (i.e. the 8M urea-dissolved supernatant) was kept.

The fractions obtained were analyzed by SDS-PAGE (Coomassie brilliant blue staining was used for visualization, the same below, see the methods in The Molecular Cloning Experiment Guide, $2^{nd}$ edition). The results showed that the fusion proteins were expressed in inclusion bodies (see FIGS. 10A and 10B), CRM197-L-M2e, 389-L-M2e, M2e-L-CRM197 and M2e-L-389 were mainly dissolved in 8M urea, and A-L-M2e and M2e-L-A were mainly dissolved in 4M urea. The 4M urea-dissolved supernatants containing A-L-M2e or M2e-L-A or the 8M urea-dissolved supernatants containing CRM197-L-M2e, 389-L-M2e, M2e-L-CRM197 or M2e-L-389, were dialyzed to PBS, respectively, to get the fusion proteins with a purity of about 80% (see FIGS. 10C-10F).

Example 8. Analysis of Properties of the Fusion Proteins Constructed in Example 6

Determination of the Reactivity of the Fusion Proteins with Antibodies by Western Blotting The reactivity of the fusion proteins with influenza virus M2e monoclonal antibody 5D1 and CRM197 monoclonal antibody 1E6 (prepared in the laboratory) were determined by Western blotting. The dialyzed and renatured samples were transferred to nitrocellulose membrane for blotting after SDS-PAGE separation; 5% skimmed milk was used to block the membrane for 2 h, and then the monoclonal antibody 5D1 diluted at 1:500 was added. The reaction was carried out for 1 h. The membrane was then washed with TNT (50 mmol/L Tris.Cl (pH 7.5), 150 mmol/L NaCl, 0.05% Tween 20) for three times, 10 min for each time. Goat Anti-mouse alkaline phosphatase (KPL product) was then added. The reaction was carried out for 1 h, and the membrane was then washed with TNT for three times, 10 min for each time. NBT and BCIP (PROTOS product) were used for visualization. The results, as determined by Western blotting using the fusion proteins and influenza virus M2e monoclonal antibody 5D1 (FIGS. 11A-11D) or CRM197 monoclonal antibody 1E6 (FIGS. 11E-11H), were shown in FIG. 11. The results showed that all the tested fusion proteins had significant reactivity with influenza virus M2e-specific monoclonal antibody 5D1 and CRM197 specific monoclonal antibody 1E6.

Determination of the Reactivity of the Fusion Proteins with Various M2e Specific Monoclonal Antibodies and CRM197 Specific Antibody by ELISA The reactivity of the fusion proteins and the control protein GST-M2e with various M2e specific antibodies and CRM197 specific monoclonal antibody 1E6 (the antibodies used in the experiment were known in the prior art, or commercially available or prepared in the laboratory) was determined by indirect ELISA. For example, O19 antibody is a protective antibody against influenza known in the prior art (see, Fu et al., Virology, 2009, 385:218-226). The dialyzed and renatured samples were diluted in 1×PBS (1 μg/ml), and then were added to 96-well microplate (Beijing Wantai Co.) at 100 μl/well and incubated at 37° C. for 2 h. The coating solution was discarded, the plate was washed with PBST (PBS+0.05% TWEEN® 20) once, and then the blocking solution (2% gelatin, 5% Casein, 1% PROCLIN® 300, in PBS) was added at 180 μl/well and incubated at 37° C. for 2 h. The blocking solution was discarded when the detection was performed, and the anti-M2e antibody or CRM197 antibody diluted at a certain ratio (0.002 mg/ml was used as the initial concentration for 2-fold gradient dilution) was added at 100 μl/well. The mixture was incubated at 37° C. for 1 h. The plate was washed with PBST for five times, HRP-labeled Goat anti Mouse (KPL product) (1:5000) was then added at 100 μl/well and was incubated at 37° C. for 30 min. The plate was washed with PBST for five times, HRP substrate (Beijing Wantai Co.) was then added at 100 μl/well and was incubated at 37° C. for 15 min. 2M sulphuric acid was added at 50 μl/well to stop the reaction, and Microplate reader (Sunrise Type, product from Tecan Co.) was then used to read OD450/620 value. The results of the ELISA using the fusion proteins with the antibodies were shown in FIGS. 12A and 12B. The results showed that as compared to M2e protein alone, the reactivity of M2e protein with various anti-M2e specific monoclonal antibodies was retained or enhanced after its fusion with CRM197 or a fragment thereof.

Analysis of Sedimentation Velocity (SV) of the Fusion Proteins

The apparatus used in the experiment was US Beckman XL-A analytic supercentrifuge, which was equipped with an optical detection system and An-50Ti and An-60Ti rotators. The Sedimentation Velocity (SV) method (c(s) algorithm, see P. Schuck et al., Biophys J 78: 1606-1619(2000)) was used to analyze the sedimentation coefficient of the fusion proteins. The analytic results were shown in FIGS. 13A-13F. The results showed that among the fusion proteins constructed in Example 6, A-L-M2e and M2e-L-A were mainly present in a form of monomer and tetramer; and 389-L-M2e was mainly present in a form of dimer and polymer; M2e-L-389 was mainly present in a form of monomer and polymer; CRM197-L-M2e was mainly present in a form of dimer and polymer; and M2e-L-CRM197 was mainly present in a form of monomer and polymer.

Example 9. Analysis of Immunogenicity of the Fusion Proteins Constructed in Example 6

The mice used in the experiment were female, 6-week old BALB/C mice. By using aluminum adjuvant, mice were immunized by intraperitoneal injection of the fusions proteins as constructed in Example 6 and renatured to PBS and the control protein GST-M2e, respectively. The injection volume was 1 ml, and two dose groups (a 5 μg-dose group or a 0.5 μg-dose group) were used. The primary immunization was performed at week 0, and booster immunization was performed at week 2 and 4.

GST-M2e was used to coat a plate, and the antibody titers in serum as induced by the fusion proteins and control protein, were measured by similar indirect ELISA assay as described above. The detection results of the serum antibody titers within 4 months after immunization were shown in FIGS. 14A and 14B. The results showed that after the second booster immunization, immunogenicity of the constructed fusion proteins was significantly higher than the antigen protein (GST-M2e) alone, indicating that the CRM197 of the invention or a fragment thereof (no matter being located at the N-terminus or C-terminus of the fusion protein) significantly enhanced immunogenicity of the antigen protein fused therewith, and could be used as intramolecular adjuvant.

Although the specific embodiments of the invention have been described in details, those skilled in the art would understand that, according to the teachings disclosed in the specification, various modifications and changes can be made without departing from the sprit or scope of the invention as generally described, and that such modifications and changes are within the scope of the present invention. The scope of the present invention is given by the appended claims and any equivalents thereof.

The invention claimed is:

1. A fusion protein comprising a fragment of CRM197 and a target protein, wherein said fragment of CRM197 enhances immunogenicity of the target protein, wherein said fragment of CRM197 consists of amino acids 1-389 of SEQ ID NO:2, and wherein said fragment of CRM197 is linked to the N-terminus and/or C-terminus of the target protein, optionally via a linker.

2. The fusion protein of claim 1, wherein the target protein is HEV capsid protein or an immunogenic fragment thereof.

3. The fusion protein of claim 2, wherein the immunogenic fragment of HEV capsid protein comprises or is HEV-239 (aa 368-606 of HEV capsid protein), E2 (aa 394-606 of HEV capsid protein) or E2s (aa 455-606 of HEV capsid protein).

4. The fusion protein of claim 2, wherein the fusion protein comprises (a) the fragment of CRM197, and (b) HEV capsid protein or the immunogenic fragment of HEV capsid protein; wherein (a) and (b) are linked together, optionally via a linker.

5. The fusion protein of claim 2, wherein the fusion protein has an amino acid sequence as set forth in SEQ ID NO: 8, 10, or 16.

6. The fusion protein of claim 1, wherein the target protein is influenza virus M2 protein or an immunogenic fragment thereof.

7. The fusion protein of claim 6, wherein the immunogenic fragment of M2 protein comprises or is M2e (aa 1-24 of M2 protein).

8. The fusion protein of claim 6, wherein the fusion protein comprises (a) the fragment of CRM197, and (b) influenza virus M2 protein or the immunogenic fragment of M2 protein; wherein (a) and (b) are linked together, optionally via a linker.

9. The fusion protein of claim 6, wherein the fusion protein has an amino acid sequence as set forth in SEQ ID NO: 36 or 42.

10. A polynucleotide encoding the fusion protein of claim 1.

11. An expression vector comprising the polynucleotide of claim 10.

12. A host cell comprising the polynucleotide of claim 10.

13. A pharmaceutical composition or vaccine comprising the fusion protein of claim 1 and a pharmaceutically acceptable carrier and/or excipient.

14. A method for preventing and/or treating HEV infection or a disease associated with HEV infection, comprising administering an effective amount of the fusion protein of claim 4 or a pharmaceutical composition comprising the fusion protein.

15. The method of claim 14, wherein the disease associated with HEV infection is Hepatitis E.

16. A method for preventing and/or treating influenza virus infection or a disease associated with influenza virus infection, comprising administering an effective amount of the fusion protein of claim 8 or a pharmaceutical composition comprising the fusion protein.

17. The method of claim 16, wherein the disease associated with influenza virus infection is influenza.

* * * * *

SEQUENCE LISTING

```
<160> NUMBER OF SEQ ID NOS: 60

<210> SEQ ID NO 1
<211> LENGTH: 1605
<212> TYPE: DNA
<213> ORGANISM: Artificial Sequence
<220> FEATURE:
<223> OTHER INFORMATION: CRM197

<400> SEQUENCE: 1
ggcgctgatg atgttgttga ttcttctaaa tcttttgtga tggaaaactt ttcttcgtac      60
cacgggacta aacctggtta tgtagattcc attcaaaaag gtatacaaaa gccaaaatct     120
ggtacacaag gaaattatga cgatgattgg aaagagtttt atagtaccga caataaatac     180
gacgctgcgg gatactctgt agataatgaa aacccgctct ctggaaaagc tggaggcgtg     240
gtcaaagtga cgtatccagg actgacgaag gttctcgcac taaaagtgga taatgccgaa     300
actattaaga aagagttagg tttaagtctc actgaaccgt tgatggagca agtcggaacg     360
gaagagttta tcaaaaggtt cggtgatggt gcttcgcgtg tagtgctcag ccttcccttc     420
gctgagggga gttctagcgt tgaatatatt aataactggg aacaggcgaa agcgttaagc     480
gtagaacttg agattaattt tgaaacccgt ggaaaacgtg gccaagatgc gatgtatgag     540
tatatggctc aagcctgtgc aggaaatcgt gtcaggcgat cagtaggtag ctcattgtca     600
tgcataaatc ttgattggga tgtcataagg gataaaacta agacaaagat agagtctttg     660
aaagagcatg gccctatcaa aaataaaatg agcgaaagtc ccaataaaac agtatctgag     720
gaaaaagcta acaatacct agaagaattt catcaaacgg cattagagca tcctgaattg     780
tcagaactta aaaccgttac tgggaccaat cctgtattcg ctggggctaa ctatgcggcg     840
tgggcagtaa acgttgcgca agttatcgat agcgaaacag ctgataattt ggaaaagaca     900
actgctgctc tttcgatact tcctggtatc ggtagcgtaa tgggcattgc agacggtgcc     960
gttcaccaca atacagaaga gatagtggca caatcaatag ctttatcgtc tttaatggtt    1020
gctcaagcta ttccattggt aggagagcta gttgatattg gtttcgctgc atataatttt    1080
gtagagagta ttatcaattt atttcaagta gttcataatt cgtataatcg tcccgcgtat    1140
tctccggggc ataaaacgca accatttctt catgacgggt atgctgtcag ttggaacact    1200
gttgaagatt cgataatccg aactggtttt caaggggaga gtgggcacga cataaaaatt    1260
actgctgaaa taccccgct tccaatcgcg ggtgtcctac taccgactat tcctggaaag    1320
ctggacgtta ataagtccaa gactcatatt tccgtaaatg gtcggaaaat aaggatgcgt    1380
tgcagagcta tagacggtga tgtaactttt tgtcgcccta aatctcctgt ttatgttggt    1440
aatggtgtgc atgcgaatct tcacgtggca tttcacagaa gcagctcgga gaaaattcat    1500
```

```
tctaatgaaa tttcgtcgga ttccataggc gttcttgggt accagaaaac agtagatcac    1560
accaaggtta attctaagct atcgctattt tttgaaatca aaagc                    1605

<210> SEQ ID NO 2
<211> LENGTH: 535
<212> TYPE: PRT
<213> ORGANISM: Artificial Sequence
<220> FEATURE:
<223> OTHER INFORMATION: CRM197

<400> SEQUENCE: 2

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
```

```
            340                 345                 350
Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
        530                 535
```

<210> SEQ ID NO 3
<211> LENGTH: 2292
<212> TYPE: DNA
<213> ORGANISM: Artificial Sequence
<220> FEATURE:
<223> OTHER INFORMATION: CRM197-L-E2

<400> SEQUENCE: 3

```
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagagt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa aacagtatct     720
gaggaaaaag ctaaacaata cctagaagaa tttcatcaaa cggcattaga gcatcctgaa     780
ttgtcagaac ttaaaaccgt tactgggacc aatcctgtat cgctggggc taactatgcg     840
gcgtgggcag taacgttgc gcaagttatc gatagcgaaa cagctgataa tttggaaaag     900
acaactgctg ctcttcgat acttcctggt atcggtagcg taatgggcat tgcagacggt     960
```

```
gccgttcacc acaatacaga agagatagtg gcacaatcaa tagctttatc gtctttaatg   1020
gttgctcaag ctattccatt ggtaggagag ctagttgata ttggtttcgc tgcatataat   1080
tttgtagaga gtattatcaa tttatttcaa gtagttcata attcgtataa tcgtcccgcg   1140
tattctccgg ggcataaaac gcaaccattt cttcatgacg ggtatgctgt cagttggaac   1200
actgttgaag attcgataat ccgaactggt tttcaagggg agagtgggca cgacataaaa   1260
attactgctg aaaataccc gcttccaatc gcgggtgtcc tactaccgac tattcctgga   1320
aagctggacg ttaataagtc caagactcat atttccgtaa atggtcggaa ataaggatg    1380 cgttgcagag ctatagacgg tgatgtaact ttttgtcgcc ctaaatctcc tgtttatgtt   1440
ggtaatggtg tgcatgcgaa tcttcacgtg gcatttcaca gaagcagctc ggagaaaatt   1500
cattctaatg aaatttcgtc ggattccata ggcgttcttg gtaccagaa acagtagat    1560 cacaccaagg ttaattctaa gctatcgcta ttttttgaaa tcaaaagcgg tggcggtggc   1620
agcggtggcg gtggcagcgg tggcggtgga tcccagctgt tctactctcg tcccgtcgtc   1680
tcagccaatg gcgagccgac tgttaagctt tatacatctg tagagaatgc tcagcaggat   1740
aagggtattg caatcccgca tgacatcgac ctcggggagt ctcgtgtagt tattcaggat   1800
tatgacaacc aacatgagca ggaccgaccg acaccttccc cagccccatc gcgcccttt    1860 tctgtcctcc gagctaatga tgtgctttgg ctttctctca ccgctgccga gtatgaccag   1920
tccacttacg gctcttcgac cggcccagtc tatgtctctg actctgtgac cttggttaat   1980
gttgcgaccg gcgcgcaggc cgttgcccgg tcactcgact ggaccaaggt cacacttgat   2040
ggtcgccccc tttccaccat ccagcagcat tcaaagacct tctttgtcct gccgctccgc   2100
ggtaagctct ccttttggga ggcaggtact actaaagccg gtaccctta taattataac    2160 accactgcta gtgaccaact gctcgttgag aatgccgctg gcatcgggt tgctatttcc   2220 acttacacca ctagcctggg tgctggcccc gtctctattt ccgcggttgc tgttttagcc   2280 cccctccgc gc                                                        2292
```

<210> SEQ ID NO 4
<211> LENGTH: 764
<212> TYPE: PRT
<213> ORGANISM: Artificial Sequence
<220> FEATURE:
<223> OTHER INFORMATION: CRM197-L-E2

<400> SEQUENCE: 4

```
Met Gly Ala Asp Asp Val Val Asp Ser Ser Lys Ser Phe Val Met Glu
1               5                  10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
```

```
            115                 120                 125
Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
    450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser Gly Gly Gly Ser Gly Gly Gly
    530                 535                 540
```

```
Gly Ser Gly Gly Gly Ser Gln Leu Phe Tyr Ser Arg Pro Val Val
545                 550                 555                 560

Ser Ala Asn Gly Glu Pro Thr Val Lys Leu Tyr Thr Ser Val Glu Asn
                565                 570                 575

Ala Gln Gln Asp Lys Gly Ile Ala Ile Pro His Asp Ile Asp Leu Gly
            580                 585                 590

Glu Ser Arg Val Val Ile Gln Asp Tyr Asp Asn Gln His Glu Gln Asp
        595                 600                 605

Arg Pro Thr Pro Ser Pro Ala Pro Ser Arg Pro Phe Ser Val Leu Arg
    610                 615                 620

Ala Asn Asp Val Leu Trp Leu Ser Leu Thr Ala Ala Glu Tyr Asp Gln
625                 630                 635                 640

Ser Thr Tyr Gly Ser Ser Thr Gly Pro Val Tyr Val Ser Asp Ser Val
                645                 650                 655

Thr Leu Val Asn Val Ala Thr Gly Ala Gln Ala Val Ala Arg Ser Leu
            660                 665                 670

Asp Trp Thr Lys Val Thr Leu Asp Gly Arg Pro Leu Ser Thr Ile Gln
        675                 680                 685

Gln His Ser Lys Thr Phe Phe Val Leu Pro Leu Arg Gly Lys Leu Ser
    690                 695                 700

Phe Trp Glu Ala Gly Thr Thr Lys Ala Gly Tyr Pro Tyr Asn Tyr Asn
705                 710                 715                 720

Thr Thr Ala Ser Asp Gln Leu Leu Val Glu Asn Ala Ala Gly His Arg
                725                 730                 735

Val Ala Ile Ser Thr Tyr Thr Thr Ser Leu Gly Ala Gly Pro Val Ser
            740                 745                 750

Ile Ser Ala Val Ala Val Leu Ala Pro Pro Arg
    755                 760

<210> SEQ ID NO 5
<211> LENGTH: 2109
<212> TYPE: DNA
<213> ORGANISM: Artificial Sequence
<220> FEATURE:
<223> OTHER INFORMATION: CRM197-L-E2s

<400> SEQUENCE: 5
atgggcgctg atgatgttgt tgattcttct aaatcttttg tgatggaaaa cttttcttcg      60
taccacggga ctaaacctgg ttatgtagat ccattcaaa aaggtataca aaagccaaaa      120
tctggtacac aaggaaatta tgacgatgat tggaaagagt tttatagtac cgacaataaa      180
tacgacgctg cgggatactc tgtagataat gaaaacccgc tctctggaaa agctggaggc      240
gtggtcaaag tgacgtatcc aggactgacg aaggttctcg cactaaaagt ggataatgcc      300
gaaactatta gaaagagtt aggtttaagt ctcactgaac cgttgatgga gcaagtcgga      360
acggaagagt ttatcaaaag gttcggtgat ggtgcttcgc gtgtagtgct cagccttccc      420
ttcgctgagg ggagttctag cgttgaatat attaataact gggaacaggc gaaagcgtta      480
agcgtagaac ttgagattaa ttttgaaacc cgtggaaaac gtggccaaga tgcgatgtat      540
gagtatatgg ctcaagcctg tgcaggaaat cgtgtcaggc gatcagtagg tagctcattg      600
tcatgcataa atcttgattg ggatgtcata agggataaaa ctaagacaaa gatagagtct      660
ttgaaagagc atgccctat caaaataaa atgagcgaaa gtcccaataa aacagtatct      720
gaggaaaaag ctaaacaata cctagaagaa tttcatcaaa cggcattaga gcatcctgaa      780
```

```
ttgtcagaac ttaaaaccgt tactgggacc aatcctgtat tcgctggggc taactatgcg    840
gcgtgggcag taacgttgc gcaagttatc gatagcgaaa cagctgataa tttggaaaag    900
acaactgctg ctctttcgat acttcctggt atcggtagcg taatgggcat tgcagacggt    960
gccgttcacc acaatacaga agagatagtg cacaatcaa tagctttatc gtctttaatg   1020
gttgctcaag ctattccatt ggtaggagag ctagttgata ttggtttcgc tgcatataat   1080
tttgtagaga gtattatcaa tttatttcaa gtagttcata attcgtataa tcgtcccgcg   1140
tattctccgg ggcataaaac gcaaccattt cttcatgacg ggtatgctgt cagttggaac   1200
actgttgaag attcgataat ccgaactggt tttcaagggg agagtgggca cgacataaaa   1260
attactgctg aaaataccc gcttccaatc gcgggtgtcc tactaccgac tattcctgga   1320
aagctggacg ttaataagtc caagactcat atttccgtaa atggtcggaa ataaggatg    1380
cgttgcagag ctatagacgg tgatgtaact ttttgtcgcc ctaaatctcc tgtttatgtt   1440
ggtaatggtg tgcatgcgaa tcttcacgtg gcatttcaca gaagcagctc ggagaaaatt   1500
cattctaatg aaatttcgtc ggattccata ggcgttcttg gtaccagaa acagtagat    1560
cacaccaagg ttaattctaa gctatcgcta tttttgaaa tcaaaagcgg tggcggtggc   1620
agcggtggcg gtggcagcgg tggcggtgga tcctccccag ccccatcgcg cccttttct    1680
gtcctccgag ctaatgatgt gctttggctt tctctcaccg ctgccgagta tgaccagtcc   1740
acttacggct cttcgaccgg cccagtctat gtctctgact ctgtgacctt ggttaatgtt   1800
gcgaccagcg cgcaggccgt tgcccggtca ctcgactgga ccaaggtcac acttgatggt   1860
cgccccttt ccaccatcca gcagcattca aagaccttct ttgtcctgcc gctccgcggt   1920
aagctctcct tttgggaggc aggtactact aaagccgggt acccttataa ttataacacc   1980
actgctagtg accaactgct cgttgagaat gccgctgggc atcgggttgc tatttccact   2040
tacaccacta gcctgggtgc tggccccgtc tctatttccg cggttgctgt tttagccccc   2100
cctccgcgc                                                           2109
```

<210> SEQ ID NO 6
<211> LENGTH: 703
<212> TYPE: PRT
<213> ORGANISM: Artificial Sequence
<220> FEATURE:
<223> OTHER INFORMATION: CRM197-L-E2s

<400> SEQUENCE: 6

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

```
Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
370                 375                 380

His Lys Thr Gln Pro Phe Leu His Asp Gly Tyr Ala Val Ser Trp Asn
385                 390                 395                 400

Thr Val Glu Asp Ser Ile Ile Arg Thr Gly Phe Gln Gly Glu Ser Gly
                405                 410                 415

His Asp Ile Lys Ile Thr Ala Glu Asn Thr Pro Leu Pro Ile Ala Gly
            420                 425                 430

Val Leu Leu Pro Thr Ile Pro Gly Lys Leu Asp Val Asn Lys Ser Lys
        435                 440                 445

Thr His Ile Ser Val Asn Gly Arg Lys Ile Arg Met Arg Cys Arg Ala
450                 455                 460

Ile Asp Gly Asp Val Thr Phe Cys Arg Pro Lys Ser Pro Val Tyr Val
465                 470                 475                 480

Gly Asn Gly Val His Ala Asn Leu His Val Ala Phe His Arg Ser Ser
                485                 490                 495

Ser Glu Lys Ile His Ser Asn Glu Ile Ser Ser Asp Ser Ile Gly Val
            500                 505                 510

Leu Gly Tyr Gln Lys Thr Val Asp His Thr Lys Val Asn Ser Lys Leu
        515                 520                 525

Ser Leu Phe Phe Glu Ile Lys Ser Gly Gly Gly Ser Gly Gly Gly Gly
530                 535                 540
```

| | | | | | | | | | | | | | | |
|---|---|---|---|---|---|---|---|---|---|---|---|---|---|---|
|Gly|Ser|Gly|Gly|Gly|Ser|Ser|Pro|Ala|Pro|Ser|Arg|Pro|Phe|Ser|
|545| | | |550| | | |555| | | |560| | |

| | | | | | | | | | | | | | |
|---|---|---|---|---|---|---|---|---|---|---|---|---|---|
|Val|Leu|Arg|Ala|Asn|Asp|Val|Leu|Trp|Leu|Ser|Leu|Thr|Ala|Ala|Glu|
| | | | |565| | | |570| | | |575| | |

Tyr Asp Gln Ser Thr Tyr Gly Ser Ser Thr Gly Pro Val Tyr Val Ser
            580                 585                 590

Asp Ser Val Thr Leu Val Asn Val Ala Thr Ser Ala Gln Ala Val Ala
            595                 600             605

Arg Ser Leu Asp Trp Thr Lys Val Thr Leu Asp Gly Arg Pro Leu Ser
        610                 615             620

Thr Ile Gln Gln His Ser Lys Thr Phe Phe Val Leu Pro Leu Arg Gly
625                 630                 635                 640

Lys Leu Ser Phe Trp Glu Ala Gly Thr Thr Lys Ala Gly Tyr Pro Tyr
                645                 650                 655

Asn Tyr Asn Thr Thr Ala Ser Asp Gln Leu Leu Val Glu Asn Ala Ala
            660                 665             670

Gly His Arg Val Ala Ile Ser Thr Tyr Thr Thr Ser Leu Gly Ala Gly
        675                 680             685

Pro Val Ser Ile Ser Ala Val Ala Val Leu Ala Pro Pro Arg
    690                 695             700

<210> SEQ ID NO 7
<211> LENGTH: 1854
<212> TYPE: DNA
<213> ORGANISM: Artificial Sequence
<220> FEATURE:
<223> OTHER INFORMATION: 389-L-E2

<400> SEQUENCE: 7

```
atgggcgctg atgatgttgt tgattcttct aaatctttg tgatggaaaa cttttcttcg      60
taccacggga ctaaacctgg ttatgtagat tccattcaaa aaggtataca aaagccaaaa    120
tctggtacac aaggaaatta tgacgatgat tggaaagagt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta gaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgaggaaat cgtgtcaggc gatcagtagg tagctcattg    600
tcatgcataa atcttgattg ggatgtcata agggataaaa ctaagacaaa gatagagtct    660
ttgaaagagc atggccctat caaaaataaa atgagcgaaa gtcccaataa aacagtatct    720
gaggaaaaag ctaaacaata cctagaagaa tttcatcaaa cggcattaga gcatcctgaa    780
ttgtcagaac ttaaaaccgt tactgggacc aatcctgtat cgctggggc taactatgcg    840
gcgtgggcag taacgttgc gcaagttatc gatagcgaaa cagctgataa tttggaaaag    900
acaactgctg ctctttcgat acttcctggt atcggtagcg taatgggcat tgcagacggt    960
gccgttcacc acaatacaga agagatagtg gcacaatcaa tagctttatc gtctttaatg   1020
gttgctcaag ctattccatt ggtaggagag ctagttgata ttggtttcgc tgcatataat   1080
tttgtagaga gtattatcaa tttatttcaa gtagttcata attcgtataa tcgtcccgcg   1140
tattctccgg ggcataaaac gcaaccattt ggtggcggtg gcagcggtgg cggtggcagc   1200
```

-continued

```
ggtggcggtg gatcccagct gttctactct cgtcccgtcg tctcagccaa tggcgagccg    1260
actgttaagc tttatacatc tgtagagaat gctcagcagg ataagggtat tgcaatcccg    1320
catgacatcg acctcgggga gtctcgtgta gttattcagg attatgacaa ccaacatgag    1380
caggaccgac cgacaccttc cccagcccca tcgcgccctt tttctgtcct ccagctaat    1440 gatgtgcttt ggctttctct caccgctgcc gagtatgacc agtccactta cggctcttcg    1500
accggcccag tctatgtctc tgactctgtg accttggtta atgttgcgac cggcgcgcag    1560
gccgttgccc ggtcactcga ctggaccaag gtcacacttg atggtcgccc cctttccacc    1620
atccagcagc attcaaagac cttctttgtc ctgccgctcc gcggtaagct ctccttttgg    1680
gaggcaggta ctactaaagc cgggtaccct tataattata acaccactgc tagtgaccaa    1740
ctgctcgttg agaatgccgc tgggcatcgg gttgctattt ccacttacac cactagcctg    1800
ggtgctggcc ccgtctctat ttccgcggtt gctgttttag ccccccctcc gcgc          1854
```

<210> SEQ ID NO 8
<211> LENGTH: 618
<212> TYPE: PRT
<213> ORGANISM: Artificial Sequence
<220> FEATURE:
<223> OTHER INFORMATION: 389-L-E2

<400> SEQUENCE: 8

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
```

```
            245                 250                 255
Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
        370                 375                 380

His Lys Thr Gln Pro Phe Gly Gly Gly Ser Gly Gly Gly Ser
385                 390                 395                 400

Gly Gly Gly Gly Ser Gln Leu Phe Tyr Ser Arg Pro Val Val Ser Ala
                405                 410                 415

Asn Gly Glu Pro Thr Val Lys Leu Tyr Thr Ser Val Glu Asn Ala Gln
            420                 425                 430

Gln Asp Lys Gly Ile Ala Ile Pro His Asp Ile Asp Leu Gly Glu Ser
        435                 440                 445

Arg Val Val Ile Gln Asp Tyr Asp Asn Gln His Glu Gln Asp Arg Pro
    450                 455                 460

Thr Pro Ser Pro Ala Pro Ser Arg Pro Phe Ser Val Leu Arg Ala Asn
465                 470                 475                 480

Asp Val Leu Trp Leu Ser Leu Thr Ala Ala Glu Tyr Asp Gln Ser Thr
                485                 490                 495

Tyr Gly Ser Ser Thr Gly Pro Val Tyr Val Ser Asp Ser Val Thr Leu
            500                 505                 510

Val Asn Val Ala Thr Gly Ala Gln Ala Val Ala Arg Ser Leu Asp Trp
        515                 520                 525

Thr Lys Val Thr Leu Asp Gly Arg Pro Leu Ser Thr Ile Gln Gln His
    530                 535                 540

Ser Lys Thr Phe Phe Val Leu Pro Leu Arg Gly Lys Leu Ser Phe Trp
545                 550                 555                 560

Glu Ala Gly Thr Thr Lys Ala Gly Tyr Pro Tyr Asn Tyr Asn Thr Thr
                565                 570                 575

Ala Ser Asp Gln Leu Leu Val Glu Asn Ala Ala Gly His Arg Val Ala
            580                 585                 590

Ile Ser Thr Tyr Thr Thr Ser Leu Gly Ala Gly Pro Val Ser Ile Ser
        595                 600                 605

Ala Val Ala Val Leu Ala Pro Pro Arg
    610                 615
```

<210> SEQ ID NO 9
<211> LENGTH: 1671
<212> TYPE: DNA
<213> ORGANISM: Artificial Sequence
<220> FEATURE:
<223> OTHER INFORMATION: 389-L-E2s

<400> SEQUENCE: 9

```
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagagt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa acagtatct      720
gaggaaaaag ctaaacaata cctagaagaa tttcatcaaa cggcattaga gcatcctgaa     780
ttgtcagaac ttaaaaccgt tactgggacc aatcctgtat cgctggggc taactatgcg      840
gcgtgggcag taaacgttgc gcaagttatc gatagcgaaa cagctgataa tttggaaaag     900
acaactgctg ctctttcgat acttcctggt atcggtagcg taatgggcat gcagacggt      960
gccgttcacc acaatacaga agagatagtg gcacaatcaa tagctttatc gtctttaatg    1020
gttgctcaag ctattccatt ggtaggagag ctagttgata ttggtttcgc tgcatataat    1080
tttgtagaga gtattatcaa tttatttcaa gtagttcata attcgtataa tcgtcccgcg    1140
tattctccgg ggcataaaac gcaaccattt ggtggcggtg gcagcggtgg cggtggcagc    1200
ggtggcggtg gatcctcccc agccccatcg cgccttttt ctgtcctccg agctaatgat    1260
gtgctttggc tttctctcac cgctgccgag tatgaccagt ccacttacgg ctcttcgacc    1320
ggcccagtct atgtctctga ctctgtgacc ttggttaatg ttgcgaccag cgcgcaggcc    1380
gttgcccggt cactcgactg gaccaaggtc acacttgatg tcgcccccct ttccaccatc    1440
cagcagcatt caaagacctt ctttgtcctg ccgctccgcg gtaagctctc cttttgggag    1500
gcaggtacta ctaaagccgg gtaccttat aattataaca ccactgctag tgaccaactg    1560
ctcgttgaga atgccgctgg gcatcgggtt gctatttcca cttacaccac tagcctgggt    1620
gctggccccg tctctatttc gcggttgct gttttagccc ccctccgcg c              1671
```

<210> SEQ ID NO 10
<211> LENGTH: 557
<212> TYPE: PRT
<213> ORGANISM: Artificial Sequence
<220> FEATURE:
<223> OTHER INFORMATION: 389-L-E2s

<400> SEQUENCE: 10

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60
```

```
Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
                100                 105                 110

Glu Pro Leu Met Glu Gln Val Gly Thr Glu Glu Phe Ile Lys Arg Phe
                115                 120                 125

Gly Asp Gly Ala Ser Arg Val Val Leu Ser Leu Pro Phe Ala Glu Gly
                130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
                180                 185                 190

Arg Arg Ser Val Gly Ser Ser Leu Ser Cys Ile Asn Leu Asp Trp Asp
                195                 200                 205

Val Ile Arg Asp Lys Thr Lys Thr Lys Ile Glu Ser Leu Lys Glu His
                210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
                260                 265                 270

Val Phe Ala Gly Ala Asn Tyr Ala Ala Trp Ala Val Asn Val Ala Gln
                275                 280                 285

Val Ile Asp Ser Glu Thr Ala Asp Asn Leu Glu Lys Thr Thr Ala Ala
                290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
                340                 345                 350

Asp Ile Gly Phe Ala Ala Tyr Asn Phe Val Glu Ser Ile Ile Asn Leu
                355                 360                 365

Phe Gln Val Val His Asn Ser Tyr Asn Arg Pro Ala Tyr Ser Pro Gly
                370                 375                 380

His Lys Thr Gln Pro Phe Gly Gly Gly Ser Gly Gly Gly Gly Gly Ser
385                 390                 395                 400

Gly Gly Gly Gly Ser Ser Pro Ala Pro Ser Arg Pro Phe Ser Val Leu
                405                 410                 415

Arg Ala Asn Asp Val Leu Trp Leu Ser Leu Thr Ala Ala Glu Tyr Asp
                420                 425                 430

Gln Ser Thr Tyr Gly Ser Ser Thr Gly Pro Val Tyr Val Ser Asp Ser
                435                 440                 445

Val Thr Leu Val Asn Val Ala Thr Ser Ala Gln Ala Val Ala Arg Ser
                450                 455                 460

Leu Asp Trp Thr Lys Val Thr Leu Asp Gly Arg Pro Leu Ser Thr Ile
465                 470                 475                 480
```

```
Gln Gln His Ser Lys Thr Phe Phe Val Leu Pro Leu Arg Gly Lys Leu
            485                 490                 495

Ser Phe Trp Glu Ala Gly Thr Thr Lys Ala Gly Tyr Pro Tyr Asn Tyr
            500                 505                 510

Asn Thr Thr Ala Ser Asp Gln Leu Leu Val Glu Asn Ala Ala Gly His
            515                 520                 525

Arg Val Ala Ile Ser Tyr Thr Thr Ser Leu Gly Ala Gly Pro Val
            530                 535                 540

Ser Ile Ser Ala Val Ala Val Leu Ala Pro Pro Pro Arg
545                 550                 555
```

<210> SEQ ID NO 11
<211> LENGTH: 1257
<212> TYPE: DNA
<213> ORGANISM: Artificial Sequence
<220> FEATURE:
<223> OTHER INFORMATION: A-L-E2

<400> SEQUENCE: 11

```
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagagt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtggtggcg gtggcagcgg tggcggtggc     600
agcggtggcg gtggatccca gctgttctac tctcgtcccg tcgtctcagc caatggcgag     660
ccgactgtta agctttatac atctgtagag aatgctcagc aggataaggg tattgcaatc     720
ccgcatgaca tcgacctcgg ggagtctcgt gtagttattc aggattatga caaccaacat     780
gagcaggacc gaccgacacc ttccccagcc catcgcgcc ctttttctgt cctccgagct     840
aatgatgtgc tttggctttc tctcaccgct gccgagtatg accagtccac ttacggctct     900
tcgaccggcc cagtctatgt ctctgactct gtgaccttgg ttaatgttgc gaccggcgcg     960
caggccgttg cccggtcact cgactggacc aaggtcacac ttgatggtcg ccccctttcc    1020
accatccagc agcattcaaa gaccttcttt gtcctgccgc tccgcggtaa gctctccttt    1080
tgggaggcag gtactactaa agccgggtac ccttataatt ataacaccac tgctagtgac    1140
caactgctcg ttgagaatgc cgctgggcat cgggttgcta tttccactta caccactagc    1200
ctgggtgctg gccccgtctc tatttccgcg gttgctgttt tagcccccccc tccgcgc       1257
```

<210> SEQ ID NO 12
<211> LENGTH: 419
<212> TYPE: PRT
<213> ORGANISM: Artificial Sequence
<220> FEATURE:
<223> OTHER INFORMATION: A-L-E2

<400> SEQUENCE: 12

```
Met Gly Ala Asp Asp Val Val Asp Ser Ser Lys Ser Phe Val Met Glu
1               5                   10                  15
```

```
Asn Phe Ser Ser Tyr His Gly Thr Lys Pro Gly Tyr Val Asp Ser Ile
             20                  25                  30

Gln Lys Gly Ile Gln Lys Pro Lys Ser Gly Thr Gln Gly Asn Tyr Asp
             35                  40                  45

Asp Asp Trp Lys Glu Phe Tyr Ser Thr Asp Asn Lys Tyr Asp Ala Ala
 50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                 85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Gly
            180                 185                 190

Gly Gly Gly Ser Gly Gly Gly Ser Gly Gly Gly Ser Gln Leu
            195                 200                 205

Phe Tyr Ser Arg Pro Val Val Ser Ala Asn Gly Glu Pro Thr Val Lys
            210                 215                 220

Leu Tyr Thr Ser Val Glu Asn Ala Gln Gln Asp Lys Gly Ile Ala Ile
225                 230                 235                 240

Pro His Asp Ile Asp Leu Gly Glu Ser Arg Val Val Ile Gln Asp Tyr
                245                 250                 255

Asp Asn Gln His Glu Gln Asp Arg Pro Thr Pro Ser Pro Ala Pro Ser
            260                 265                 270

Arg Pro Phe Ser Val Leu Arg Ala Asn Asp Val Leu Trp Leu Ser Leu
            275                 280                 285

Thr Ala Ala Glu Tyr Asp Gln Ser Thr Tyr Gly Ser Ser Thr Gly Pro
290                 295                 300

Val Tyr Val Ser Asp Ser Val Thr Leu Val Asn Val Ala Thr Gly Ala
305                 310                 315                 320

Gln Ala Val Ala Arg Ser Leu Asp Trp Thr Lys Val Thr Leu Asp Gly
                325                 330                 335

Arg Pro Leu Ser Thr Ile Gln Gln His Ser Lys Thr Phe Phe Val Leu
            340                 345                 350

Pro Leu Arg Gly Lys Leu Ser Phe Trp Glu Ala Gly Thr Thr Lys Ala
            355                 360                 365

Gly Tyr Pro Tyr Asn Tyr Asn Thr Thr Ala Ser Asp Gln Leu Leu Val
            370                 375                 380

Glu Asn Ala Ala Gly His Arg Val Ala Ile Ser Thr Tyr Thr Thr Ser
385                 390                 395                 400

Leu Gly Ala Gly Pro Val Ser Ile Ser Ala Val Ala Val Leu Ala Pro
                405                 410                 415

Pro Pro Arg
```

<210> SEQ ID NO 13
<211> LENGTH: 1074
<212> TYPE: DNA
<213> ORGANISM: Artificial Sequence
<220> FEATURE:
<223> OTHER INFORMATION: A-L-E2s

<400> SEQUENCE: 13

```
atgggcgctg atgatgttgt tgattcttct aaatcttttg tgatggaaaa ctttcttcg      60
taccacggga ctaaacctgg ttatgtagat tccattcaaa aggtataca aaagccaaaa     120
tctggtacac aaggaaatta tgacgatgat tggaaagagt tttatagtac cgacaataaa    180
tacgacgctg cggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtggtggcg gtggcagcgg tggcggtggc    600
agcggtggcg gtggatcctc cccagcccca tcgcgccctt tttctgtcct ccgagctaat    660
gatgtgcttt ggctttctct caccgctgcc gagtatgacc agtccactta cggctcttcg    720
accggcccag tctatgtctc tgactctgtg accttggtta atgttgcgac cagcgcgcag    780
gccgttgccc ggtcactcga ctggaccaag gtcacacttg atggtcgccc ctttccacc    840
atccagcagc attcaaagac cttctttgtc ctgccgctcc gcggtaagct ctccttttgg    900
gaggcaggta ctactaaagc cgggtaccct tataattata acaccactgc tagtgaccaa    960
ctgctcgttg agaatgccgc tgggcatcgg gttgctattt ccacttacac cactagcctg   1020
ggtgctggcc ccgtctctat ttccgcggtt gctgttttag cccccccctcc gcgc         1074
```

<210> SEQ ID NO 14
<211> LENGTH: 358
<212> TYPE: PRT
<213> ORGANISM: Artificial Sequence
<220> FEATURE:
<223> OTHER INFORMATION: A-L-E2s

<400> SEQUENCE: 14

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
            165                 170                 175

Asp Ala Met Tyr Glu Tyr Met Ala Gln Ala Cys Ala Gly Asn Arg Gly
            180                 185                 190

Gly Gly Gly Ser Gly Gly Gly Ser Gly Gly Gly Ser Ser Pro
            195                 200                 205

Ala Pro Ser Arg Pro Phe Ser Val Leu Arg Ala Asn Asp Val Leu Trp
210                 215                 220

Leu Ser Leu Thr Ala Ala Glu Tyr Asp Gln Ser Thr Tyr Gly Ser Ser
225                 230                 235                 240

Thr Gly Pro Val Tyr Val Ser Asp Ser Val Thr Leu Val Asn Val Ala
                245                 250                 255

Thr Ser Ala Gln Ala Val Ala Arg Ser Leu Asp Trp Thr Lys Val Thr
            260                 265                 270

Leu Asp Gly Arg Pro Leu Ser Thr Ile Gln Gln His Ser Lys Thr Phe
            275                 280                 285

Phe Val Leu Pro Leu Arg Gly Lys Leu Ser Phe Trp Glu Ala Gly Thr
290                 295                 300

Thr Lys Ala Gly Tyr Pro Tyr Asn Tyr Asn Thr Thr Ala Ser Asp Gln
305                 310                 315                 320

Leu Leu Val Glu Asn Ala Ala Gly His Arg Val Ala Ile Ser Thr Tyr
                325                 330                 335

Thr Thr Ser Leu Gly Ala Gly Pro Val Ser Ile Ser Ala Val Ala Val
            340                 345                 350

Leu Ala Pro Pro Pro Arg
            355

<210> SEQ ID NO 15
<211> LENGTH: 1626
<212> TYPE: DNA
<213> ORGANISM: Artificial Sequence
<220> FEATURE:
<223> OTHER INFORMATION: 389-E2s

<400> SEQUENCE: 15
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagagt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa aacagtatct     720

```
gaggaaaaag ctaaacaata cctagaagaa tttcatcaaa cggcattaga gcatcctgaa      780
ttgtcagaac ttaaaaccgt tactgggacc aatcctgtat tcgctggggc taactatgcg      840
gcgtgggcag taaacgttgc gcaagttatc gatagcgaaa cagctgataa tttggaaaag      900
acaactgctg ctctttcgat acttcctggt atcggtagcg taatgggcat tgcagacggt      960
gccgttcacc acaatacaga agagatagtg gcacaatcaa tagctttatc gtctttaatg     1020
gttgctcaag ctattccatt ggtaggagag ctagttgata ttggtttcgc tgcatataat     1080
tttgtagaga gtattatcaa tttatttcaa gtagttcata attcgtataa tcgtcccgcg     1140
tattctccgg ggcataaaac gcaaccattt tccccagccc catcgcgccc tttttctgtc     1200
ctccgagcta atgatgtgct ttggctttct ctcaccgctg ccgagtatga ccagtccact     1260
tacggctctt cgaccggccc agtctatgtc tctgactctg tgaccttggt taatgttgcg     1320
accagcgcgc aggccgttgc ccggtcactc gactggacca aggtcacact tgatggtcgc     1380
cccctttcca ccatccagca gcattcaaag accttctttg tcctgccgct ccgcggtaag     1440
ctctcctttt gggaggcagg tactactaaa gccgggtacc cttataatta taacaccact     1500
gctagtgacc aactgctcgt tgagaatgcc gctgggcatc gggttgctat ttccacttac     1560
accactagcc tgggtgctgg ccccgtctct atttccgcgg ttgctgtttt agccccccct     1620
ccgcgc                                                                1626
```

<210> SEQ ID NO 16
<211> LENGTH: 542
<212> TYPE: PRT
<213> ORGANISM: Artificial Sequence
<220> FEATURE:
<223> OTHER INFORMATION: 389-E2s

<400> SEQUENCE: 16

```
Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
```

```
                195                 200                 205
Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Phe Ser Pro Ala Pro Ser Arg Pro Phe Ser Val
385                 390                 395                 400

Leu Arg Ala Asn Asp Val Leu Trp Leu Ser Leu Thr Ala Ala Glu Tyr
                405                 410                 415

Asp Gln Ser Thr Tyr Gly Ser Ser Thr Gly Pro Val Tyr Val Ser Asp
            420                 425                 430

Ser Val Thr Leu Val Asn Val Ala Thr Ser Ala Gln Ala Val Ala Arg
        435                 440                 445

Ser Leu Asp Trp Thr Lys Val Thr Leu Asp Gly Arg Pro Leu Ser Thr
    450                 455                 460

Ile Gln Gln His Ser Lys Thr Phe Phe Val Leu Pro Leu Arg Gly Lys
465                 470                 475                 480

Leu Ser Phe Trp Glu Ala Gly Thr Thr Lys Ala Gly Tyr Pro Tyr Asn
                485                 490                 495

Tyr Asn Thr Thr Ala Ser Asp Gln Leu Leu Val Glu Asn Ala Ala Gly
            500                 505                 510

His Arg Val Ala Ile Ser Thr Tyr Thr Thr Ser Leu Gly Ala Gly Pro
        515                 520                 525

Val Ser Ile Ser Ala Val Ala Val Leu Ala Pro Pro Arg
    530                 535                 540

<210> SEQ ID NO 17
<211> LENGTH: 1029
<212> TYPE: DNA
<213> ORGANISM: Artificial Sequence
<220> FEATURE:
<223> OTHER INFORMATION: A-E2s

<400> SEQUENCE: 17
atgggcgctg atgatgttgt tgattcttct aaatcttttg tgatggaaaa cttttcttcg    60
taccacggga ctaaacctgg ttatgtagat tccattcaaa aaggtataca aaagccaaaa   120
```

-continued

```
tctggtacac aaggaaatta tgacgatgat tggaaagagt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgttccccag ccccatcgcg cccttttcct    600
gtcctccgag ctaatgatgt gctttggctt tctctcaccg ctgccgagta tgaccagtcc    660
acttacggct cttcgaccgg cccagtctat gtctctgact ctgtgacctt ggttaatgtt    720
gcgaccagcg cgcaggccgt tgcccggtca ctcgactgga ccaaggtcac acttgatggt    780
cgccccctttt ccaccatcca gcagcattca aagaccttct tgtcctgcc gctccgcggt    840
aagctctcct tttgggaggc aggtactact aaagccgggt acccttataa ttataacacc    900
actgctagtg accaactgct cgttgagaat gccgctgggc atcgggttgc tatttccact    960
tacaccacta gcctgggtgc tggccccgtc tctatttccg cggttgctgt tttagccccc   1020
cctccgcgc                                                          1029
```

<210> SEQ ID NO 18
<211> LENGTH: 343
<212> TYPE: PRT
<213> ORGANISM: Artificial Sequence
<220> FEATURE:
<223> OTHER INFORMATION: A-E2s

<400> SEQUENCE: 18

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Ser
            180                 185                 190

Pro Ala Pro Ser Arg Pro Phe Ser Val Leu Arg Ala Asn Asp Val Leu
```

```
            195                 200                 205
Trp Leu Ser Leu Thr Ala Ala Glu Tyr Asp Gln Ser Thr Tyr Gly Ser
    210                 215                 220

Ser Thr Gly Pro Val Tyr Val Ser Asp Ser Val Thr Leu Val Asn Val
225                 230                 235                 240

Ala Thr Ser Ala Gln Ala Val Ala Arg Ser Leu Asp Trp Thr Lys Val
                245                 250                 255

Thr Leu Asp Gly Arg Pro Leu Ser Thr Ile Gln Gln His Ser Lys Thr
            260                 265                 270

Phe Phe Val Leu Pro Leu Arg Gly Lys Leu Ser Phe Trp Glu Ala Gly
            275                 280                 285

Thr Thr Lys Ala Gly Tyr Pro Tyr Asn Tyr Asn Thr Thr Ala Ser Asp
            290                 295                 300

Gln Leu Leu Val Glu Asn Ala Ala Gly His Arg Val Ala Ile Ser Thr
305                 310                 315                 320

Tyr Thr Thr Ser Leu Gly Ala Gly Pro Val Ser Ile Ser Ala Val Ala
                325                 330                 335

Val Leu Ala Pro Pro Pro Arg
                340

<210> SEQ ID NO 19
<211> LENGTH: 33
<212> TYPE: DNA
<213> ORGANISM: Artificial Sequence
<220> FEATURE:
<223> OTHER INFORMATION: primer

<400> SEQUENCE: 19
catatgggcg ctgatgatgt tgttgattct tct                               33

<210> SEQ ID NO 20
<211> LENGTH: 27
<212> TYPE: DNA
<213> ORGANISM: Artificial Sequence
<220> FEATURE:
<223> OTHER INFORMATION: primer

<400> SEQUENCE: 20
gaattcccca ctacctttca gcttttg                                      27

<210> SEQ ID NO 21
<211> LENGTH: 54
<212> TYPE: DNA
<213> ORGANISM: Artificial Sequence
<220> FEATURE:
<223> OTHER INFORMATION: primer

<400> SEQUENCE: 21
ggatccaccg ccaccgctgc caccgccacc gctgccaccg ccaccgcttt tgat        54

<210> SEQ ID NO 22
<211> LENGTH: 55
<212> TYPE: DNA
<213> ORGANISM: Artificial Sequence
<220> FEATURE:
<223> OTHER INFORMATION: primer

<400> SEQUENCE: 22
ggatccaccg ccaccgctgc caccgccacc gctgccaccg ccaccaaatg gttgc       55

<210> SEQ ID NO 23
```

<211> LENGTH: 59
<212> TYPE: DNA
<213> ORGANISM: Artificial Sequence
<220> FEATURE:
<223> OTHER INFORMATION: primer

<400> SEQUENCE: 23
ggatccaccg ccaccgctgc caccgccacc gctgccaccg ccaccacgat ttcctgcac    59

<210> SEQ ID NO 24
<211> LENGTH: 25
<212> TYPE: DNA
<213> ORGANISM: Artificial Sequence
<220> FEATURE:
<223> OTHER INFORMATION: primer

<400> SEQUENCE: 24
ggatcccagc tgttctactc tcgtc    25

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
ggatcctccc cagcccccatc gcgc    24

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
gaattcctag cgcggagggg gggct    25

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
gatggggctg gggaaaatgg ttg    23

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
gatggggctg gggaacgatt tcctgcac    28

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29

-continued

```
cgcaaccatt tcccccagcc c                                              21

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
gaaatcgttc cccagcccca t                                              21

<210> SEQ ID NO 31
<211> LENGTH: 660
<212> TYPE: PRT
<213> ORGANISM: Hepatitis E virus

<400> SEQUENCE: 31
```

Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Gly Arg
            20                  25                  30

Arg Ser Gly Gly Ser Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Thr Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
            85                  90                  95

Ala Ser Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
            325                 330                 335

Gly Thr Ala Glu Leu Thr Thr Thr Ala Ala Thr Arg Phe Met Lys Asp
                340                 345                 350

Leu Tyr Phe Thr Ser Thr Asn Gly Val Gly Glu Ile Gly Arg Gly Ile
            355                 360                 365

Ala Leu Thr Leu Phe Asn Leu Ala Asp Thr Leu Leu Gly Gly Leu Pro
370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
                420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Ile Gln Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Ala Pro His Ser Ala Leu Ala
            595                 600                 605

Leu Leu Glu Asp Thr Met Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 32
<211> LENGTH: 97
<212> TYPE: PRT
<213> ORGANISM: Influenza virus

<400> SEQUENCE: 32

Met Ser Leu Leu Thr Glu Val Glu Thr Pro Ile Arg Asn Gly Trp Gly

```
              1               5                  10                  15
Cys Arg Cys Asn Asp Ser Ser Asp Pro Leu Val Val Ala Ala Ser Ile
                            20                  25                  30

Ile Gly Ile Val His Leu Ile Leu Trp Ile Ile Asp Arg Leu Phe Ser
                35                  40                  45

Lys Ser Ile Tyr Arg Ile Phe Lys His Gly Leu Lys Arg Gly Pro Ser
        50                  55                  60

Thr Glu Gly Val Pro Glu Ser Met Arg Glu Glu Tyr Arg Glu Glu Gln
65                  70                  75                  80

Gln Asn Ala Val Asp Ala Asp Asp Asp His Phe Val Ser Ile Glu Leu
                    85                  90                  95

Glu

<210> SEQ ID NO 33
<211> LENGTH: 1713
<212> TYPE: DNA
<213> ORGANISM: Artificial Sequence
<220> FEATURE:
<223> OTHER INFORMATION: CRM197-L-M2e

<400> SEQUENCE: 33
atgggcgctg atgatgttgt tgattcttct aaatcttttg tgatggaaaa cttttcttcg      60
taccacggga ctaaacctgg ttatgtagat tccattcaaa aaggtataca aaagccaaaa     120
tctggtacac aaggaaatta tgacgatgat tggaaagagt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatcagtagg tagctcattg     600
tcatgcataa atcttgattg ggatgtcata agggataaaa ctaagacaaa gatagagtct     660
ttgaaagagc atggccctat caaaaataaa atgagcgaaa gtcccaataa aacagtatct     720
gaggaaaaag ctaaacaata cctagaagaa tttcatcaaa cggcattaga gcatcctgaa     780
ttgtcagaac ttaaaaccgt tactgggacc aatcctgtat cgctggggc taactatgcg     840 gcgtgggcag taaacgttgc gcaagttatc gatagcgaaa cagctgataa tttggaaaag     900
acaactgctg ctcttcgat acttcctggt atcggtagcg taatgggcat tgcagacggt     960
gccgttcacc acaatacaga agagatagtg cacaatcaa tagctttatc gtctttaatg    1020
gttgctcaag ctattccatt ggtaggagag ctagttgata ttggtttcgc tgcatataat    1080
tttgtagaga gtattatcaa tttatttcaa gtagttcata attcgtataa tcgtcccgcg    1140
tattctccgg ggcataaaac gcaaccattt cttcatgacg ggtatgctgt cagttggaac    1200
actgttgaag attcgataat ccgaactggt tttcaagggg agagtgggca cgacataaaa    1260
attactgctg aaaatacccc gcttccaatc gcgggtgtcc tactaccgac tattcctgga    1320
aagctggacg ttaataagtc caagactcat atttccgtaa atggtcggaa aataaggatg    1380
cgttgcagag ctagacggt gatgtaact ttttgtcgcc ctaaatctcc tgtttatgtt    1440
ggtaatggtg tgcatgcgaa tcttcacgtg gcatttcaca gaagcagctc ggagaaaatt    1500
```

```
cattctaatg aaatttcgtc ggattccata ggcgttcttg ggtaccagaa aacagtagat   1560
cacaccaagg ttaattctaa gctatcgcta ttttttgaaa tcaaaagcgg tggcggtggc   1620
agcggtggcg gtggcagcat gagtcttcta accgaggtcg aaacgcctat cagaaacgaa   1680
tgggggtgca gatgcaacgg ttcaagtgat taa                                1713
```

<210> SEQ ID NO 34
<211> LENGTH: 570
<212> TYPE: PRT
<213> ORGANISM: Artificial Sequence
<220> FEATURE:
<223> OTHER INFORMATION: CRM197-L-M2e

<400> SEQUENCE: 34

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
```

```
                        325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
        355                 360                 365
Phe Gln Val Val His Asn Ser Tyr Asn Arg Pro Ala Tyr Ser Pro Gly
    370                 375                 380
His Lys Thr Gln Pro Phe Leu His Asp Gly Tyr Ala Val Ser Trp Asn
385                 390                 395                 400
Thr Val Glu Asp Ser Ile Ile Arg Thr Gly Phe Gln Gly Ser Gly
                405                 410                 415
His Asp Ile Lys Ile Thr Ala Glu Asn Thr Pro Leu Pro Ile Ala Gly
            420                 425                 430
Val Leu Leu Pro Thr Ile Pro Gly Lys Leu Asp Val Asn Lys Ser Lys
        435                 440                 445
Thr His Ile Ser Val Asn Gly Arg Lys Ile Arg Met Arg Cys Arg Ala
    450                 455                 460
Ile Asp Gly Asp Val Thr Phe Cys Arg Pro Lys Ser Pro Val Tyr Val
465                 470                 475                 480
Gly Asn Gly Val His Ala Asn Leu His Val Ala Phe His Arg Ser Ser
                485                 490                 495
Ser Glu Lys Ile His Ser Asn Glu Ile Ser Ser Asp Ser Ile Gly Val
            500                 505                 510
Leu Gly Tyr Gln Lys Thr Val Asp His Thr Lys Val Asn Ser Lys Leu
        515                 520                 525
Ser Leu Phe Phe Glu Ile Lys Ser Gly Gly Gly Ser Gly Gly Gly
    530                 535                 540
Gly Ser Met Ser Leu Leu Thr Glu Val Glu Thr Pro Ile Arg Asn Glu
545                 550                 555                 560
Trp Gly Cys Arg Cys Asn Gly Ser Ser Asp
                565                 570

<210> SEQ ID NO 35
<211> LENGTH: 1275
<212> TYPE: DNA
<213> ORGANISM: Artificial Sequence
<220> FEATURE:
<223> OTHER INFORMATION: 389-L-M2e

<400> SEQUENCE: 35
atgggcgctg atgatgttgt tgattcttct aaatcttttg tgatggaaaa ctttttcttcg    60 taccacggga ctaaacctgg ttatgtagat tccattcaaa aaggtataca aaagccaaaa   120
tctggtacac aaggaaatta tgacgatgat tggaaagagt tttatagtac cgacaataaa   180
tacgacgctg cgggatactc tgtagataat gaaaacccgc tctctggaaa agctggaggc   240
gtggtcaaag tgacgtatcc aggactgacg aaggttctcg cactaaaagt ggataatgcc   300
gaaactatta agaaagagtt aggtttaagt ctcactgaac cgttgatgga gcaagtcgga   360
acggaagagt ttatcaaaag gttcggtgat ggtgcttcgc gtgtagtgct cagccttccc   420
ttcgctgagg ggagttctag cgttgaatat attaataact gggaacaggc gaaagcgtta   480
agcgtagaac ttgagattaa ttttgaaacc cgtggaaaac gtggccaaga tgcgatgtat   540
gagtatatgg ctcaagcctg tgcaggaaat cgtgtcaggc gatcagtagg tagctcattg   600
tcatgcataa atcttgattg ggatgtcata agggataaaa ctaagacaaa gatagagtct   660
```

```
ttgaaagagc atggccctat caaaataaa atgagcgaaa gtcccaataa aacagtatct    720
gaggaaaaag ctaaacaata cctagaagaa tttcatcaaa cggcattaga gcatcctgaa    780
ttgtcagaac ttaaaaccgt tactgggacc aatcctgtat tcgctggggc taactatgcg    840
gcgtgggcag taacgttgc gcaagttatc gatagcgaaa cagctgataa tttggaaaag    900
acaactgctg ctctttcgat acttcctggt atcggtagcg taatgggcat tgcagacggt    960
gccgttcacc acaatacaga agagatagtg gcacaatcaa tagctttatc gtctttaatg   1020
gttgctcaag ctattccatt ggtaggagag ctagttgata ttggtttcgc tgcatataat   1080
tttgtagaga gtattatcaa tttatttcaa gtagttcata attcgtataa tcgtcccgcg   1140
tattctccgg ggcataaaac gcaaccattt ggtggcggtg gcagcggtgg cggtggcagc   1200
atgagtcttc taaccgaggt cgaaacgcct atcagaaacg aatgggggtg cagatgcaac   1260
ggttcaagtg attaa                                                    1275
```

<210> SEQ ID NO 36
<211> LENGTH: 424
<212> TYPE: PRT
<213> ORGANISM: Artificial Sequence
<220> FEATURE:
<223> OTHER INFORMATION: 389-L-M2e

<400> SEQUENCE: 36

Met Gly Ala Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
                20                  25                  30

Gln Lys Gly Ile Gln Lys Pro Lys Ser Gly Thr Gln Gly Asn Tyr Asp
            35                  40                  45

Asp Asp Trp Lys Glu Phe Tyr Ser Thr Asp Asn Lys Tyr Asp Ala Ala
        50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
              260                 265                 270

Val Phe Ala Gly Ala Asn Tyr Ala Ala Trp Ala Val Asn Val Ala Gln
          275                 280                 285

Val Ile Asp Ser Glu Thr Ala Asp Asn Leu Glu Lys Thr Thr Ala Ala
      290                 295                 300

Leu Ser Ile Leu Pro Gly Ile Gly Ser Val Met Gly Ile Ala Asp Gly
305                 310                 315                 320

Ala Val His His Asn Thr Glu Ile Val Ala Gln Ser Ile Ala Leu
              325                 330                 335

Ser Ser Leu Met Val Ala Gln Ala Ile Pro Leu Val Gly Glu Leu Val
              340                 345                 350

Asp Ile Gly Phe Ala Ala Tyr Asn Phe Val Glu Ser Ile Ile Asn Leu
              355                 360                 365

Phe Gln Val Val His Asn Ser Tyr Asn Arg Pro Ala Tyr Ser Pro Gly
          370                 375                 380

His Lys Thr Gln Pro Phe Gly Gly Gly Ser Gly Gly Gly Gly Ser
385                 390                 395                 400

Met Ser Leu Leu Thr Glu Val Glu Thr Pro Ile Arg Asn Glu Trp Gly
              405                 410                 415

Cys Arg Cys Asn Gly Ser Ser Asp
              420

<210> SEQ ID NO 37
<211> LENGTH: 678
<212> TYPE: DNA
<213> ORGANISM: Artificial Sequence
<220> FEATURE:
<223> OTHER INFORMATION: A-L-M2e

<400> SEQUENCE: 37
atgggcgctg atgatgttgt tgattcttct aaatcttttg tgatggaaaa ctttttcttcg      60 taccacggga ctaaacctgg ttatgtagat tccattcaaa aaggtataca aaagccaaaa     120
tctggtacac aaggaaatta tgacgatgat tggaaagagt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta gaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtggtggcg gtgcagcggt ggcggtggc     600 agcatgagtc ttctaaccga ggtcgaaacg cctatcagaa cgaatggggg gtgcagatgc     660
aacggttcaa gtgattaa                                                  678

<210> SEQ ID NO 38
<211> LENGTH: 225
<212> TYPE: PRT
<213> ORGANISM: Artificial Sequence
<220> FEATURE:
<223> OTHER INFORMATION: A-L-M2e

<400> SEQUENCE: 38

Met Gly Ala Asp Asp Val Val Asp Ser Ser Lys Ser Phe Val Met Glu

```
                1               5              10              15
Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
            35                  40                  45

Asp Trp Lys Glu Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
 65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Gly
            180                 185                 190

Gly Gly Gly Ser Gly Gly Gly Gly Ser Met Ser Leu Leu Thr Glu Val
            195                 200                 205

Glu Thr Pro Ile Arg Asn Glu Trp Gly Cys Arg Cys Asn Gly Ser Ser
            210                 215                 220

Asp
225

<210> SEQ ID NO 39
<211> LENGTH: 1713
<212> TYPE: DNA
<213> ORGANISM: Artificial Sequence
<220> FEATURE:
<223> OTHER INFORMATION: M2e-L-CRM197

<400> SEQUENCE: 39
atgatgagtc ttctaaccga ggtcgaaacg cctatcagaa acgaatgggg gtgcagatgc      60
aacggttcaa gtgatggtgg cggtggcagc ggtggcggtg gcagcggcgc tgatgatgtt     120
gttgattctt ctaaatcttt tgtgatggaa actttttctt cgtaccacgg gactaaacct     180
ggttatgtag attccattca aaaaggtata caaaagccaa atctggtaca caaggaaat     240 tatgacgatg attggaaaga gttttatagt accgacaata atacgacgc tgcgggatac     300 tctgtagata tgaaaaaccc gctctctgga aaagctggag cgtggtcaa agtgacgtat     360 ccaggactga cgaaggttct cgcactaaaa gtggataatg ccgaaactat taagaaagag     420
ttaggtttaa gtctcactga accgttgatg gagcaagtcg gaacggaaga gtttatcaaa     480
aggttcggtg atggtgcttc gcgtgtagtg ctcagcctc ccttcgctga ggggagttct     540
agcgttgaat atattaataa ctgggaacag gcgaaagcgt taagcgtaga acttgagatt     600
aattttgaaa cccgtggaaa acgtggccaa gatgcgatgt atgagtatat ggctcaagcc     660
tgtgcaggaa atcgtgtcag gcgatcagta ggtagctcat tgtcatgcat aaatcttgat     720
tgggatgtca aagggataaa actaagaca aagatagagt ctttgaaaga gcatggccct     780
```

```
atcaaaaata aaatgagcga aagtcccaat aaaacagtat ctgaggaaaa agctaaacaa    840
tacctagaag aatttcatca aacggcatta gagcatcctg aattgtcaga acttaaaacc    900
gttactggga ccaatcctgt attcgctggg gctaactatg cggcgtgggc agtaaacgtt    960
gcgcaagtta tcgatagcga aacagctgat aatttggaaa agacaactgc tgctctttcg   1020
atacttcctg gtatcggtag cgtaatgggc attgcagacg tgccgttca ccacaataca    1080 gaagagatag tggcacaatc aatagcttta tcgtctttaa tggttgctca agctattcca   1140
ttggtaggag agctagttga tattggtttc gctgcatata attttgtaga gagtattatc   1200
aatttatttc aagtagttca taattcgtat aatcgtcccg cgtattctcc ggggcataaa   1260
acgcaaccat ttcttcatga cgggtatgct gtcagttgga acactgttga agattcgata   1320
atccgaactg gttttcaagg ggagagtggg cacgacataa aaattactgc tgaaaatacc   1380
ccgcttccaa tcgcgggtgt cctactaccg actattcctg gaaagctgga cgttaataag   1440
tccaagactc atatttccgt aaatggtcgg aaaataagga tgcgttgcag agctatagac   1500
ggtgatgtaa cttttgtcg ccctaaatct cctgtttatg ttggtaatgg tgtgcatgcg    1560
aatcttcacg tggcatttca cagaagcagc tcggagaaaa ttcattctaa tgaaatttcg   1620
tcggattcca taggcgttct tgggtaccag aaaacagtag atcacaccaa ggttaattct   1680
aagctatcgc tattttttga aatcaaaagc taa                                1713
```

<210> SEQ ID NO 40
<211> LENGTH: 570
<212> TYPE: PRT
<213> ORGANISM: Artificial Sequence
<220> FEATURE:
<223> OTHER INFORMATION: M2e-L-CRM197

<400> SEQUENCE: 40

```
Met Met Ser Leu Leu Thr Glu Val Glu Thr Pro Ile Arg Asn Glu Trp
1               5                   10                  15

Gly Cys Arg Cys Asn Gly Ser Ser Asp Gly Gly Gly Ser Gly Gly
            20                  25                  30

Gly Gly Ser Gly Ala Asp Asp Val Val Asp Ser Ser Lys Ser Phe Val
        35                  40                  45

Met Glu Asn Phe Ser Ser Tyr His Gly Thr Lys Pro Gly Tyr Val Asp
    50                  55                  60

Ser Ile Gln Lys Gly Ile Gln Lys Pro Lys Ser Gly Thr Gln Gly Asn
65                  70                  75                  80

Tyr Asp Asp Asp Trp Lys Glu Phe Tyr Ser Thr Asp Asn Lys Tyr Asp
                85                  90                  95

Ala Ala Gly Tyr Ser Val Asp Asn Glu Asn Pro Leu Ser Gly Lys Ala
            100                 105                 110

Gly Gly Val Val Lys Val Thr Tyr Pro Gly Leu Thr Lys Val Leu Ala
        115                 120                 125

Leu Lys Val Asp Asn Ala Glu Thr Ile Lys Lys Glu Leu Gly Leu Ser
    130                 135                 140

Leu Thr Glu Pro Leu Met Glu Gln Val Gly Thr Glu Glu Phe Ile Lys
145                 150                 155                 160

Arg Phe Gly Asp Gly Ala Ser Arg Val Val Leu Ser Leu Pro Phe Ala
                165                 170                 175

Glu Gly Ser Ser Ser Val Glu Tyr Ile Asn Asn Trp Glu Gln Ala Lys
            180                 185                 190
```

Ala Leu Ser Val Glu Leu Glu Ile Asn Phe Glu Thr Arg Gly Lys Arg
    195                 200                 205

Gly Gln Asp Ala Met Tyr Glu Tyr Met Ala Gln Ala Cys Ala Gly Asn
210                 215                 220

Arg Val Arg Arg Ser Val Gly Ser Ser Leu Ser Cys Ile Asn Leu Asp
225                 230                 235                 240

Trp Asp Val Ile Arg Asp Lys Thr Lys Thr Lys Ile Glu Ser Leu Lys
            245                 250                 255

Glu His Gly Pro Ile Lys Asn Lys Met Ser Glu Ser Pro Asn Lys Thr
        260                 265                 270

Val Ser Glu Glu Lys Ala Lys Gln Tyr Leu Glu Glu Phe His Gln Thr
    275                 280                 285

Ala Leu Glu His Pro Glu Leu Ser Glu Leu Lys Thr Val Thr Gly Thr
290                 295                 300

Asn Pro Val Phe Ala Gly Ala Asn Tyr Ala Ala Trp Ala Val Asn Val
305                 310                 315                 320

Ala Gln Val Ile Asp Ser Glu Thr Ala Asp Asn Leu Glu Lys Thr Thr
            325                 330                 335

Ala Ala Leu Ser Ile Leu Pro Gly Ile Gly Ser Val Met Gly Ile Ala
        340                 345                 350

Asp Gly Ala Val His His Asn Thr Glu Glu Ile Val Ala Gln Ser Ile
    355                 360                 365

Ala Leu Ser Ser Leu Met Val Ala Gln Ala Ile Pro Leu Val Gly Glu
370                 375                 380

Leu Val Asp Ile Gly Phe Ala Ala Tyr Asn Phe Val Glu Ser Ile Ile
385                 390                 395                 400

Asn Leu Phe Gln Val Val His Asn Ser Tyr Asn Arg Pro Ala Tyr Ser
            405                 410                 415

Pro Gly His Lys Thr Gln Pro Phe Leu His Asp Gly Tyr Ala Val Ser
        420                 425                 430

Trp Asn Thr Val Glu Asp Ser Ile Ile Arg Thr Gly Phe Gln Gly Glu
    435                 440                 445

Ser Gly His Asp Ile Lys Ile Thr Ala Glu Asn Thr Pro Leu Pro Ile
450                 455                 460

Ala Gly Val Leu Leu Pro Thr Ile Pro Gly Lys Leu Asp Val Asn Lys
465                 470                 475                 480

Ser Lys Thr His Ile Ser Val Asn Gly Arg Lys Ile Arg Met Arg Cys
            485                 490                 495

Arg Ala Ile Asp Gly Asp Val Thr Phe Cys Arg Pro Lys Ser Pro Val
        500                 505                 510

Tyr Val Gly Asn Gly Val His Ala Asn Leu His Val Ala Phe His Arg
    515                 520                 525

Ser Ser Ser Glu Lys Ile His Ser Asn Glu Ile Ser Ser Asp Ser Ile
530                 535                 540

Gly Val Leu Gly Tyr Gln Lys Thr Val Asp His Thr Lys Val Asn Ser
545                 550                 555                 560

Lys Leu Ser Leu Phe Phe Glu Ile Lys Ser
            565                 570

<210> SEQ ID NO 41
<211> LENGTH: 1275
<212> TYPE: DNA
<213> ORGANISM: Artificial Sequence
<220> FEATURE:
<223> OTHER INFORMATION: M2e-L-389

<400> SEQUENCE: 41

```
atgatgagtc ttctaaccga ggtcgaaacg cctatcagaa cgaatgggg gtgcagatgc         60
aacggttcaa gtgatggtgg cggtggcagc ggtggcggtg gcagcggcgc tgatgatgtt        120
gttgattctt ctaaatcttt tgtgatggaa actttctt cgtaccacgg gactaaacct         180
ggttatgtag attccattca aaaggtata caaaagccaa atctggtac acaaggaaat          240
tatgacgatg attggaaaga gttttatagt accgacaata aatacgacgc tgcgggatac        300
tctgtagata atgaaaaccc gctctctgga aaagctggag cgtggtcaa agtgacgtat         360
ccaggactga cgaaggttct cgcactaaaa gtggataatg ccgaaactat taagaaagag       420
ttaggtttaa gtctcactga accgttgatg gagcaagtcg gaacggaaga gtttatcaaa        480
aggttcggtg atggtgcttc gcgtgtagtg ctcagccttc ccttcgctga ggggagttct        540
agcgttgaat atattaataa ctgggaacag gcgaaagcgt taagcgtaga acttgagatt        600
aatttgaaa cccgtggaaa acgtggccaa gatgcgatgt atgagtatat ggctcaagcc        660
tgtgcaggaa atcgtgtcag gcgatcagta ggtagctcat tgtcatgcat aaatcttgat       720
tgggatgtca taagggataa aactaagaca aagatagagt ctttgaaaga gcatggccct        780
atcaaaaata aaatgagcga agtcccaat aaaacagtat ctgaggaaaa agctaaacaa        840
tacctagaag aatttcatca aacggcatta gagcatcctg aattgtcaga acttaaaacc       900
gttactggga ccaatcctgt attcgctggg gctaactatg cggcgtgggc agtaaacgtt       960
gcgcaagtta tcgatagcga aacagctgat aatttggaaa agacaactgc tgctctttcg      1020
atacttcctg gtatcggtag cgtaatgggc attgcagacg gtgccgttca ccacaataca      1080
gaagagatag tggcacaatc aatagcttta tcgtctttaa tggttgctca agctattcca      1140
ttggtaggag agctagttga tattggtttc gctgcatata attttgtaga gagtattatc      1200
aatttatttc aagtagttca taattcgtat aatcgtcccg cgtattctcc ggggcataaa      1260
acgcaaccat tttaa                                                         1275
```

<210> SEQ ID NO 42
<211> LENGTH: 424
<212> TYPE: PRT
<213> ORGANISM: Artificial Sequence
<220> FEATURE:
<223> OTHER INFORMATION: M2e-L-389

<400> SEQUENCE: 42

```
Met Met Ser Leu Leu Thr Glu Val Glu Thr Pro Ile Arg Asn Glu Trp
1               5                   10                  15

Gly Cys Arg Cys Asn Gly Ser Ser Asp Gly Gly Gly Ser Gly Gly
            20                  25                  30

Gly Gly Ser Gly Ala Asp Asp Val Val Asp Ser Ser Lys Ser Phe Val
        35                  40                  45

Met Glu Asn Phe Ser Ser Tyr His Gly Thr Lys Pro Gly Tyr Val Asp
    50                  55                  60

Ser Ile Gln Lys Gly Ile Gln Lys Pro Lys Ser Gly Thr Gln Gly Asn
65                  70                  75                  80

Tyr Asp Asp Asp Trp Lys Glu Phe Tyr Ser Thr Asp Asn Lys Tyr Asp
                85                  90                  95

Ala Ala Gly Tyr Ser Val Asp Asn Glu Asn Pro Leu Ser Gly Lys Ala
            100                 105                 110

Gly Gly Val Val Lys Val Thr Tyr Pro Gly Leu Thr Lys Val Leu Ala
```

```
              115                 120                 125
Leu Lys Val Asp Asn Ala Glu Thr Ile Lys Lys Glu Leu Gly Leu Ser
    130                 135                 140

Leu Thr Glu Pro Leu Met Glu Gln Val Gly Thr Glu Phe Ile Lys
145                 150                 155                 160

Arg Phe Gly Asp Gly Ala Ser Arg Val Val Leu Ser Leu Pro Phe Ala
                165                 170                 175

Glu Gly Ser Ser Val Glu Tyr Ile Asn Asn Trp Glu Gln Ala Lys
            180                 185                 190

Ala Leu Ser Val Glu Leu Glu Ile Asn Phe Glu Thr Arg Gly Lys Arg
    195                 200                 205

Gly Gln Asp Ala Met Tyr Glu Tyr Met Ala Gln Ala Cys Ala Gly Asn
    210                 215                 220

Arg Val Arg Arg Ser Val Gly Ser Ser Leu Ser Cys Ile Asn Leu Asp
225                 230                 235                 240

Trp Asp Val Ile Arg Asp Lys Thr Lys Thr Lys Ile Glu Ser Leu Lys
                245                 250                 255

Glu His Gly Pro Ile Lys Asn Lys Met Ser Glu Ser Pro Asn Lys Thr
            260                 265                 270

Val Ser Glu Glu Lys Ala Lys Gln Tyr Leu Glu Glu Phe His Gln Thr
        275                 280                 285

Ala Leu Glu His Pro Glu Leu Ser Glu Leu Lys Thr Val Thr Gly Thr
    290                 295                 300

Asn Pro Val Phe Ala Gly Ala Asn Tyr Ala Ala Trp Ala Val Asn Val
305                 310                 315                 320

Ala Gln Val Ile Asp Ser Glu Thr Ala Asp Asn Leu Glu Lys Thr Thr
                325                 330                 335

Ala Ala Leu Ser Ile Leu Pro Gly Ile Gly Ser Val Met Gly Ile Ala
            340                 345                 350

Asp Gly Ala Val His His Asn Thr Glu Glu Ile Val Ala Gln Ser Ile
        355                 360                 365

Ala Leu Ser Ser Leu Met Val Ala Gln Ala Ile Pro Leu Val Gly Glu
    370                 375                 380

Leu Val Asp Ile Gly Phe Ala Ala Tyr Asn Phe Val Glu Ser Ile Ile
385                 390                 395                 400

Asn Leu Phe Gln Val Val His Asn Ser Tyr Asn Arg Pro Ala Tyr Ser
                405                 410                 415

Pro Gly His Lys Thr Gln Pro Phe
            420

<210> SEQ ID NO 43
<211> LENGTH: 678
<212> TYPE: DNA
<213> ORGANISM: Artificial Sequence
<220> FEATURE:
<223> OTHER INFORMATION: M2e-L-A

<400> SEQUENCE: 43
atgatgagtc ttctaaccga ggtcgaaacg cctatcagaa cgaatggggg gtgcagatgc      60
aacggttcaa gtgatggtgg cggtggcagc ggtggcggtg gcagcggcgc tgatgatgtt     120
gttgattctt ctaaatcttt tgtgatggaa aactttctt cgtaccacgg gactaaacct     180
ggttatgtag attccattca aaaaggtata caaaagccaa atctggtac acaaggaaat     240 tatgacgatg attggaaaga gttttatagt accgacaata aatacgacgc tgcgggatac     300
```

-continued

```
tctgtagata atgaaaaccc gctctctgga aaagctggag gcgtggtcaa agtgacgtat    360
ccaggactga cgaaggttct cgcactaaaa gtggataatg ccgaaactat taagaaagag    420
ttaggtttaa gtctcactga accgttgatg gagcaagtcg gaacggaaga gtttatcaaa    480
aggttcggtg atggtgcttc gcgtgtagtg ctcagccttc ccttcgctga ggggagttct    540
agcgttgaat atattaataa ctgggaacag gcgaaagcgt taagcgtaga acttgagatt    600
aattttgaaa cccgtggaaa acgtggccaa gatgcgatgt atgagtatat ggctcaagcc    660
tgtgcaggaa atcgttaa                                                  678
```

<210> SEQ ID NO 44
<211> LENGTH: 225
<212> TYPE: PRT
<213> ORGANISM: Artificial Sequence
<220> FEATURE:
<223> OTHER INFORMATION: M2e-L-A

<400> SEQUENCE: 44

```
Met Met Ser Leu Leu Thr Glu Val Glu Thr Pro Ile Arg Asn Glu Trp
1               5                   10                  15

Gly Cys Arg Cys Asn Gly Ser Ser Asp Gly Gly Gly Ser Gly Gly
            20                  25                  30

Gly Gly Ser Gly Ala Asp Asp Val Val Asp Ser Ser Lys Ser Phe Val
        35                  40                  45

Met Glu Asn Phe Ser Ser Tyr His Gly Thr Lys Pro Gly Tyr Val Asp
    50                  55                  60

Ser Ile Gln Lys Gly Ile Gln Lys Pro Lys Ser Gly Thr Gln Gly Asn
65                  70                  75                  80

Tyr Asp Asp Asp Trp Lys Glu Phe Tyr Ser Thr Asp Asn Lys Tyr Asp
                85                  90                  95

Ala Ala Gly Tyr Ser Val Asp Asn Glu Asn Pro Leu Ser Gly Lys Ala
            100                 105                 110

Gly Gly Val Val Lys Val Thr Tyr Pro Gly Leu Thr Lys Val Leu Ala
        115                 120                 125

Leu Lys Val Asp Asn Ala Glu Thr Ile Lys Lys Glu Leu Gly Leu Ser
130                 135                 140

Leu Thr Glu Pro Leu Met Glu Gln Val Gly Thr Glu Glu Phe Ile Lys
145                 150                 155                 160

Arg Phe Gly Asp Gly Ala Ser Arg Val Val Leu Ser Leu Pro Phe Ala
                165                 170                 175

Glu Gly Ser Ser Ser Val Glu Tyr Ile Asn Asn Trp Glu Gln Ala Lys
            180                 185                 190

Ala Leu Ser Val Glu Leu Glu Ile Asn Phe Glu Thr Arg Gly Lys Arg
        195                 200                 205

Gly Gln Asp Ala Met Tyr Glu Tyr Met Ala Gln Ala Cys Ala Gly Asn
    210                 215                 220

Arg
225
```

<210> SEQ ID NO 45
<211> LENGTH: 51
<212> TYPE: DNA
<213> ORGANISM: Artificial Sequence
<220> FEATURE:
<223> OTHER INFORMATION: primer

<400> SEQUENCE: 45
catatgggcg ctgatgatgt tgttgattct tctaaatctt ttgtgatgga a      51

<210> SEQ ID NO 46
<211> LENGTH: 45
<212> TYPE: DNA
<213> ORGANISM: Artificial Sequence
<220> FEATURE:
<223> OTHER INFORMATION: primer

<400> SEQUENCE: 46
ggatccgctg ccaccgccac cgctgccacc gccaccgctt ttgat      45

<210> SEQ ID NO 47
<211> LENGTH: 45
<212> TYPE: DNA
<213> ORGANISM: Artificial Sequence
<220> FEATURE:
<223> OTHER INFORMATION: primer

<400> SEQUENCE: 47
ggatccgctg ccaccgccac cgctgccacc gccaccaaat ggttg      45

<210> SEQ ID NO 48
<211> LENGTH: 45
<212> TYPE: DNA
<213> ORGANISM: Artificial Sequence
<220> FEATURE:
<223> OTHER INFORMATION: primer

<400> SEQUENCE: 48
ggatccgctg ccaccgccac cgctgccacc gccaccacga tttcc      45

<210> SEQ ID NO 49
<211> LENGTH: 36
<212> TYPE: DNA
<213> ORGANISM: Artificial Sequence
<220> FEATURE:
<223> OTHER INFORMATION: primer

<400> SEQUENCE: 49
ggatccatga gtcttctaac cgaggtcgaa acgcct      36

<210> SEQ ID NO 50
<211> LENGTH: 39
<212> TYPE: DNA
<213> ORGANISM: Artificial Sequence
<220> FEATURE:
<223> OTHER INFORMATION: primer

<400> SEQUENCE: 50
gaattcttaa tcacttgaac cgttgcatct gcaccccca      39

<210> SEQ ID NO 51
<211> LENGTH: 36
<212> TYPE: DNA
<213> ORGANISM: Artificial Sequence
<220> FEATURE:
<223> OTHER INFORMATION: primer

<400> SEQUENCE: 51
catatgatga gtcttctaac cgaggtcgaa acgcct      36

<210> SEQ ID NO 52
<211> LENGTH: 45
<212> TYPE: DNA
<213> ORGANISM: Artificial Sequence

```
<220> FEATURE:
<223> OTHER INFORMATION: primer

<400> SEQUENCE: 52
ggatccgctg ccaccgccac cgctgccacc gccaccatca cttga                45

<210> SEQ ID NO 53
<211> LENGTH: 51
<212> TYPE: DNA
<213> ORGANISM: Artificial Sequence
<220> FEATURE:
<223> OTHER INFORMATION: primer

<400> SEQUENCE: 53
ggatccggcg ctgatgatgt tgttgattct tctaaatctt ttgtgatgga a          51

<210> SEQ ID NO 54
<211> LENGTH: 42
<212> TYPE: DNA
<213> ORGANISM: Artificial Sequence
<220> FEATURE:
<223> OTHER INFORMATION: primer

<400> SEQUENCE: 54
gaattctaag cttttgattt caaaaaatag cgatagctta ga                   42

<210> SEQ ID NO 55
<211> LENGTH: 42
<212> TYPE: DNA
<213> ORGANISM: Artificial Sequence
<220> FEATURE:
<223> OTHER INFORMATION: primer

<400> SEQUENCE: 55
gaattctaaa aatggttgcg ttttatgccc cggagaatac gc                   42

<210> SEQ ID NO 56
<211> LENGTH: 42
<212> TYPE: DNA
<213> ORGANISM: Artificial Sequence
<220> FEATURE:
<223> OTHER INFORMATION: primer

<400> SEQUENCE: 56
gaattctaaa cgatttcctg cacaggcttg agccatatac tc                   42

<210> SEQ ID NO 57
<211> LENGTH: 4
<212> TYPE: PRT
<213> ORGANISM: Artificial Sequence
<220> FEATURE:
<223> OTHER INFORMATION: linker

<400> SEQUENCE: 57

Gly Gly Gly Gly

<210> SEQ ID NO 58
<211> LENGTH: 5
<212> TYPE: PRT
<213> ORGANISM: Artificial Sequence
<220> FEATURE:
<223> OTHER INFORMATION: linker

<400> SEQUENCE: 58

Gly Gly Gly Gly Ser
1               5
```

```
<210> SEQ ID NO 59
<211> LENGTH: 4
<212> TYPE: PRT
<213> ORGANISM: Artificial Sequence
<220> FEATURE:
<223> OTHER INFORMATION: linker

<400> SEQUENCE: 59

Gly Gly Ser Ser
1

<210> SEQ ID NO 60
<211> LENGTH: 15
<212> TYPE: PRT
<213> ORGANISM: Artificial Sequence
<220> FEATURE:
<223> OTHER INFORMATION: linker

<400> SEQUENCE: 60

Gly Gly Gly Gly Ser Gly Gly Gly Gly Ser Gly Gly Gly Gly Ser
1               5                   10                  15
```